United States Patent
Large et al.

(10) Patent No.: US 11,147,813 B2
(45) Date of Patent: Oct. 19, 2021

(54) MODULATORS OF KV3 CHANNELS TO TREAT PAIN

(71) Applicant: Autifony Therapeutics Limited, Stevenage (GB)

(72) Inventors: Charles Large, Stevenage (GB); Giuseppe Alvaro, Stevenage (GB)

(73) Assignee: Autifony Therapeutics Limited, Stevenage (GB)

( * ) Notice: Subject to any disclaimer, the term of this patent is extended or adjusted under 35 U.S.C. 154(b) by 0 days.

(21) Appl. No.: 16/060,714

(22) PCT Filed: Dec. 9, 2016

(86) PCT No.: PCT/GB2016/053879
§ 371 (c)(1),
(2) Date: Jun. 8, 2018

(87) PCT Pub. No.: WO2017/098254
PCT Pub. Date: Jun. 15, 2017

(65) Prior Publication Data
US 2019/0000848 A1   Jan. 3, 2019

(30) Foreign Application Priority Data
Dec. 10, 2015   (GB) .................................. 1521751

(51) Int. Cl.
| | | |
|---|---|---|
| A61K 31/506 | (2006.01) | |
| A61K 31/4439 | (2006.01) | |
| A61K 31/4196 | (2006.01) | |
| C07C 43/315 | (2006.01) | |
| C07D 307/94 | (2006.01) | |
| A61P 29/02 | (2006.01) | |
| A61K 45/06 | (2006.01) | |
| C07D 401/14 | (2006.01) | |
| C07D 403/04 | (2006.01) | |
| C07D 405/14 | (2006.01) | |

(52) U.S. Cl.
CPC ........ *A61K 31/506* (2013.01); *A61K 31/4196* (2013.01); *A61K 31/4439* (2013.01); *A61K 45/06* (2013.01); *A61P 29/02* (2018.01); *C07C 43/315* (2013.01); *C07D 307/94* (2013.01); *C07D 401/14* (2013.01); *C07D 403/04* (2013.01); *C07D 405/14* (2013.01)

(58) Field of Classification Search
CPC ...... A61K 31/506; A61P 29/02; C07D 405/14
See application file for complete search history.

(56) References Cited

U.S. PATENT DOCUMENTS

| | | | | |
|---|---|---|---|---|
| 9,133,175 B2 * | 9/2015 | Alvaro | .................. | C07D 405/12 |
| 9,346,790 B2 * | 5/2016 | Alvaro | .................. | C07D 405/12 |
| 10,098,881 B2 * | 10/2018 | Alvaro | .................. | C07D 405/12 |

FOREIGN PATENT DOCUMENTS

| | | |
|---|---|---|
| WO | 2011069951 A1 | 6/2011 |
| WO | 2012076877 A1 | 6/2012 |
| WO | 2012168710 A1 | 12/2012 |
| WO | 2013083994 A1 | 6/2013 |
| WO | 2013175211 A1 | 11/2013 |
| WO | 2013175215 A1 | 11/2013 |
| WO | 2013182850 A1 | 12/2013 |
| WO | 2013182851 A1 | 12/2013 |

OTHER PUBLICATIONS

Lian et al. Phytother Res, Sep. 27, 2013, (1321-7).*
Ritter DM, Ho C, O'Leary ME, Covarrubias M. Modulation of Kv3.4 channel N-type inactivation by protein kinase C shapes the action potential in dorsal root ganglion neurons. J. Physiol. 2012; 590(Pt 1):145-61.
Chien LY, Cheng JK, Chu D, Cheng CF, Tsaur ML. Reduced expression of A-type potassium channels in primary sensory neurons induces mechanical hypersensitivity. J. Neurosci., 2007;27(37):9855-65.
Brooke RE, Atkinson L, Batten TF, Deuchars SA, Deuchars J. Association of potassium channel Kv3.4 subunits with pre- and post-synaptic structures in brainstem and spinal cord. Neuroscience 2004;126(4):1001-10.
Ritter DM, Zemel BM, Hala TJ, O'Leary ME, Lepore AC, Covarrubias M. Dysregulation of Kv3.4 channels in dorsal root ganglia following spinal cord injury. J. Neurosci. Jan. 2015;35(3):1260-73.
McCarberg BH, Nicholson BD, Todd KH, Palmer T, Penles L. The impact of pain on quality of life and the unmet needs of pain management: results from pain sufferers and physicians participating in an Internet survey. Am. J. Ther. Jul. Aug. 2008;15(4):312-20.
Woolf CJ. What is this thing called pain? J. Clin. Invest. Nov. 2010;120(11):3742-4.
Finnerup NB, et al., Pharmacotherapy for neuropathic pain in adults: systematic review, meta-analysis and updated NeuPSIG recommendations. Lancet Neurol. Feb. 2015;14(2):162-73.
Bennett DL, Woods CG. Painful and painless channelopathies. Lancet Neurol. Jun. 2014;13(6):587-99.
Sun S, Cohen CJ, Dehnhardt CM. Inhibitors of voltage-gated sodium channel Nav1.7: patent applications since 2010. Pharm. Pat. Anal. Sep. 2014;3(5):509-21.

(Continued)

*Primary Examiner* — Kamal A Saeed
(74) *Attorney, Agent, or Firm* — McDermott Will & Emery LLP

(57) ABSTRACT

The present invention provides a modulator of Kv3.1 and/or Kv3.2 and/or Kv3.3 channels for use in the prophylaxis or treatment of pain. Modulators for use in the prophylaxis or treatment of pain include compounds of formula (I) or a pharmaceutically acceptable salt and/or solvate thereof and/or derivative thereof: (I).

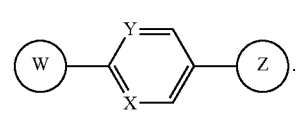

11 Claims, 27 Drawing Sheets

(56) References Cited

OTHER PUBLICATIONS

Dib-Hajj SD, Yang Y, Black JA, Waxman SG. The NaV1.7 sodium channel: from molecule to man. Nat. Rev. Neurosci. Jan. 2013;14(1):49-62.

Zamponi GW, Striessnig J, Koschak A, Dolphin AC. The Physiology, Pathology, and Pharmacology of Voltage-Gated Calcium Channels and Their Future Therapeutic Potential. Pharmacol Rev. Oct. 2015;67(4):821-70.

Devulder J. Flupirtine in pain management: pharmacological properties and clinical use. CNS Drugs Oct. 2010;24 (10):867-81.

Wickenden AD, McNaughton-Smith G. Kv7 channels as targets for the treatment of pain. Curr. Pharm. Des. 2009;15 (15):1773-98.

Lu R, Bausch AE, Kallenborn-Gerhardt W, Stoetzer C, Debruin N, Ruth P, Geisslinger G, Leffler A, Lukowski R, Schmidtko A. Slack channels expressed in sensory neurons control neuropathic pain in mice. J. Neurosci. Jan. 2015;35(3):1125-35.

Baranauskas G, Nistri A. Sensitization of pain pathways in the spinal cord: cellular mechanisms. Prog. Neurobiol. Feb. 1998;54(3):349-65.

Cervero F. Spinal cord hyperexcitability and its role in pain and hyperalgesia. Exp. Brain Res. Jun. 2009;196 (1):129-37.

Woolf CJ. Central sensitization: Implications for the diagnosis and treatment of pain. Pain, Mar. 2011;152(3 Suppl): S2-15.

Baron R, Hans G, Dickenson AH. Peripheral input and its importance for central sensitization. Ann. Neurol. Nov. 2013;74(5):630-6.

Deuchars SA, Brooke RE, Frater B, Deuchars J. Properties of interneurones in the intermediolateral cell column of the rat spinal cord: role of the potassium channel subunit Kv3.1. Neuroscience 2001;106(2):433-46.

Brooke RE, Pyner S, McLeish P, Buchan S, Deuchars J, Deuchars SA. Spinal cord interneurons labelled transneuronally from the adrenal gland by a GFP-herpes virus construct contain the potassium channel subunit Kv3.1b. Auton. Neurosci. Jun. 2002;98(1-2):45-50.

Brooke RE, Atkinson L, Edwards I, Parson SH, Deuchars J. Immunohistochemical localisation of the voltage gated potassium ion channel subunit Kv3.3 in the rat medulla oblongata and thoracic spinal cord. Brain Res. Jan. 2006;1070 (1):101-15.

International Search Report and Written Opinion from corresponding international application PCT/GB2016/053879 dated Feb. 24, 2017 (7 pages).

Attali, B., et al., "Voltage-gated potassium channels (version 2019.4)" in the IUPHAR/BPS Guide to Pharmacology Database. IUPHAR/BPS Guide to Pharmacology CITE. 2019; 2019(4). Available from: https://doi.org/10.2218/gtopdb/F81/2019.4.

ClinicalTrials.gov Identifier: NCT02435342, A 4 Week Study of the Safety, Tolerability and Pharmacodynamics of ShK-186 (Dalazatide) in Active Plaque Psoriasis, First posted May 6, 2015; Available from: https://www.clinicaltrials.gov/ct2/show/NCT02435342?term=NCT02435342&draw=2&rank=1—last retrieved on Aug. 12, 2020; 7 pgs.

ClinicalTrials.gov Identifier: NCT02446340, Multiple Ascending Dose Safety Study of ShK-186 (Dalazatide) in Healthy Volunteers, First posted May 18, 2015; Available from: https://www.clinicaltrials.gov/ct2/show/study/NCT02446340?term=NCT02446340&draw=2&rank=1—last retrieved on Aug. 12, 2020; 7 pgs.

Rudy B, et al., "Kv3 channels: voltage-gated K+ channels designed for high-frequency repetitive firing." (2001) Trend Neurosci. 24(9):517-26.

Tabeshpour, J, et al. "Effects of curcumin on ion channels and pumps: A review." (2019) IUBMB Life 71 (7):812-820.

Tarcha, EJ., et al., "Durable pharmacological responses from the peptide ShK-186, a specific Kv1.3 channel inhibiton that suppresses T cell mediators of autoimmune disease." (2012) J Pharmacol Exp Ther. 342(3):642-53.

Wulff, H, et al., "Potassium channels as therapeutic targets for autoimmune disorders." (2003) Curr Opin Drug Discovery Devel. 6(5):640-7.

Zhao, Y, et al., "Toxins Targeting the Kv1.3 Channel: Potential Immunomodulators for Autoimmune Diseases." (2015) Toxins (Basel). 7(5)1749-64.

\* cited by examiner

MODULATORS OF KV3 CHANNELS TO TREAT PAIN

RELATED APPLICATIONS

This application is the U.S. National Stage of International Application No. PCT/GB2016/053879, filed Dec. 9, 2016, published in English, and claims the benefit of United Kingdom Patent Application No. GB 1521751.6, filed on Dec. 10, 2015, the entire teachings of the above applications are incorporated herein by reference.

TECHNICAL FIELD

This invention relates to compounds and pharmaceutical compositions containing such compounds for use in the prophylaxis or treatment of pain, and to related methods and uses.

BACKGROUND TO THE INVENTION

The Kv3 voltage-gated potassium channel family includes four members, Kv3.1, Kv3.2, Kv3.3, and Kv3.4. Genes for each of these subtypes can generate multiple isoforms by alternative splicing, producing versions with different C-terminal domains. Thirteen isoforms have been identified in mammals to date, but the currents expressed by these variants appear similar (Rudy et al., 2001). Kv3 channels are activated by depolarisation of the plasma membrane to voltages more positive than −20 mV; furthermore, the channels deactivate rapidly upon repolarisation of the membrane. These biophysical properties ensure that the channels open towards the peak of the depolarising phase of the neuronal action potential to initiate repolarisation. Rapid termination of the action potential mediated by Kv3 channels allows the neuron to recover more quickly to reach sub-threshold membrane potentials from which further action potentials can be triggered. As a result, the presence of Kv3 channels in certain neurons contributes to their ability to fire at high frequencies (Rudy et al., 2001). Kv3.1-Kv3.3 subtypes are predominant in the CNS, whereas Kv3.4 channels are found predominantly in skeletal muscle and sympathetic neurons (Weiser et al., 1994). Kv3.1-Kv3.3 channel subtypes are differentially expressed by sub-classes of interneurons in cortical and hippocampal brain areas (e.g. Chow et al., 1999; Martina et al., 1998; McDonald et al., 2006; Chang et al., 2007), in the thalamus (e.g. Kasten et al., 2007), cerebellum (Sacco et al., 2006; Puente et al., 2010), and auditory brain stem nuclei (Li et al., 2001).

Kv3 channels are important determinants of the function of the cerebellum, a region of the brain important for motor control (Joho et al., 2009). Characterisation of mice in which one or more of the Kv3 subtypes has been deleted shows that the absence of Kv3.1 gives rise to increased locomotor activity, altered electroencephalographic activity, and a fragmented sleep pattern (Joho et al., 1999). The deletion of Kv3.2 leads to a reduction in seizure threshold and altered cortical electroencephalographic activity (Lau et al., 2000). Deletion of Kv3.3 is associated with mild ataxia and motor deficits (McMahon et al., 2004). Double deletion of Kv3.1 and Kv3.3 gives rise to a severe phenotype characterised by spontaneous seizures, ataxia, and an increased sensitivity to the effects of ethanol (Espinosa et al., 2001; Espinosa et al., 2008).

The known pharmacology of Kv3 channels is limited. Tetraethylammonium (TEA) has been shown to inhibit the channels at low millimolar concentrations (Rudy et al., 2001), and blood-depressing substance (BDS) toxins from the sea anemone, *Anemonia sulcata* (Diochot et al., 1998), have been shown to selectively inhibit Kv3 channels with high affinity (Yeung et al., 2005). In addition to compounds acting directly on Kv3 channels, agonists of receptors that activate protein kinase A (PKA) and protein kinase C (PKC) have been shown to modulate Kv3-mediated currents in specific brain areas, leading to a reduction in the ability of the neurons to fire at high frequency (Atzori et al., 2000; Song et al., 2005); these studies suggest that PKA and PKC can specifically phosphorylate Kv3 channels in a neuron-specific manner, causing a reduction in Kv3-mediated currents.

Patent applications WO2011/069951, WO2012/076877, WO2012/168710, WO2013/175215, WO2013/083994 and WO2013/182850 disclose compounds which are modulators of Kv3 channels, specifically Kv3.1, Kv3.2 and Kv3.3. Use of such compounds in certain diseases and disorders requiring modulation of Kv3 channels are disclosed in patent applications WO2013/182851 and WO2013/175211.

In the broadest sense, pain can be grouped in to acute pain and chronic pain. Acute pain is defined as pain that is self-limited and generally requires treatment for no more than up to a few weeks, for example postoperative or acute musculoskeletal pain, such as fractures (US Food and Drug Administration, 2014). Chronic pain can be defined either as pain persisting for longer than 1 month beyond resolution of the initial trauma, or pain persisting beyond three months. There is often no clear cause of chronic pain, and a multitude of other health problems such as fatigue, depression, insomnia, mood changes and reduction in movement, often accompany chronic pain.

Chronic pain can be sub-divided in to the following groups: neuropathic pain, chronic musculoskeletal pain and miscellaneous chronic pain. Neuropathic pain usually accompanies tissue injury and is initiated or caused by damage to the nervous system (peripheral nervous system and/or central nervous system), such as amputation, stroke, diabetes, or multiple sclerosis. Chronic musculoskeletal pain can be a symptom of diseases such as osteoarthritis and chronic lower back pain and can occur following damage to muscle tissue as well as trauma to an area, for example, fractures, sprains and dislocation. Miscellaneous chronic pain encompasses all other types of long term pain and includes non-neuropathic pain conditions such as cancer pain and fibromyalgia as well as headaches and tendinitis.

Chronic pain is a highly heterogeneous condition that remains amongst the most troublesome and difficult to manage of clinical indications (McCarberg et al., 2008; Woolf 2010; Finnerup et al., 2015). Despite years of research and drug development, there has been little progress in identifying treatments that can match the opioids for efficacy without significant side effects and risk of dependence. Voltage-gated ion channels have been important targets for the management of specific pain indications, in particular neuropathic pain states. Furthermore, genetic mutations in specific ion channels have been linked to some chronic pain disorders (Bennett et al., 2014). Examples of voltage-gated ion channels that are being explored as pharmaceutical targets include:

Sodium channels (in particular NaV1.7)—Sun et al., 2014; Dib-Hajj et al., 2013
N-type calcium channels—Zamponi et al., 2015
Kv7 potassium channels—Devulder 2010; Wickenden et al., 2009
SLACK—Lu et al., 2015

The basic hypothesis underlying these approaches is that chronic pain states are associated with increased excitability and/or aberrant firing of peripheral sensory neurons, in particular neurons involved in the transmission of painful sensory stimuli, such as the C-fibres of the dorsal root ganglia and specific circuits within the spinal cord (Baranauskas et al., 1998; Cervero 2009; Woolf et al., 2011; Baron et al., 2013). Animal models of neuropathic and inflammatory chronic pain provide the main support for this hypothesis, although demonstration of causality is still lacking (Cervero 2009).

Drugs targeting hyperexcitability, such as sodium channel blockers (e.g. CNV1014802, lamotrigine, carbamazepine, and local anaesthetics), Kv7 positive modulators (e.g. flupertine and retigabine), and N-type calcium channel modulators (e.g. gabapentin, which interacts with the α2δ subunit of the N-type calcium channel, and ziconitide, derived from a cone snail toxin) show efficacy in models of inflammatory and/or neuropathic pain. However, amongst these drugs, there is mixed evidence for clinical efficacy, for example, balancing efficacy and increased burden of side effects on the central nervous system. The disparity between efficacy in animal models and efficacy in humans is likely to be due to a range of factors, but in particular, drug concentration achievable in humans (due to poor tolerability) and heterogeneity of human pain conditions are likely to be the main culprits.

A further target of interest is SLACK. Preclinical rationale supports good potential efficacy (Lu et al., 2015), although to date, there is a lack of selective compounds which makes it difficult to determine which pain states might be most receptive.

Improving the pharmacological management of pain is focused on mechanisms that can deliver good efficacy with a reduced side-effect burden, reduced tolerance or tachyphylaxis, and reduced abuse liability and/or risk of dependence.

Recently, Kv3.4 channels have become a target of interest for the treatment of chronic pain. Kv3.4 channels are expressed on neurons of the dorsal root ganglia (Ritter et al., 2012; Chien et al., 2007), where they are predominantly expressed on sensory C-fibres (Chien et al., 2007).

Kv3 channels are also expressed by specific subsets of neurons in the spinal cord. Specifically, Kv3.1b (Deuchars et al., 2001; Brooke et al., 2002), Kv3.3 (Brooke et al., 2006), and Kv3.4 subunits (Brooke et al., 2004) have been identified in rodent spinal cord, although not always in association with circuits involved with sensory processing.

Recent animal model data suggest a down-regulation of Kv3.4 channel surface expression in DRG neurons following spinal cord injury associated with hypersensitivity to painful stimuli (Ritter et al., 2015). Similarly, it has been observed that there is a down-regulation of Kv3.4 expression in DRGs of rodents following spinal cord ligation (Chien et al., 2007). This latter study also showed that intrathecal administration to rats of an antisense oligonucleotide to suppress the expression of Kv3.4 led to hypersensitivity to mechanical stimuli. It has been shown that Kv3.4 channel inactivation could be influenced by protein kinase C-dependent phosphorylation of the channels, and that this physiological mechanism might allow DRG neurons to alter their firing characteristics in response to painful stimuli (Ritter et al., 2012).

These studies suggest a causal relationship between the emergence of mechanical allodynia and reduced Kv3.4 channel expression or function. No evaluation of Kv3.1, Kv3.2, or Kv3.3 expression in SC or DRG neurons was conducted in any of these studies, and expression of these three subtypes has not been explicitly demonstrated on DRG neurons (although as mentioned above, they are abundant within specific regions of the spinal cord).

The in vivo studies reported above provide a rationale for modulation of Kv3.4 as a novel approach to the treatment of certain neuropathic pain states. There are currently no data specifically linking Kv3.1 and/or Kv3.2 and/or Kv3.3 channel subtypes to pain processing.

There remains a need for the identification of alternative modulators for the prophylaxis or treatment of pain which may display one or more of the following desirable properties:
improved efficacy;
improved potency;
more convenient administration regimes;
reduced side-effect burden;
reduced tolerance or tachyphylaxis; and
reduced abuse liability and/or risk of dependence.

The present inventors have found that surprisingly, modulation of Kv3.1 and/or Kv3.2 and/or Kv3.3 channels is linked to the processing of pain and pain control. Therefore, modulation of Kv3.1 and/or Kv3.2 and/or Kv3.3 represents a new approach for the prophylaxis or treatment of pain.

SUMMARY OF THE INVENTION

The present invention provides a modulator of Kv3.1 and/or Kv3.2 and/or Kv3.3 channels (referred to herein as "Kv3.1/Kv3.2/Kv3.3" or "Kv3.1 and/or Kv3.2 and/or Kv3.3") for use in the prophylaxis or treatment of pain.

The present invention further provides the use of a modulator of Kv3.1 and/or Kv3.2 and/or Kv3.3 channels in the manufacture of a medicament for the prophylaxis or treatment of pain.

The present invention also provides a method of prophylaxis or treatment of pain by administering a modulator of Kv3.1 and/or Kv3.2 and/or Kv3.3 channels.

Suitably, the modulator is a compound of formula (I) or a pharmaceutically acceptable salt and/or solvate thereof and/or derivative thereof:

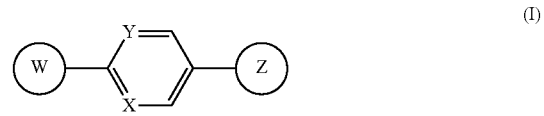

wherein:
W is group (Wa), group (Wb), group (Wc) or group (Wd):

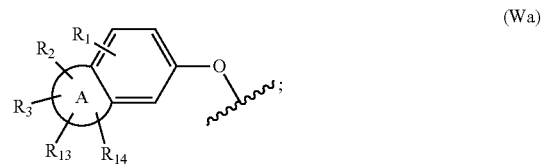

wherein:
R$_1$ is H, C$_{1-4}$alkyl, halo, haloC$_{1-4}$alkyl, CN, C$_{1-4}$alkoxy, or haloC$_{1-4}$alkoxy;
R$_2$ is H, C$_{1-4}$alkyl, C$_{3-5}$ spiro carbocyclyl, haloC$_{1-4}$alkyl or halo;
R$_3$ is H, C$_{1-4}$alkyl, haloC$_{1-4}$alkyl, halo; or R$_3$ is absent;
R$_{13}$ is H, C$_{1-4}$alkyl, haloC$_{1-4}$alkyl, halo; or R$_{13}$ is absent;
R$_{14}$ is H, C$_{1-4}$alkyl, haloC$_{1-4}$alkyl, halo; or R$_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
wherein R$_2$ and R$_3$ may be attached to the same or a different ring atom; R$_2$ may be attached to a fused ring atom; and wherein R$_{13}$ and R$_{14}$ may be attached to the same or a different ring atom;

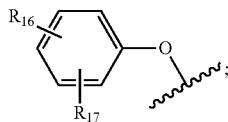

(Wc)

wherein:
R$_{16}$ is halo, C$_{1-4}$ alkyl, C$_{1-4}$alkoxy, halo-C$_{1-4}$alkyl, halo-C$_{1-4}$alkoxy, or CN;
R$_{17}$ is H, halo, cyano, C$_{1-4}$ alkyl or C$_{1-4}$ alkoxy; with the proviso that when R$_{17}$ is H,
R$_{16}$ is not in the para position;

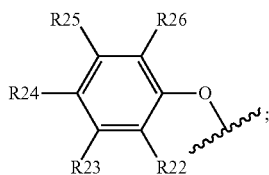

(Wd)

wherein:
R$_{22}$ is H, Cl, F or C$_{1-4}$alkyl;
R$_{23}$ is H, C$_{1-4}$alkyl, Cl, CF$_3$, O—C$_{1-4}$alkyl, OCF$_3$ or N(CH$_3$)$_2$;
R$_{24}$ is H, Cl, F, C$_{1-4}$alkyl, O—C$_{1-4}$alkyl, CN, OCF$_3$ or CF$_3$;
R$_{25}$ is H, Cl, F, O—C$_{1-4}$alkyl or C$_{1-4}$alkyl; and
R$_{26}$ is H or C$_{1-4}$alkyl;
  wherein for R$_{22}$ to R$_{26}$, C$_{1-4}$alkyl may be substituted by O-methyl;
  with the provisos that:
    not all of R$_{22}$ to R$_{26}$ may be H;
    when R$_4$ is H, then R$_{23}$ is methyl or CF$_3$ and R$_{22}$, R$_{24}$, R$_{25}$ and R$_{26}$ are all H;
    when one of R$_{22}$, R$_{24}$, R$_{25}$ or R$_{26}$ is F, then at least one of R$_{22}$ to R$_{26}$ cannot be H or F; and
    when R$_{24}$ is not H, at least one of R$_{22}$ or R$_{23}$ is not H;
X is CH or N;
Y is CR$_{15}$ or N;

R$_{15}$ is H or C$_{1-4}$alkyl;
when W is group (Wa), group (Wb) or group (Wc), Z is group (Za):

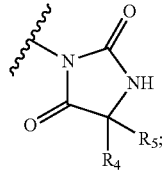

(Za)

wherein:
R$_4$ is C$_{1-4}$ alkyl;
R$_5$ is H or C$_{1-4}$ alkyl;
or R$_4$ and R$_5$ can be fused to form C$_{3-4}$ spiro carbocyclyl;
when W is group (Wa), group (Wb) or group (Wd), Z is group (Zb):

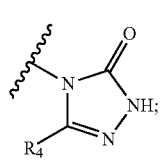

(Zb)

wherein:
R$_4$ is H or C$_{1-4}$ alkyl.

The compounds of formula (I) may be used as medicaments, in particular for the prophylaxis or treatment of pain, such as neuropathic or inflammatory pain.

Additionally provided is a method of identifying that a compound is of use in the prophylaxis or treatment of pain, said method comprising the step of determining that the compound is a modulator of Kv3.1 and/or Kv3.2 and/or Kv3.3 channels.

Also provided is a method for the manufacture of a pain medicament, said method comprising the steps: (i) determining that a compound is a modulator of Kv3.1 and/or Kv3.2 and/or Kv3.3 channels and (ii) preparing a medicament comprising the compound. The pain medicament may be for the prophylaxis or treatment of pain.

DETAILED DESCRIPTION OF THE INVENTION

Figure 1A:
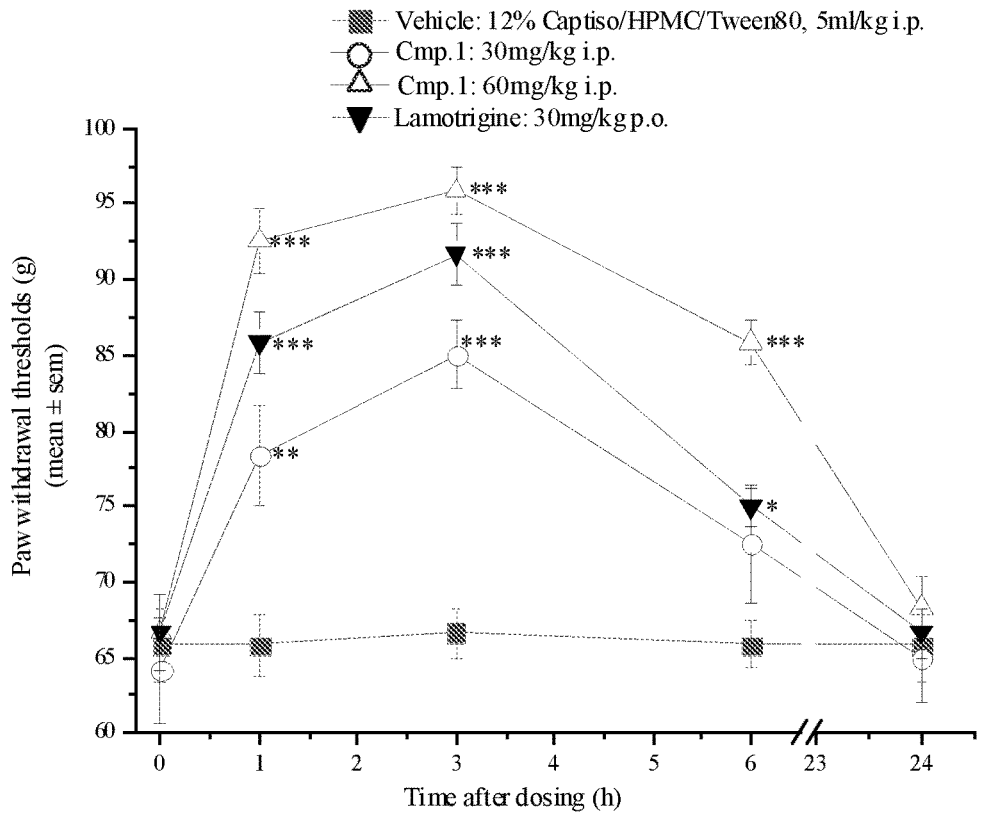
FIG. 1 shows the effect of Compound 1 on paw withdrawal thresholds under mechanical pressure in a neuropathic pain model (Study 1): ipsilateral paw (FIG. 1a); contralateral paw (FIG. 1b); and percentage reversals (FIG. 1c).

The present invention provides a modulator of Kv3.1 and/or Kv3.2 and/or Kv3.3 channels for use in the prophylaxis or treatment of pain.

The present invention further provides the use of a modulator of Kv3.1 and/or Kv3.2 and/or Kv3.3 channels in the manufacture of a medicament for the prophylaxis or treatment of pain.

The present invention also provides a method of prophylaxis or treatment of pain by administering a modulator of Kv3.1 and/or Kv3.2 and/or Kv3.3 channels.

Suitably, the modulator is a compound of formula (I) or a pharmaceutically acceptable salt and/or solvate thereof and/or derivative thereof:

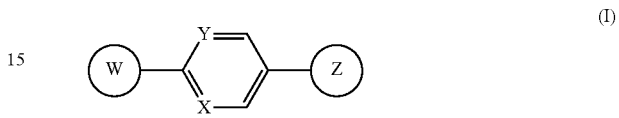

(I)

wherein:
W is group (Wa), group (Wb), group (Wc) or group (Wd):

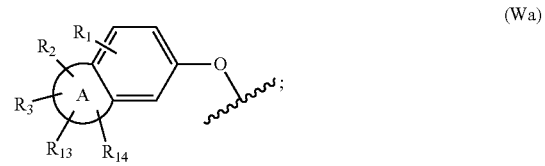

(Wa)

(Wb)

wherein:
R$_1$ is H, C$_{1-4}$alkyl, halo, haloC$_{1-4}$alkyl, CN, C$_{1-4}$alkoxy, or haloC$_{1-4}$alkoxy;
R$_2$ is H, C$_{1-4}$alkyl, C$_{3-5}$ spiro carbocyclyl, haloC$_{1-4}$alkyl or halo;
R$_3$ is H, C$_{1-4}$alkyl, haloC$_{1-4}$alkyl, halo; or R$_3$ is absent;
R$_{13}$ is H, C$_{1-4}$alkyl, haloC$_{1-4}$alkyl, halo; or R$_{13}$ is absent;
R$_{14}$ is H, C$_{1-4}$alkyl, haloC$_{1-4}$alkyl, halo; or R$_{14}$ is absent;
A is a 5 or 6 membered saturated or unsaturated heterocycle, with at least one O atom; which heterocycle is optionally fused with a cyclopropyl group, or a cyclobutyl group, or a cyclopentyl group to form a tricycle when considered together with the phenyl;
wherein R$_2$ and R$_3$ may be attached to the same or a different ring atom; R$_2$ may be attached to a fused ring atom; and wherein R$_{13}$ and R$_{14}$ may be attached to the same or a different ring atom;

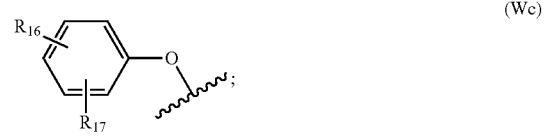

(Wc)

wherein:
R$_{16}$ is halo, C$_{1-4}$ alkyl, C$_{1-4}$alkoxy, halo-C$_{1-4}$alkyl, halo-C$_{1-4}$alkoxy, or CN;
R$_{17}$ is H, halo, cyano, C$_{1-4}$ alkyl or C$_{1-4}$ alkoxy; with the proviso that when R$_{17}$ is H,
R$_{16}$ is not in the para position;

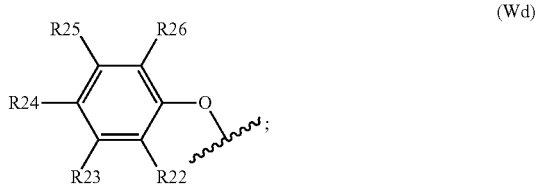

(Wd)

wherein:
R$_{22}$ is H, Cl, F or C$_{1-4}$alkyl;
R$_{23}$ is H, C$_{1-4}$alkyl, Cl, CF$_3$, O—C$_{1-4}$alkyl, OCF$_3$ or N(CH$_3$)$_2$;
R$_{24}$ is H, Cl, F, C$_{1-4}$alkyl, O—C$_{1-4}$alkyl, CN, OCF$_3$ or CF$_3$;
R$_{25}$ is H, Cl, F, O—C$_{1-4}$alkyl or C$_{1-4}$alkyl; and
R$_{26}$ is H or C$_{1-4}$alkyl;
  wherein for R$_{22}$ to R$_{26}$, C$_{1-4}$alkyl may be substituted by O-methyl;
  with the provisos that:
    not all of R$_{22}$ to R$_{26}$ may be H;
    when R$_4$ is H, then R$_{23}$ is methyl or CF$_3$ and R$_{22}$, R$_{24}$, R$_{25}$ and R$_{26}$ are all H;
    when one of R$_{22}$, R$_{24}$, R$_{25}$ or R$_{26}$ is F, then at least one of R$_{22}$ to R$_{26}$ cannot be H or F; and
    when R$_{24}$ is not H, at least one of R$_{22}$ or R$_{23}$ is not H;
X is CH or N;
Y is CR$_{15}$ or N;
R$_{15}$ is H or C$_{1-4}$alkyl;
when W is group (Wa), group (Wb) or group (Wc), Z is group (Za):

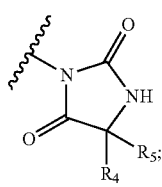

(Za)

wherein:
R$_4$ is C$_{1-4}$ alkyl;
R$_5$ is H or C$_{1-4}$ alkyl;
or R$_4$ and R$_5$ can be fused to form C$_{3-4}$ spiro carbocyclyl;
when W is group (Wa), group (Wb) or group (Wd), Z is group (Zb):

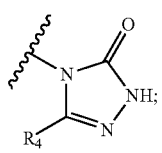

(Zb)

wherein:
R$_4$ is H or C$_{1-4}$ alkyl.

The compounds of formula (I) may be used as medicaments, in particular for the prophylaxis or treatment of pain, such as neuropathic or inflammatory pain.

In one embodiment on the invention, the modulator is a compound of formula (IA):

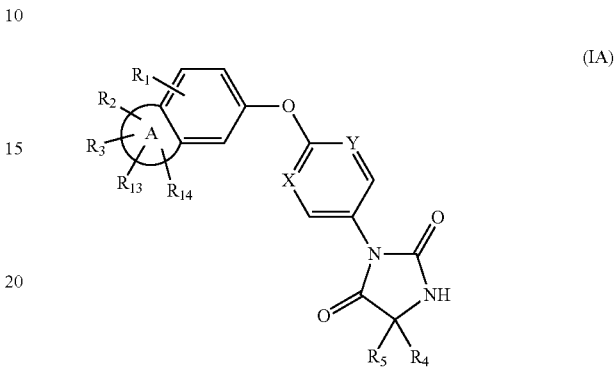

(IA)

wherein R$_1$, R$_2$, R$_3$, R$_{13}$, R$_{14}$, A, X, Y, R$_4$ and R$_5$ are as defined above for compounds for formula (I).

In one embodiment on the invention, the modulator is a compound of formula (IB):

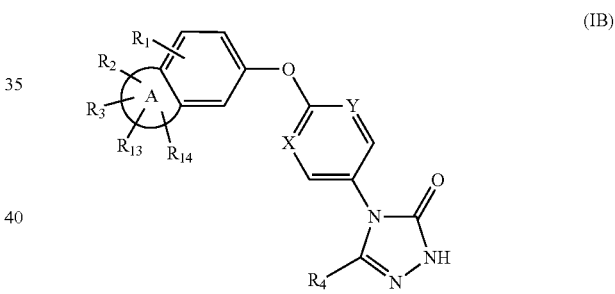

(IB)

wherein R$_1$, R$_2$, R$_3$, R$_{13}$, R$_{14}$, A, X, Y and R$_4$ are as defined above for compounds for formula (I).

In one embodiment on the invention, the modulator is a compound of formula (IC):

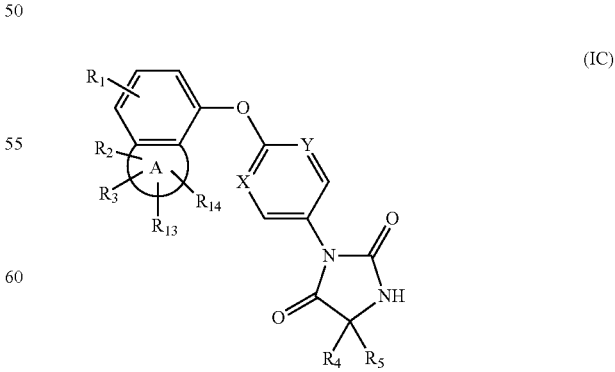

(IC)

wherein R$_1$, R$_2$, R$_3$, R$_{13}$, R$_{14}$, A, X, Y, R$_4$ and R$_5$ are as defined above for compounds for formula (I).

In one embodiment on the invention, the modulator is a compound of formula (ID):

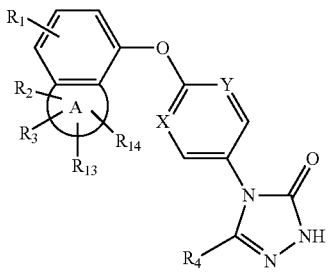

(ID)

wherein $R_1$, $R_2$, $R_3$, $R_{13}$, $R_{14}$, A, X, Y and $R_4$ are as defined above for compounds for formula (I).

In one embodiment on the invention, the modulator is a compound of formula (IE):

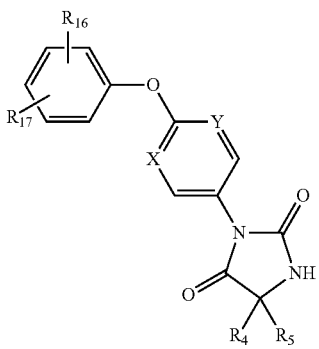

(IE)

wherein $R_{16}$ and $R_{17}$, X, Y, $R_4$ and $R_5$ are as defined above for compounds for formula (I).

In one embodiment on the invention, the modulator is a compound of formula (IF):

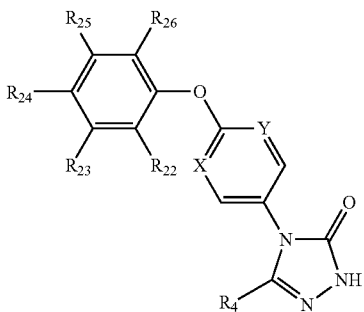

(IF)

wherein $R_{22}$, $R_{23}$, $R_{24}$, $R_{25}$, $R_{26}$, X, Y and $R_4$ are as defined above for compounds for formula (I).

Suitably, $R_1$ is H, $C_{1-4}$alkyl, halo or halo$C_{1-4}$alkyl. In another embodiment of the invention $R_1$ is H or methyl. In one embodiment of the invention $R_1$ is H. In another embodiment of the invention $R_1$ is $C_{1-4}$alkyl, in particular methyl. When W is group (Wa), suitably $R_1$ is H. When W is group (Wb), suitably $R_1$ is H or methyl.

When W is group (Wb), suitably $R_1$ is positioned at the para position of the phenyl ring, as illustrated below:

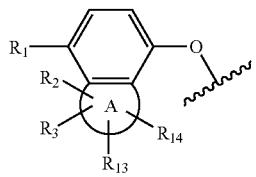

Suitably $R_2$ is H, $C_{1-4}$alkyl, $C_{3-5}$spiro carbocyclyl, or halo$C_{1-4}$alkyl. In one embodiment of the invention $R_2$ is $C_{1-4}$alkyl, in particular methyl, ethyl, isopropyl, tert-butyl or cyclopropyl, especially methyl, ethyl, isopropyl or tert-butyl. In one embodiment of the invention $R_2$ is $C_{3-5}$spiro carbocyclyl. In one embodiment of the invention $R_2$ is $C_3$spiro carbocyclyl. In another embodiment of the invention $R_2$ is $C_4$ spiro carbocyclyl. In a further embodiment of the invention $R_2$ is $C_5$spiro carbocyclyl. In one embodiment of the invention $R_2$ is halo$C_{1-4}$alkyl, in particular trifluoromethyl or 2,2,2-trifluoroethyl. In one embodiment of the invention $R_2$ is halo, in particular fluoro. In another embodiment of the invention $R_2$ is H.

In one embodiment of the invention $R_3$ is H, $C_{1-4}$alkyl, halo$C_{1-4}$alkyl or halo. Alternatively, $R_3$ is H, $C_{1-4}$alkyl, or halo$C_{1-4}$alkyl. Suitably $R_3$ is H or $C_{1-4}$alkyl. In one embodiment of the invention $R_3$ is H. In one embodiment of the invention $R_3$ is $C_{1-4}$alkyl, in particular methyl, ethyl, isopropyl, tert-butyl or cyclopropyl, especially methyl, ethyl, isopropyl or tert-butyl, such as methyl or ethyl. In one embodiment of the invention, $R_3$ is halo$C_{1-4}$alkyl, in particular trifluoromethyl or 2,2,2-trifluoroethyl. In one embodiment of the invention $R_3$ is halo, in particular fluoro. The skilled person will appreciate that, depending on the size, presence of heteroatoms and the degree of unsaturation of the A ring, $R_3$ may be absent. Consequently, in another embodiment of the invention $R_3$ is absent. Suitably $R_3$ is H, methyl or trifluoromethyl.

In one embodiment of the invention $R_2$ may be H, $C_{1-4}$alkyl, halo$C_{1-4}$alkyl or $C_{3-5}$spiro carbocyclyl and $R_3$ may be H, $C_{1-4}$alkyl, or halo$C_{1-4}$alkyl. In a particular embodiment of the invention, $R_2$ may be methyl, ethyl, isopropyl, tert-butyl, cyclopropyl, $C_{3-5}$spiro carbocyclyl, trifluoromethyl or 2,2,2-trifluoroethyl and $R_3$ may be H, methyl, ethyl or trifluoromethyl. In certain embodiments of the invention $R_3$ is H and $R_2$ is H, methyl, ethyl, isopropyl or $C_3$-4spiro carbocyclyl. In further embodiments of the invention $R_3$ and $R_2$ are both fluoro (such as attached to the same ring carbon atom). In one embodiment of the invention $R_2$ is $C_{1-4}$alkyl and $R_3$ is H, for example $R_2$ is methyl, ethyl, tert-butyl or cyclopropyl. In one embodiment of the invention $R_2$ is $C_{1-4}$alkyl and $R_3$ is $C_{1-4}$alkyl, for example $R_2$ is methyl and $R_3$ is methyl, $R_2$ is ethyl and $R_3$ is ethyl or $R_2$ is methyl and $R_3$ is ethyl. In another embodiment of the invention $R_2$ is trifluoromethyl and $R_3$ is methyl.

In one embodiment of the invention $R_2$ and $R_3$ are attached to the same ring atom. In an alternative embodiment of the invention $R_2$ and $R_3$ are attached to different ring atoms.

In one embodiment of the invention $R_{13}$ is H, F or methyl. In one embodiment of the invention $R_{13}$ is H. In another embodiment of the invention $R_{13}$ is $C_{1-4}$alkyl, in particular methyl. In a further embodiment of the invention $R_{13}$ is halo, in particular fluoro. In an additional embodiment of the invention $R_{13}$ is halo$C_{1-4}$alkyl, such as trifluoromethyl. The skilled person will appreciate that, depending on the size, presence of heteroatoms and the degree of unsaturation of the A ring, $R_{13}$ may be absent. Consequently, in another embodiment of the invention $R_{13}$ is absent.

In one embodiment of the invention $R_{14}$ is H, F or methyl. In one embodiment of the invention $R_{14}$ is H. in another embodiment of the invention $R_{14}$ is $C_{1-4}$alkyl, in particular methyl. In a further embodiment of the invention $R_{14}$ is halo, in particular fluoro. In an additional embodiment of the invention $R_{13}$ is haloC$_{1-4}$alkyl, such as trifluoromethyl. The skilled person will appreciate that, depending on the size, presence of heteroatoms and the degree of unsaturation of the A ring, $R_{14}$ may be absent. Consequently, in another embodiment of the invention $R_{14}$ is absent.

In one embodiment of the invention $R_{13}$ and $R_{14}$ are attached to the same ring atom. In an alternative embodiment of the invention $R_{13}$ and $R_{14}$ are attached to different ring atoms.

In certain embodiments of the invention $R_2$, $R_3$, $R_{13}$ and $R_{14}$ are each independently selected from H, $C_{1-4}$alkyl, haloC$_{1-4}$alkyl and halo, such as H, $C_{1-4}$alkyl and haloC$_{1-4}$alkyl. Suitably $R_2$, $R_3$, $R_{13}$ and $R_{14}$ are each independently selected from H, F, methyl and trifluoromethyl.

Suitably, A is a 5 or 6 membered saturated or unsaturated heterocycle, with at least one O atom; which heterocycle is optionally fused with a cyclopropyl group to form a tricycle when considered together with the phenyl. In one embodiment of the invention A is a 5 membered saturated or unsaturated heterocycle, with at least one O atom; which heterocycle is optionally fused with a cyclopropyl group, a cyclobutyl group or a cyclopentyl group to form a tricycle when considered together with the phenyl. In another embodiment of the invention A is a 6 membered saturated or unsaturated heterocycle, with at least one O atom; which heterocycle is optionally fused with a cyclopropyl group, a cyclobutyl group or a cyclopentyl group to form a tricycle when considered together with the phenyl.

In one embodiment of the invention A is a 5 membered saturated or unsaturated heterocycle with at least one O atom, which heterocycle is fused with a cyclopropyl group to form a tricycle when considered together with the phenyl. In another embodiment of the invention A is a 6 membered saturated or unsaturated heterocycle with at least one O atom, which heterocycle is fused with a cyclopropyl group to form a tricycle when considered together with the phenyl.

In one embodiment of the invention A is a 5 membered saturated or unsaturated heterocycle with at least one O atom. In one embodiment of the invention A is a 6 membered saturated or unsaturated heterocycle with at least one O atom.

In certain embodiments of the invention the ring A contains one heteroatom. In other embodiments of the invention the ring A contains two heteroatoms (e.g. two oxygen atoms, one oxygen atom and one nitrogen atom, or one oxygen atom and one sulphur atom), in particular two oxygen atoms or one oxygen atom and one nitrogen atom.

Suitably, A is dihydrofuran, isoxazole, dihydropyran, 1,3-dioxolane, 1,3-oxazine or dihydropyran fused with a cyclopropyl group.

In one embodiment of the invention A is dihydrofuran. In one embodiment of the invention A is dihydropyran. In another embodiment of the invention A is dihydrofuran fused with a cyclopropyl group, a cyclobutyl group or a cyclopentyl group. In another embodiment of the invention A is dihydropyran fused with a cyclopropyl group, a cyclobutyl group or a cyclopentyl group. In a further embodiment the invention A is dihydrofuran fused with a cyclopropyl group. In still further embodiment the invention A is dihydropyran fused with a cyclopropyl group.

In one embodiment of the invention A is fused with a cyclopropyl group. In another embodiment A is fused with a cyclobutyl group. In a further embodiment of the invention A is fused with a cyclopentyl group. In one embodiment of the invention A is not fused with a cyclopropyl group, a cyclobutyl group or a cyclopentyl group.

In one embodiment of the invention A is dihydrofuran, dihydropyran, furan, pyran, oxazole, isoxazole, oxazine, dioxine or 1,3-dioxalane. In another embodiment A is dihydrofuran, dihydropyran or 1,3-dioxalane.

In one embodiment of the invention A is:

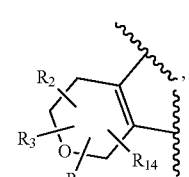

1

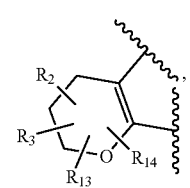

2

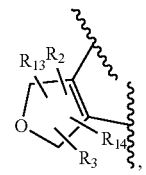

3

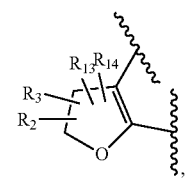

4

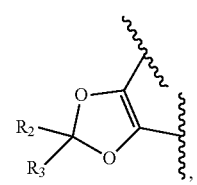

5

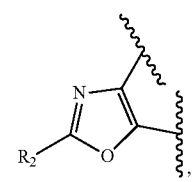

6

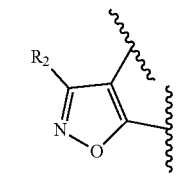

7

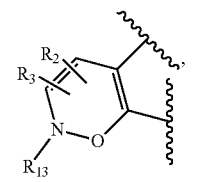
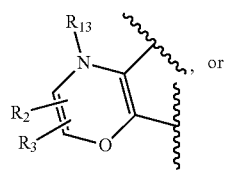
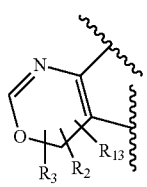
wherein
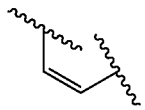 [SMILES: */C=C\*]
denotes a portion of the phenyl ring to which ring A is fused.
In another embodiment of the invention A is:
1
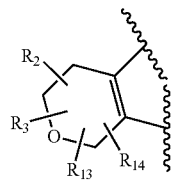
2
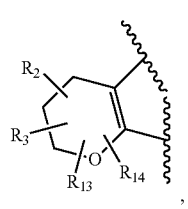
3
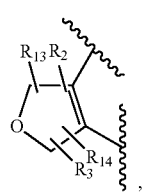
4
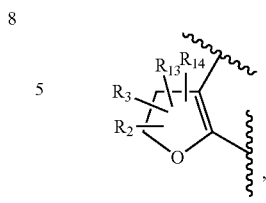
5
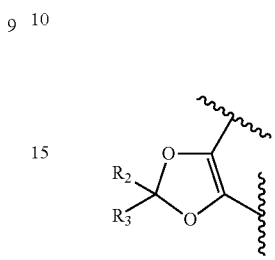
7
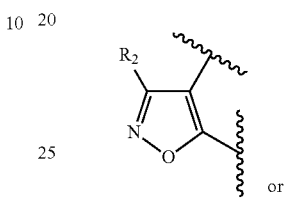
or
10
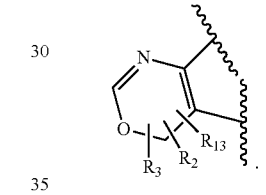
wherein
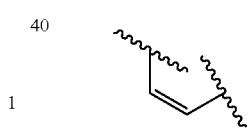
denotes a portion of the phenyl ring to which ring A is fused.
In a further embodiment of the invention A is:
1
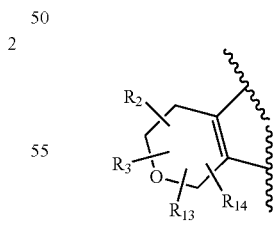
2
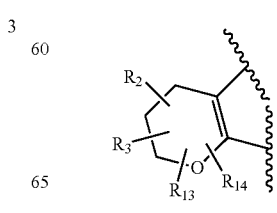

-continued

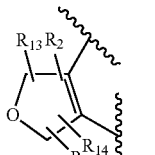

3

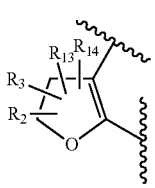 or

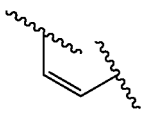 [SMILES: */C=C\*]

wherein

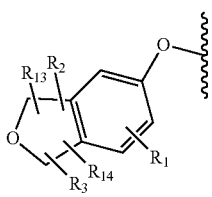

denotes a portion of the phenyl ring to which ring A is fused.

When A contains a 5 membered heterocycle containing one oxygen atom, suitably the heterocycle is dihydrofuran.

When A is a 5 membered heterocycle containing one oxygen atom, suitably the oxygen atom is located at the benzylic position relative to the phenyl ring.

When W is group (Wa), suitably A is a 5 membered heterocycle containing one heteroatom, wherein the oxygen atom is located at the benzylic or para position relative to the phenyl ring.

When W is group (Wb), suitably A is a 5 membered heterocycle containing one heteroatom, wherein the oxygen atom is located at the benzylic or meta position relative to the phenyl ring.

When W is group (Wa), in one embodiment of the invention, group (Wa) is:

11

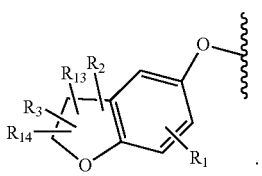

When W is group (Wa), in another embodiment or the invention, group (Wa) is:

12

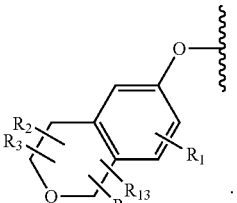

When W is group (Wb), in one embodiment of the invention, group (Wb) is:

13

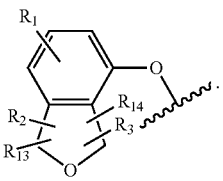

When W is group (Wb), in another embodiment of the invention, (Wb) is:

14

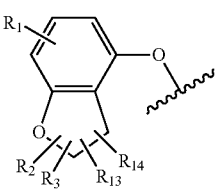

When W is group (Wb) in a further embodiment of the invention, group (Wb) is:

15

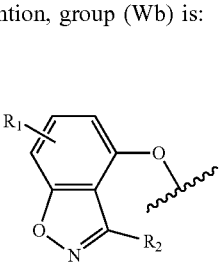

When A contains a 6 membered heterocycle containing one oxygen atom, suitably the heterocycle is dihydropyran.

When W is group (Wa), suitably A is a 6 membered heterocycle containing one oxygen atom, wherein the oxygen atom is located at the para position relative to the phenyl ring.

When W is group (Wb), suitably A contains a 6 membered heterocycle containing one oxygen atom, wherein the oxygen atom is located at the meta position relative to the phenyl ring.

When W is group (Wa), in one embodiment of the invention, group (Wa) is:

16

When W is group (Wa), in another embodiment of the invention, group (Wa) is:

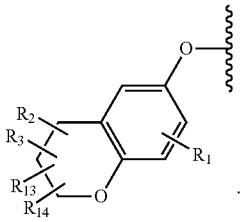

17

When W is group (Wb), in one embodiment of the invention, group (Wb) is:

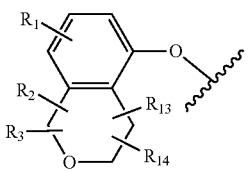

18

When W is group (Wb), in one embodiment of the invention, group (Wb) is:

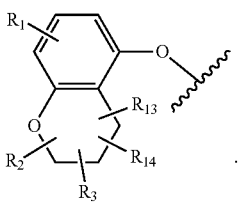

19

When W is group (Wb), in one embodiment of the invention, group (Wb) is:

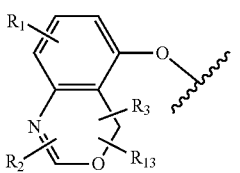

20

When W is group (Wa), in one embodiment of the invention, A is:

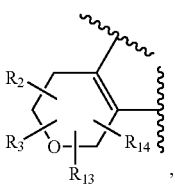

1

-continued

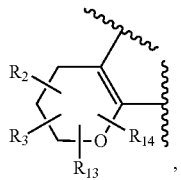

2

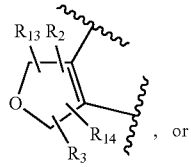

3

, or

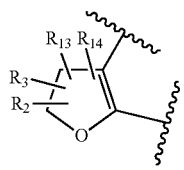

4

When W is group (Wa), in one embodiment of the invention, A is:

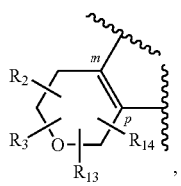

21

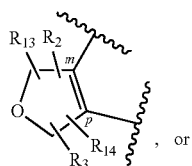

22

, or

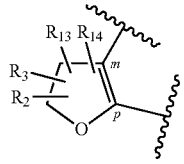

23

;

wherein m and p denote the meta and para positions, respectively, of ring A relative to the phenyl ring.

When W is group (Wa), in a further embodiment of the invention, A is selected from the group consisting of:

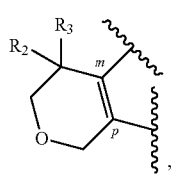

24

,

-continued
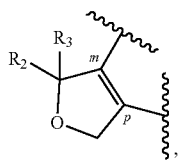
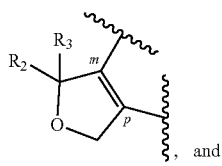
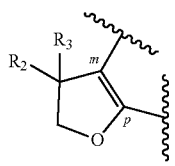
wherein m and p denote the meta and para positions, respectively, of ring A relative to the phenyl ring.
When W is group (Wb), in one embodiment of the invention, A is:
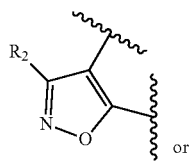
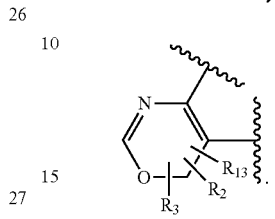
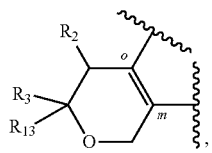
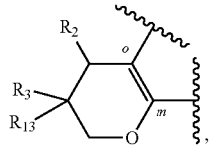
When W is group (Wb), in one embodiment of the invention, A is:
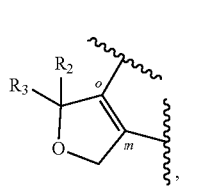
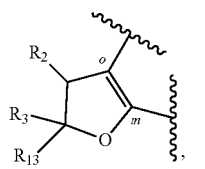
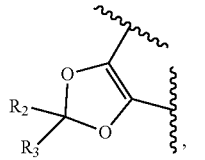
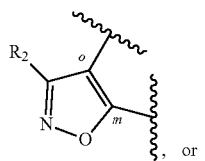
or

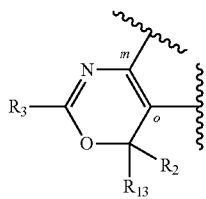

33 wherein m and o denote the meta and ortho positions, respectively, of ring A relative to the phenyl ring.

When W is group (Wb), in one embodiment of the invention, A is:

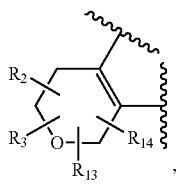

1

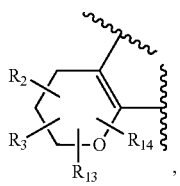

2

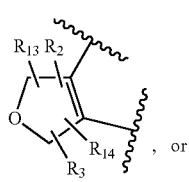

, or

3

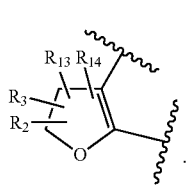

4

When W is group (Wb), in another embodiment of the invention, A is:

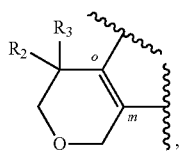

34

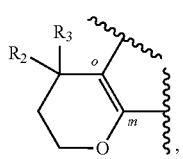

35

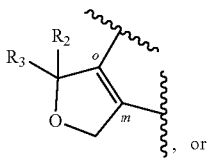

5 , or

30

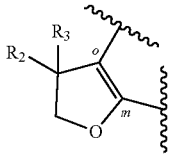

32 wherein m and o denote the meta and ortho positions, respectively, of ring A relative to the phenyl ring.

In one embodiment of the invention, W is the group (Wc):

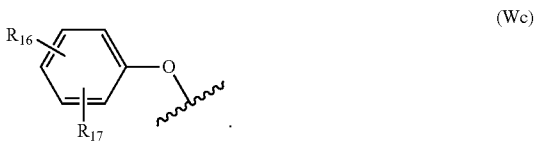

(Wc)

In one embodiment of the invention $R_{16}$ is $C_{1-4}$alkoxy. In another embodiment of the invention $R_{16}$ is methoxy. In one embodiment of the invention $R_{16}$ is $C_{1-4}$alkyl. In another embodiment of the invention $R_{16}$ is methyl. In a further embodiment of the invention $R_{16}$ is ethyl. In a yet further embodiment of the invention $R_{16}$ is propyl. In a yet further embodiment of the invention $R_{16}$ is butyl. In one embodiment of the invention $R_{16}$ is halo. In another embodiment of the invention $R_{16}$ is chloro. In a further embodiment of the invention $R_{16}$ is fluoro. In one embodiment of the invention $R_{16}$ is halo-$C_{1-4}$alkoxy. In another embodiment of the invention $R_{16}$ is trifluoromethoxy. In one embodiment of the invention $R_{16}$ is halo-$C_{1-4}$alkyl. In another embodiment of the invention $R_{16}$ is trifluoromethyl. In one embodiment of the invention $R_{16}$ is cyano.

In one embodiment of the invention, $R_{17}$ is H. In one embodiment of the invention $R_{17}$ is $C_{1-4}$alkyl. In another embodiment of the invention $R_{17}$ is methyl. In one embodiment of the invention $R_{17}$ is halo. In another embodiment of the invention, $R_{17}$ is chloro. In a further embodiment of the invention $R_{17}$ is fluoro. In one embodiment of the invention $R_{17}$ is $C_{1-4}$alkyl. In one embodiment of the invention $R_{17}$ is cyano.

In one embodiment of the invention $R_{16}$ is $C_{1-4}$alkyl, $C_{1-4}$alkoxy, or halo-$C_{1-4}$alkoxy; $R_{17}$ is H, cyano or alkyl; X is N, Y is N or $CR_{15}$, $R_4$ is $C_{1-4}$alkyl, and $R_5$ is $C_{1-4}$alkyl or H. In one embodiment of the invention $R_{16}$ is propyl, butyl, methoxy, propoxy, or trifluoromethoxy; $R_{17}$ is H, cyano or methyl; X is N, Y is N or $CR_{15}$, $R_4$ is ethyl, and $R_5$ is methyl or H.

In one embodiment, one of $R_{16}$ and $R_{17}$ is in the para position and the remaining $R_{16}$ or $R_{17}$ is in the meta position. In one embodiment, one of $R_{16}$ and $R_{17}$ is in the para position and the remaining $R_{16}$ or $R_{17}$ is in the ortho position.

In one embodiment of the invention $R_{16}$ is $C_{1-4}$alkoxy and $R_{17}$ is $C_{1-4}$alkyl. In one embodiment of the invention $R_{16}$ is methoxy and $R_{17}$ is methyl. In one embodiment of the invention $R_{16}$ is $C_{1-4}$alkoxy in the meta position and $R_{17}$ is $C_{1-4}$alkyl in the para position. In a further embodiment of the invention $R_{16}$ is methoxy in the meta position, $R_{17}$ is methyl in the para position, $R_4$ is $C_{1-4}$alkyl, $R_5$ is H, $R_4$ is in the R configuration. In a yet further embodiment of the invention $R_{16}$ is methoxy in the meta position, $R_{17}$ is methyl in the para position, X is N, Y is CH, $R_4$ is $C_{1-4}$alkyl, $R_5$ is H and the absolute configuration of the stereogenic centre is R. In a still further embodiment of the invention $R_{16}$ is methoxy in the meta position, $R_{17}$ is methyl in the para position, X is N, Y is CH, $R_4$ is ethyl, $R_5$ is H and the absolute configuration of the stereogenic centre is R.

In one embodiment of the invention, W is the group (Wd):

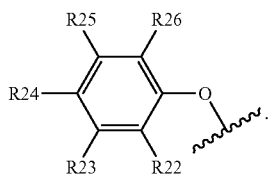
(Wd)

In one embodiment of the invention, $R_{22}$, $R_{25}$ and $R_{26}$ are H. In another embodiment $R_{23}$ is $C_{1-4}$alkyl, Cl, $CF_3$, O—$C_{1-4}$alkyl, $OCF_3$ or $N(CH_3)_2$, such as $C_{1-2}$alkyl, $CF_3$, O—$C_{1-2}$alkyl or $OCF_3$, in particular $OCF_3$ and $R_{24}$ is H, Cl, F, $C_{1-4}$alkyl, O—$C_{1-4}$alkyl, CN, $OCF_3$, such as F, $C_{1-2}$alkyl, $CF_3$, O—$C_{1-2}$alkyl or $OCF_3$, in particular F or methyl and $R_{22}$, $R_{25}$ and $R_{26}$ are H.

Alternatively, when W is group (Wd), suitably four of $R_{22}$ to $R_{26}$ are H and one of $R_{22}$ to $R_{26}$, in particular $R_{22}$ or $R_{23}$, is other than H. When $R_{22}$ is other than H, suitably it is methyl. When $R_{23}$ is other than H, suitably it is $OCF_3$.

When Z is (Za), suitably, $R_4$ is $C_{1-4}$ alkyl. In one embodiment of the invention $R_4$ is methyl, ethyl, isopropyl or t-butyl. In another embodiment of the invention $R_4$ is methyl. In a further embodiment of the invention $R_4$ is ethyl. In a yet further embodiment of the invention $R_4$ is propyl, such as isopropyl. In a yet further embodiment of the invention $R_4$ is butyl, such as t-butyl.

Suitably, $R_5$ is H or $C_{1-4}$alkyl. In one embodiment of the invention $R_5$ is H. In another embodiment of the invention $R_4$ is methyl, ethyl, isopropyl or t-butyl. In another embodiment of the invention $R_4$ is methyl. In a yet further embodiment of the invention $R_4$ is ethyl. In a yet further embodiment of the invention $R_4$ is propyl, such as isopropyl. In a yet further embodiment of the invention $R_4$ is butyl, such as t-butyl.

In one embodiment of the invention $R_4$ and $R_5$ together form a $C_3$ spiro carbocycle. In a second embodiment of the invention $R_4$ and $R_5$ together form a $C_4$ spiro carbocycle. In a further embodiment of the invention $R_4$ is methyl and $R_5$ is methyl. In an embodiment of particular interest, $R_4$ is ethyl and $R_5$ is methyl. In another embodiment, $R_4$ is ethyl and $R_5$ is ethyl. In an additional embodiment, $R_4$ is ethyl and $R_5$ is H.

Suitably, $R_4$ and $R_5$ have the stereochemical arrangement:

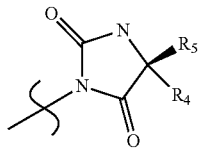

When Z is (Zb), in one embodiment of the invention $R_4$ is H. In a further embodiment of the invention $R_4$ is $C_{1-4}$alkyl, in particular methyl, ethyl, isopropyl, tert-butyl or cyclopropyl. In one embodiment of the invention $R_4$ is methyl. In another embodiment of the invention $R_4$ is ethyl.

In one embodiment of the invention X is CH. In another embodiment of the invention X is N.

In one embodiment of the invention Y is $CR_{15}$. In another embodiment of the invention Y is N.

In a further embodiment of the invention Y is $CR_{15}$, wherein $R_{15}$ is H. In a still further embodiment of the invention Y is $CR_{15}$, wherein $R_{15}$ is $C_{1-4}$alkyl, in particular methyl.

In one embodiment of the invention X is CH and Y is $CR_{15}$, wherein $R_{15}$ is H. In another embodiment of the invention X is N and Y is $CR_{15}$, wherein $R_{15}$ is H. In a further embodiment of the invention X is N and Y is $CR_{15}$, wherein $R_{15}$ is methyl. In a further embodiment of the invention X is CH and Y is $CR_{15}$, wherein $R_{15}$ is methyl. In a still further embodiment of the invention X is N and Y is N.

Suitably, when Z is (Zb), one embodiment of the invention provides a compound of formula (IFa):

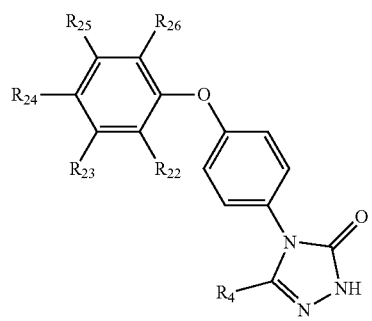
(IFa)

wherein:
$R_4$ is $CH_3$ or H;
$R_{22}$ is H, Cl, F or $C_{1-4}$alkyl;
$R_{23}$ is H, $C_{1-4}$alkyl, Cl, $CF_3$, O—$C_{1-4}$alkyl, $OCF_3$ or $N(CH_3)_2$;
$R_{24}$ is H, Cl, F, $C_{1-4}$alkyl, O—$C_{1-4}$alkyl, CN, $OCF_3$ or $CF_3$;
$R_{25}$ is H, Cl, F, O—$C_{1-4}$alkyl or $C_{1-4}$alkyl; and
$R_{26}$ is H or $C_{1-4}$alkyl;
wherein $C_{1-4}$alkyl may be substituted by O-methyl;
with the provisos that:
not all of $R_{22}$ to $R_{26}$ may be H;
when $R_4$ is H, then $R_{23}$ is methyl or $CF_3$ and $R_{22}$, $R_{24}$, $R_{25}$ and $R_{26}$ are all H;
when one of $R_{22}$, $R_{24}$, $R_{25}$ or $R_{26}$ is F, then $R_{22}$ to $R_{26}$ cannot be H or F; and
when $R_{24}$ is not H, at least one of $R_{22}$ or $R_{23}$ is not H;
or a pharmaceutically acceptable salt thereof.

In one embodiment of the compounds of formula (IFa) $R_{22}$ is $C_{1-4}$alkyl. In another embodiment $R_{22}$ is methyl. In a further embodiment $R_{22}$ is ethyl. In a yet further embodiment $R_{22}$ is propyl.

In one embodiment of the compounds of formula (IFa) $R_{22}$ is Cl.

In one embodiment of the compounds of formula (IFa) $R_{22}$ is F.

In one embodiment of the compounds of formula (IFa) $R_{23}$ is H.

In one embodiment of the compounds of formula (IFa) $R_{23}$ is $C_{1-4}$ alkyl. In another embodiment of the compounds of formula (IFa) $R_{23}$ is methyl.

In one embodiment of the compounds of formula (IFa) $R_{23}$ is chloro.

In one embodiment of the compounds of formula (IFa) $R_{23}$ is methoxy. In another embodiment of the compounds of formula (IFa) $R_{23}$ is ethoxy.

In one embodiment of the compounds of formula (IFa) $R_{23}$ is trifluoromethyl.

In one embodiment of the compounds of formula (IFa) $R_{23}$ is trifluoromethoxy.

In one embodiment of the compounds of formula (IFa) $R_{23}$ is $N(CH_3)_2$.

In one embodiment of the compounds of formula (IFa) $R_{24}$ is H.

In one embodiment of the compounds of formula (IFa) $R_{24}$ is methyl.

In one embodiment of the compounds of formula (IFa) $R_{24}$ is chloro.

In one embodiment of the compounds of formula (IFa) $R_{24}$ is fluoro.

In one embodiment of the compounds of formula (IFa) $R_{25}$ is H.

In one embodiment of the compounds of formula (IFa) $R_{25}$ is methyl.

In one embodiment of the compounds of formula (IFa) $R_{25}$ is chloro.

In one embodiment of the compounds of formula (IFa) $R_{25}$ is fluoro.

In one embodiment of the compounds of formula (IFa) $R_{26}$ is H.

In one embodiment of the compounds of formula (IFa) $R_{26}$ is methyl.

Suitably, when Z is (Zb), one embodiment of the invention provides a compound of formula (IFb):

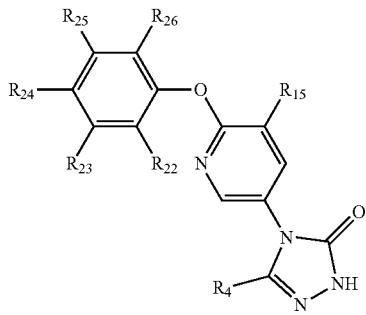

(IFb)

wherein:
$R_4$ is H or Me
$R_{23}$ is $C_3$-$C_4$ alkyl or $OC_2$-$C_4$alkyl and $R_{22}$ is H, or $R_{22}$ and $R_{23}$ are both methyl;
$R_{24}$, $R_{25}$ and $R_{26}$ are H;
$R_{15}$ is H or methyl;
or a pharmaceutically acceptable salt thereof.

In one embodiment of the compounds of formula (IFb) $R_4$ is H.

In one embodiment of the compounds of formula (IFb) $R_4$ is methyl.

In one embodiment of the compounds of formula (IFb) $R_{22}$ is H.

In one embodiment of the compounds of formula (IFb) $R_{22}$ is methyl.

In one embodiment of the compounds of formula (IFb) $R_{23}$ is $C_3$-$C_4$ alkyl. In another embodiment of the compounds of formula (IFb) $R_{23}$ is propyl.

In one embodiment of the compounds of formula (IFb) $R_{23}$ is methyl.

In one embodiment of the compounds of formula (IFb) $R_{23}$ is $OC_2$-$C_4$alkyl. In another embodiment of the compounds of formula (IFb) $R_{23}$ is ethoxy.

In one embodiment of the compounds of formula (IFb) $R_{24}$ is H.

In one embodiment of the compounds of formula (IFb) $R_{25}$ is H.

In one embodiment of the compounds of formula (IFb) $R_{26}$ is H.

In one embodiment of the compounds of formula (IFb) $R_{15}$ is H.

In one embodiment of the compounds of formula (IFb) $R_{15}$ is methyl.

References to "formula (I)" should also be construed as also referring to formula (IA), formula (IB), formula (IC), formula (ID), formula (IE), formula (IF), formula (IFa) and formula (IFb) as appropriate to the circumstances.

Suitably, the compound of formula (I) may contain a W group corresponding to one of the following phenol groups:

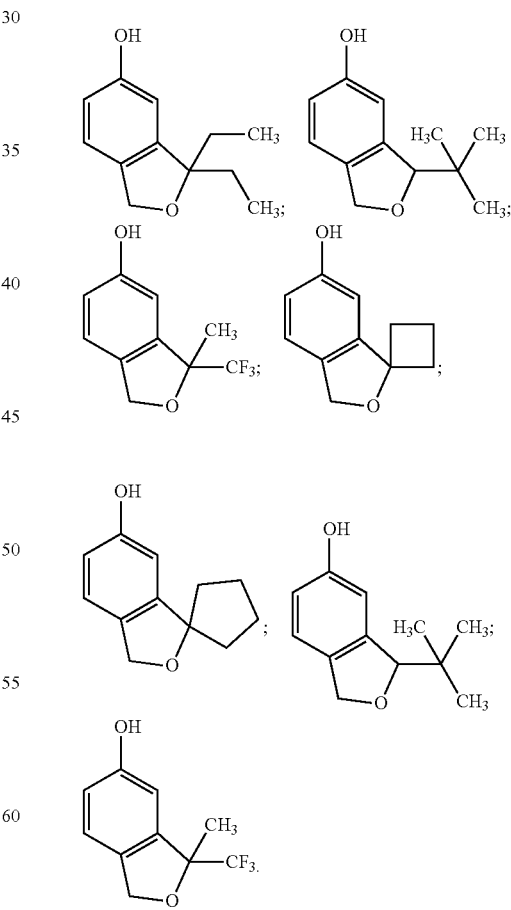

Suitably, the compound of formula (I) contains a (Wa) group corresponding to one of the following phenol groups:

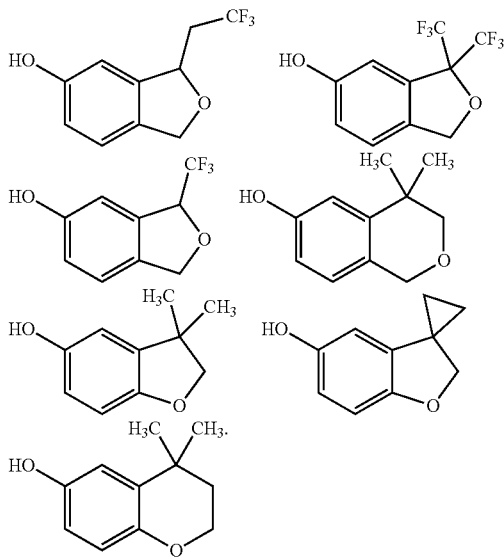

Suitably, the compound of formula (I) contains a (Wb) group corresponding to one of the following phenol groups:

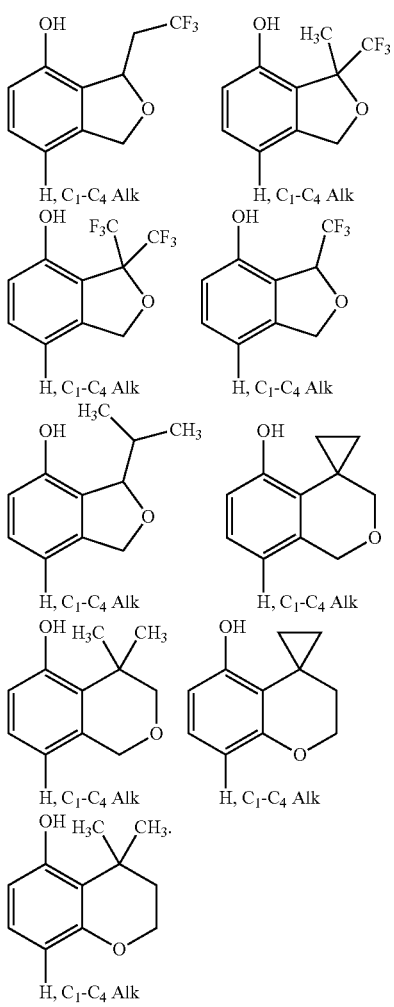

Alternatively, when the compound of formula (I) contains a (Wb) group corresponding to one of the following phenol groups:

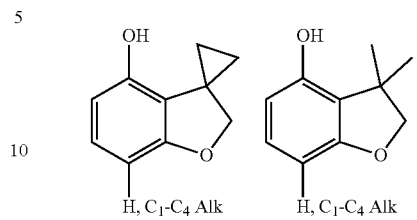

Alternatively, the compound of formula (I) may contain a (Wb) group corresponding to one of the following phenol groups:

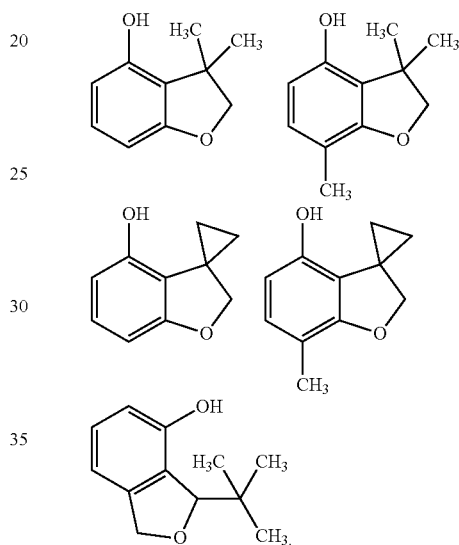

When Z is (Za) and W is group (Wa), suitably the compound of formula (I) is selected from:

3-[2-[(3,3-dimethyl-1H-isobenzofuran-5-yl)oxy]pyrimidin-5-yl]-5,5-dimethyl-imidazolidine-2,4-dione;

3-[2-[(3,3-diethyl-1H-isobenzofuran-5-yl)oxy]pyrimidin-5-yl]-5,5-dimethyl-imidazolidine-2,4-dione;

3-[2-[(3-tert-butyl-1,3-dihydroisobenzofuran-5-yl)oxy]pyrimidin-5-yl]-5,5-dimethyl-imidazolidine-2,4-dione (enantiomer 1);

3-[2-[(3-tert-butyl-1,3-dihydroisobenzofuran-5-yl)oxy]pyrimidin-5-yl]-5,5-dimethyl-imidazolidine-2,4-dione (enantiomer 2);

5,5-dimethyl-3-[2-[[3-methyl-3-(trifluoromethyl)-1H-isobenzofuran-5-yl]oxy]pyrimidin-5-yl]imidazolidine-2,4-dione (enantiomer 1);

5,5-dimethyl-3-[2-[[3-methyl-3-(trifluoromethyl)-1H-isobenzofuran-5-yl]oxy]pyrimidin-5-yl]imidazolidine-2,4-dione (enantiomer 2);

3-[2-[(3-ethyl-1,3-dihydroisobenzofuran-5-yl)oxy]pyrimidin-5-yl]-5,5-dimethyl-imidazolidine-2,4-dione (enantiomer 1);

3-[2-[(3-ethyl-1,3-dihydroisobenzofuran-5-yl)oxy]pyrimidin-5-yl]-5,5-dimethyl-imidazolidine-2,4-dione (enantiomer 2);

3-[2-[(3-cyclopropyl-1,3-dihydroisobenzofuran-5-yl)oxy]pyrimidin-5-yl]-5,5-dimethyl-imidazolidine-2,4-dione (enantiomer 1);

3-[2-[(3-cyclopropyl-1,3-dihydroisobenzofuran-5-yl)oxy]
pyrimidin-5-yl]-5,5-dimethyl-imidazolidine-2,4-dione
(enantiomer 2);

5,5-dimethyl-3-(2-spiro[1H-isobenzofuran-3,1'-cyclobutane]-5-yloxypyrimidin-5-yl)imidazolidine-2,4-dione;

5,5-dimethyl-3-(2-spiro[1H-isobenzofuran-3,1'-cyclopentane]-5-yloxypyrimidin-5-yl)imidazolidine-2,4-dione;

5,5-dimethyl-3-[2-[[3-(trifluoromethyl)-1,3-dihydroisobenzofuran-5-yl]oxy]pyrimidin-5-yl]imidazolidine-2,4-dione (enantiomer 1);

5,5-dimethyl-3-[2-[[3-(trifluoromethyl)-1,3-dihydroisobenzofuran-5-yl]oxy]pyrimidin-5-yl]imidazolidine-2,4-dione (enantiomer 2);

3-[2-[(3,3-dimethyl-2H-benzofuran-5-yl)oxy]pyrimidin-5-yl]-5,5-dimethyl-imidazolidine-2,4-dione;

3-[2-(4,4-dimethylisochroman-6-yl)oxypyrimidin-5-yl]-5,5-dimethyl-imidazolidine-2,4-dione;

(5R)-3-[2-[(3,3-dimethyl-1H-isobenzofuran-5-yl)oxy]pyrimidin-5-yl]-5-ethyl-5-methyl-imidazolidine-2,4-dione;

(5R)-3-[2-[(3,3-diethyl-1H-isobenzofuran-5-yl)oxy]pyrimidin-5-yl]-5-ethyl-5-methyl-imidazolidine-2,4-dione;

(5R)-3-[2-[(3-tert-butyl-1,3-dihydroisobenzofuran-5-yl)oxy]pyrimidin-5-yl]-5-ethyl-5-methyl-imidazolidine-2,4-dione (diastereoisomer 1);

(5R)-3-[2-[(3-tert-butyl-1,3-dihydroisobenzofuran-5-yl)oxy]pyrimidin-5-yl]-5-ethyl-5-methyl-imidazolidine-2,4-dione (diastereoisomer 2);

(5R)-5-ethyl-5-methyl-3-[2-[[3-methyl-3-(trifluoromethyl)-1H-isobenzofuran-5-yl]oxy]pyrimidin-5-yl]imidazolidine-2,4-dione (diastereoisomer 1);

(5R)-5-ethyl-5-methyl-3-[2-[[3-methyl-3-(trifluoromethyl)-1H-isobenzofuran-5-yl]oxy]pyrimidin-5-yl]imidazolidine-2,4-dione (diastereoisomer 2);

(5R)-5-ethyl-3-[2-[(3-ethyl-1,3-dihydroisobenzofuran-5-yl)oxy]pyrimidin-5-yl]-5-methyl-imidazolidine-2,4-dione (diastereoisomer 1);

(5R)-5-ethyl-3-[2-[(3-ethyl-1,3-dihydroisobenzofuran-5-yl)oxy]pyrimidin-5-yl]-5-methyl-imidazolidine-2,4-dione (diastereoisomer 2);

(5R)-3-[2-[(3-cyclopropyl-1,3-dihydroisobenzofuran-5-yl)oxy]pyrimidin-5-yl]-5-ethyl-5-methyl-imidazolidine-2,4-dione (diastereoisomer 1);

(5R)-3-[2-[(3-cyclopropyl-1,3-dihydroisobenzofuran-5-yl)oxy]pyrimidin-5-yl]-5-ethyl-5-methyl-imidazolidine-2,4-dione (diastereoisomer 2);

(5R)-5-ethyl-5-methyl-3-(2-spiro[1H-isobenzofuran-3,1'-cyclobutane]-5-yloxypyrimidin-5-yl)imidazolidine-2,4-dione;

(5R)-5-ethyl-5-methyl-3-(2-spiro[1H-isobenzofuran-3,1'-cyclopentane]-5-yloxypyrimidin-5-yl)imidazolidine-2,4-dione;

(5R)-5-ethyl-5-methyl-3-[2-[[3-(trifluoromethyl)-1,3-dihydroisobenzofuran-5-yl]oxy]pyrimidin-5-yl]imidazolidine-2,4-dione (diastereoisomer 1);

(5R)-5-ethyl-5-methyl-3-[2-[[3-(trifluoromethyl)-1,3-dihydroisobenzofuran-5-yl]oxy]pyrimidin-5-yl]imidazolidine-2,4-dione (diastereoisomer 2);

(5R)-3-[2-[(3,3-dimethyl-2H-benzofuran-5-yl)oxy]pyrimidin-5-yl]-5-ethyl-5-methyl-imidazolidine-2,4-dione;

(5R)-3-[2-(4,4-dimethylisochroman-6-yl)oxypyrimidin-5-yl]-5-ethyl-5-methyl-imidazolidine-2,4-dione;

(5R)-3-[6-[(3,3-dimethyl-1H-isobenzofuran-5-yl)oxy]-3-pyridyl]-5-ethyl-5-methyl-imidazolidine-2,4-dione;

(5R)-3-[6-[(3,3-diethyl-1H-isobenzofuran-5-yl)oxy]-3-pyridyl]-5-ethyl-5-methyl-imidazolidine-2,4-dione;

(5R)-3-[6-[(3-tert-butyl-1,3-dihydroisobenzofuran-5-yl)oxy]-3-pyridyl]-5-ethyl-5-methyl-imidazolidine-2,4-dione (diastereoisomer 1);

(5R)-3-[6-[(3-tert-butyl-1,3-dihydroisobenzofuran-5-yl)oxy]-3-pyridyl]-5-ethyl-5-methyl-imidazolidine-2,4-dione (diastereoisomer 2);

(5R)-5-ethyl-5-methyl-3-[6-[[3-methyl-3-(trifluoromethyl)-1H-isobenzofuran-5-yl]oxy]-3-pyridyl]imidazolidine-2,4-dione (diastereoisomer 1);

(5R)-5-ethyl-5-methyl-3-[6-[[3-methyl-3-(trifluoromethyl)-1H-isobenzofuran-5-yl]oxy]-3-pyridyl]imidazolidine-2,4-dione (diastereoisomer 2);

(5R)-5-ethyl-3-[6-[(3-ethyl-1,3-dihydroisobenzofuran-5-yl)oxy]-3-pyridyl]-5-methyl-imidazolidine-2,4-dione (diastereoisomer 1);

(5R)-5-ethyl-3-[6-[(3-ethyl-1,3-dihydroisobenzofuran-5-yl)oxy]-3-pyridyl]-5-methyl-imidazolidine-2,4-dione (diastereoisomer 2);

(5R)-3-[6-[(3-cyclopropyl-1,3-dihydroisobenzofuran-5-yl)oxy]-3-pyridyl]-5-ethyl-5-methyl-imidazolidine-2,4-dione (diastereoisomer 1);

(5R)-3-[6-[(3-cyclopropyl-1,3-dihydroisobenzofuran-5-yl)oxy]-3-pyridyl]-5-ethyl-5-methyl-imidazolidine-2,4-dione (diastereoisomer 2);

(5R)-5-ethyl-5-methyl-3-(6-spiro[1H-isobenzofuran-3,1'-cyclobutane]-5-yloxy-3-pyridyl)imidazolidine-2,4-dione;

(5R)-5-ethyl-5-methyl-3-(6-spiro[1H-isobenzofuran-3,1'-cyclopentane]-5-yloxy-3-pyridyl)imidazolidine-2,4-dione;

(5R)-5-ethyl-5-methyl-3-[6-[[3-(trifluoromethyl)-1,3-dihydroisobenzofuran-5-yl]oxy]-3-pyridyl]imidazolidine-2,4-dione (diastereoisomer 1);

(5R)-5-ethyl-5-methyl-3-[6-[[3-(trifluoromethyl)-1,3-dihydroisobenzofuran-5-yl]oxy]-3-pyridyl]imidazolidine-2,4-dione (diastereoisomer 2);

(5R)-3-[6-[(3,3-dimethyl-2H-benzofuran-5-yl)oxy]-3-pyridyl]-5-ethyl-5-methyl-imidazolidine-2,4-dione;

(5R)-3-[6-(4,4-dimethylisochroman-6-yl)oxy-3-pyridyl]-5-ethyl-5-methyl-imidazolidine-2,4-dione;

3-[6-[(3,3-diethyl-1H-isobenzofuran-5-yl)oxy]-3-pyridyl]-5,5-dimethyl-imidazolidine-2,4-dione;

3-[6-[(3-tert-butyl-1,3-dihydroisobenzofuran-5-yl)oxy]-3-pyridyl]-5,5-dimethyl-imidazolidine-2,4-dione (enantiomer 1);

3-[6-[(3-tert-butyl-1,3-dihydroisobenzofuran-5-yl)oxy]-3-pyridyl]-5,5-dimethyl-imidazolidine-2,4-dione (enantiomer 2);

5,5-dimethyl-3-[6-[[3-methyl-3-(trifluoromethyl)-1H-isobenzofuran-5-yl]oxy]-3-pyridyl]imidazolidine-2,4-dione (enantiomer 1);

5,5-dimethyl-3-[6-[[3-methyl-3-(trifluoromethyl)-1H-isobenzofuran-5-yl]oxy]-3-pyridyl]imidazolidine-2,4-dione (enantiomer 2);

3-[6-[(3-ethyl-1,3-dihydroisobenzofuran-5-yl)oxy]-3-pyridyl]-5,5-dimethyl-imidazolidine-2,4-dione (enantiomer 1);

3-[6-[(3-ethyl-1,3-dihydroisobenzofuran-5-yl)oxy]-3-pyridyl]-5,5-dimethyl-imidazolidine-2,4-dione (enantiomer 2);

3-[6-[(3-cyclopropyl-1,3-dihydroisobenzofuran-5-yl)oxy]-3-pyridyl]-5,5-dimethyl-imidazolidine-2,4-dione (enantiomer 1);

3-[6-[(3-cyclopropyl-1,3-dihydroisobenzofuran-5-yl)oxy]-3-pyridyl]-5,5-dimethyl-imidazolidine-2,4-dione (enantiomer 2);

5,5-dimethyl-3-(6-spiro[1H-isobenzofuran-3,1'-cyclobutane]-5-yloxy-3-pyridyl)imidazolidine-2,4-dione;

5,5-dimethyl-3-(6-spiro[1H-isobenzofuran-3,1'-cyclopentane]-5-yloxy-3-pyridyl)imidazolidine-2,4-dione;
5,5-dimethyl-3-[6-[[3-(trifluoromethyl)-1,3-dihydroisobenzofuran-5-yl]oxy]-3-pyridyl]imidazolidine-2,4-dione (enantiomer 1);
5,5-dimethyl-3-[6-[[3-(trifluoromethyl)-1,3-dihydroisobenzofuran-5-yl]oxy]-3-pyridyl]imidazolidine-2,4-dione (enantiomer 2);
3-[6-[(3,3-dimethyl-2H-benzofuran-5-yl)oxy]-3-pyridyl]-5,5-dimethyl-imidazolidine-2,4-dione;
3-[6-(4,4-dimethylisochroman-6-yl)oxy-3-pyridyl]-5,5-dimethyl-imidazolidine-2,4-dione;
(5R)-3-[6-[(3,3-dimethyl-1H-isobenzofuran-5-yl)oxy]-5-methyl-3-pyridyl]-5-ethyl-5-methyl-imidazolidine-2,4-dione;
(5R)-5-ethyl-5-methyl-3-[5-methyl-6-[[3-methyl-3-(trifluoromethyl)-1H-isobenzofuran-5-yl]oxy]-3-pyridyl]imidazolidine-2,4-dione (diastereoisomer 1);
(5R)-5-ethyl-5-methyl-3-[5-methyl-6-[[3-methyl-3-(trifluoromethyl)-1H-isobenzofuran-5-yl]oxy]-3-pyridyl]imidazolidine-2,4-dione (diastereoisomer 2);
(5R)-5-ethyl-5-methyl-3-(5-methyl-6-spiro[1H-isobenzofuran-3,1'-cyclobutane]-5-yloxy-3-pyridyl)imidazolidine-2,4-dione;
(5R)-5-ethyl-5-methyl-3-[5-methyl-6-[[3-(trifluoromethyl)-1,3-dihydroisobenzofuran-5-yl]oxy]-3-pyridyl]imidazolidine-2,4-dione (diastereoisomer 1);
(5R)-5-ethyl-5-methyl-3-[5-methyl-6-[[3-(trifluoromethyl)-1,3-dihydroisobenzofuran-5-yl]oxy]-3-pyridyl]imidazolidine-2,4-dione (diastereoisomer 2);
5,5-dimethyl-3-(5-methyl-6-{[3-(trifluoromethyl)-1,3-dihydro-2-benzofuran-5-yl]oxy}pyridin-3-yl)imidazolidine-2,4-dione (enantiomer 1);
5,5-dimethyl-3-(5-methyl-6-{[3-(trifluoromethyl)-1,3-dihydro-2-benzofuran-5-yl]oxy}pyridin-3-yl)imidazolidine-2,4-dione (enantiomer 2);
(5R)-3-[6-[(3,3-dimethyl-1H-isobenzofuran-5-yl)oxy]-3-pyridyl]-5-ethyl-imidazolidine-2,4-dione;
(5R)-5-ethyl-3-[6-[[3-methyl-3-(trifluoromethyl)-1H-isobenzofuran-5-yl]oxy]-3-pyridyl]imidazolidine-2,4-dione (diastereoisomer 1);
(5R)-5-ethyl-3-[6-[[3-methyl-3-(trifluoromethyl)-1H-isobenzofuran-5-yl]oxy]-3-pyridyl]imidazolidine-2,4-dione (diastereoisomer 2);
(5R)-5-ethyl-3-(6-spiro[1H-isobenzofuran-3,1'-cyclobutane]-5-yloxy-3-pyridyl)imidazolidine-2,4-dione;
(5R)-3-[6-[(3,3-dimethyl-2H-benzofuran-5-yl)oxy]-3-pyridyl]-5-ethyl-imidazolidine-2,4-dione;
(5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 1);
(5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 2);
(5R)-5-ethyl-3-(2-spiro[1H-isobenzofuran-3,1'-cyclobutane]-5-yloxypyrimidin-5-yl)imidazolidine-2,4-dione;
(5R)-3-{4-[(3,3-dimethyl-1,3-dihydro-2-benzofuran-5-yl)oxy]phenyl}-5-ethyl-5-methyl-2,4-imidazolidinedione; and
(5R)-3-[4-(1,3-dihydro-2-benzofuran-5-yloxy)phenyl]-5-methyl-2,4-imidazolidinedione;
or a pharmaceutically acceptable salt and/or solvate thereof and/or derivative thereof.
In particular, when Z is (Za) and W is group (Wa) the compound of formula (I) is:

5,5-dimethyl-3-[2-[[3-methyl-3-(trifluoromethyl)-1H-isobenzofuran-5-yl]oxy]pyrimidin-5-yl]imidazolidine-2,4-dione (enantiomer 1);
5,5-dimethyl-3-[2-[[3-methyl-3-(trifluoromethyl)-1H-isobenzofuran-5-yl]oxy]pyrimidin-5-yl]imidazolidine-2,4-dione (enantiomer 2);
(5R)-3-[6-[(3,3-dimethyl-1H-isobenzofuran-5-yl)oxy]-3-pyridyl]-5-ethyl-5-methyl-imidazolidine-2,4-dione;
3-[6-[(3-tert-butyl-1,3-dihydroisobenzofuran-5-yl)oxy]-3-pyridyl]-5,5-dimethyl-imidazolidine-2,4-dione (enantiomer 1);
3-[6-[(3-tert-butyl-1,3-dihydroisobenzofuran-5-yl)oxy]-3-pyridyl]-5,5-dimethyl-imidazolidine-2,4-dione (enantiomer 2);
5,5-dimethyl-3-[6-[[3-methyl-3-(trifluoromethyl)-1H-isobenzofuran-5-yl]oxy]-3-pyridyl]imidazolidine-2,4-dione (enantiomer 1);
5,5-dimethyl-3-[6-[[3-methyl-3-(trifluoromethyl)-1H-isobenzofuran-5-yl]oxy]-3-pyridyl]imidazolidine-2,4-dione (enantiomer 2);
5,5-dimethyl-3-(6-spiro[1H-isobenzofuran-3,1'-cyclobutane]-5-yloxy-3-pyridyl)imidazolidine-2,4-dione;
(5R)-3-[6-[(3,3-dimethyl-1H-isobenzofuran-5-yl)oxy]-3-pyridyl]-5-ethyl-imidazolidine-2,4-dione;
(5R)-5-ethyl-3-[6-[[3-methyl-3-(trifluoromethyl)-1H-isobenzofuran-5-yl]oxy]-3-pyridyl]imidazolidine-2,4-dione (diastereoisomer 1);
(5R)-5-ethyl-3-[6-[[3-methyl-3-(trifluoromethyl)-1H-isobenzofuran-5-yl]oxy]-3-pyridyl]imidazolidine-2,4-dione (diastereoisomer 2);
(5R)-5-ethyl-3-(6-spiro[1H-isobenzofuran-3,1'-cyclobutane]-5-yloxy-3-pyridyl)imidazolidine-2,4-dione;
(5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 1);
(5R)-5-ethyl-3-[2-[[3-methyl-3-(trifluoromethyl)-1H-isobenzofuran-5-yl]oxy]pyrimidin-5-yl]imidazolidine-2,4-dione (diastereoisomer 2);
(5R)-5-ethyl-3-(2-spiro[1H-isobenzofuran-3,1'-cyclobutane]-5-yloxypyrimidin-5-yl)imidazolidine-2,4-dione;
(5R)-3-{4-[(3,3-dimethyl-1,3-dihydro-2-benzofuran-5-yl)oxy]phenyl}-5-ethyl-5-methyl-2,4-imidazolidinedione;
or a pharmaceutically acceptable salt and/or solvate thereof and/or derivative thereof.
When Z is (Za) and W is group (Wb), suitably the compound of formula (I) is selected from:
(5R)-3-[4-(1,3-dihydro-2-benzofuran-4-yloxy)phenyl]-5-methyl-2,4-imidazolidinedione;
(5R)-5-methyl-3-{4-[(3-methyl-1,2-benzisoxazol-4-yl)oxy]phenyl}-2,4-imidazolidinedione;
(5R)-3-{4-[(3,6-dimethyl-1,2-benzisoxazol-4-yl)oxy]phenyl}-5-methyl-2,4-imidazolidinedione;
5,5-dimethyl-3-{4-[(3-methyl-1,2-benzisoxazol-4-yl)oxy]phenyl}-2,4-imidazolidinedione;
(5R)-5-ethyl-3-{6-[(3-ethyl-1,2-benzisoxazol-4-yl)oxy]-3-pyridinyl}-2,4-imidazolidinedione;
(5R)-5-ethyl-3-(6-{[3-(1-methylethyl)-1,2-benzisoxazol-4-yl]oxy}-3-pyridinyl)-2,4-imidazolidinedione;
(5R)-3-{4-[(3,3-dimethyl-2,3-dihydro-1-benzofuran-4-yl)oxy]phenyl}-5-methyl-2,4-imidazolidinedione;
(5R)-3-{6-[(3,3-dimethyl-2,3-dihydro-1-benzofuran-4-yl)oxy]-3-pyridinyl}-5-methyl-2,4-imidazolidinedione;
(5R)-3-{6-[(3,3-dimethyl-2,3-dihydro-1-benzofuran-4-yl)oxy]-3-pyridinyl}-5-ethyl-2,4-imidazolidinedione;
(5R)-3-{2-[(3,3-dimethyl-2,3-dihydro-1-benzofuran-4-yl)oxy]-5-pyrimidinyl}-5-ethyl-2,4-imidazolidinedione;

7-{6-[(3,3-dimethyl-2,3-dihydro-1-benzofuran-4-yl)oxy]-3-pyridinyl}-5,7-diazaspiro[3.4]octane-6,8-dione;
6-{6-[(3,3-dimethyl-2,3-dihydro-1-benzofuran-4-yl)oxy]-3-pyridinyl}-4,6-diazaspiro[2.4]heptane-5,7-dione;
3-{6-[(3,3-dimethyl-2,3-dihydro-1-benzofuran-4-yl)oxy]-3-pyridinyl}-5,5-dimethyl-2,4-imidazolidinedione;
(5R)-3-{2-[(3,3-dimethyl-2,3-dihydro-1-benzofuran-4-yl)oxy]-5-pyrimidinyl}-5-(1,1-dimethylethyl)-2,4-imidazolidinedione;
(5R)-5-ethyl-3-[6-(spiro[1-benzofuran-3,1'-cyclopropan]-4-yloxy)-3-pyridinyl]-2,4-imidazolidinedione;
5,5-dimethyl-3-[6-(spiro[1-benzofuran-3,1'-cyclopropan]-4-yloxy)-3-pyridinyl]-2,4-imidazolidinedione;
(5R)-5-ethyl-5-methyl-3-[6-(spiro[1-benzofuran-3,1'-cyclopropan]-4-yloxy)-3-pyridinyl]-2,4-imidazolidinedione;
(5R)-5-ethyl-3-(6-{[(3S/R)-3-methyl-1,3-dihydro-2-benzofuran-4-yl]oxy}-3-pyridinyl)-2,4-imidazolidinedione (diastereoisomeric mixture);
(5R)-5-ethyl-3-{6-[(3-methyl-1,3-dihydro-2-benzofuran-4-yl)oxy]-3-pyridinyl}-2,4-imidazolidinedione (diastereoisomers 1 and 2);
(5R)-5-ethyl-3-{6-[(3-ethyl-1,3-dihydro-2-benzofuran-4-yl)oxy]-3-pyridinyl}-2,4-imidazolidinedione (distereoisomeric mixture);
(5R)-5-ethyl-3-{6-[(3-ethyl-1,3-dihydro-2-benzofuran-4-yl)oxy]-3-pyridinyl}-2,4-imidazolidinedione (diastereoisomers 1 and 2);
5,5-dimethyl-3-{6-[(3-methyl-3,4-dihydro-2H-chromen-5-yl)oxy]-3-pyridinyl}-2,4-imidazolidinedione (racemate mixture);
5,5-dimethyl-3-{6-[(3-methyl-3,4-dihydro-2H-chromen-5-yl)oxy]-3-pyridinyl}-2,4-imidazolidinedione (enantiomers 1 and enantiomer 2);
5,5-dimethyl-3-{6-[(1a-methyl-1,1a,2,7b-tetra hydrocyclopropa[c]chromen-7-yl)oxy]-3-pyridinyl}-2,4-imidazolidinedione;
5,5-dimethyl-3-{6-[(1a-methyl-1,1a,2,7b-tetra hydrocyclopropa[c]chromen-7-yl)oxy]-3-pyridinyl}-2,4-imidazolidinedione (enantiomer 1 and enantiomer 2);
(5R)-5-ethyl-5-methyl-3-[6-(1H-spiro[2-benzopyran-4,1'-cyclopropan]-5-yloxy)-3-pyridinyl]-2,4-imidazolidinedione;
3-{2-[(3,3-dimethyl-2,3-dihydro-1-benzofuran-4-yl)oxy]-5-pyrimidinyl}-5,5-dimethyl-2,4-imidazolidinedione;
(5R)-3-{2-[(3,3-dimethyl-2,3-dihydro-1-benzofuran-4-yl)oxy]-5-pyrimidinyl}-5-(1-methylethyl)-2,4-imidazolidinedione;
(5R)-3-{6-[(2,2-dimethyl-2,3-dihydro-1-benzofuran-4-yl)oxy]-3-pyridinyl}-5-ethyl-2,4-imidazolidinedione;
5,5-dimethyl-3-[6-(1H-spiro[2-benzopyran-4,1'-cyclopropan]-5-yloxy)-3-pyridinyl]-2,4-imidazolidinedione;
(5R)-3-[2-(2,3-dihydrospiro[chromene-4,1'-cyclopropan]-5-yloxy)-5-pyrimidinyl]-5-ethyl-5-methyl-2,4-imidazolidinedione;
5,5-dimethyl-3-{6-[(4-methyl-3,4-dihydro-2H-chromen-5-yl)oxy]-3-pyridinyl}-2,4-imidazolidinedione (racemate mixture, enantiomer 1, enantiomer 2);
(5R)-5-ethyl-5-methyl-3-{6-[(3-methyl-3,4-dihydro-2H-chromen-5-yl)oxy]-3-pyridinyl}-2,4-imidazolidinedione (diastereoisomeric mixture, diastereoisomer 1, diastereoisomer 2);
(5R)-5-ethyl-5-methyl-3-[6-(1,1a,2,7b-tetra hydrocyclopropa[c]chromen-7-yloxy)-3-pyridinyl]-2,4-imidazolidinedione (diastereoisomeric mixture, diastereoisomer 1, diastereoisomer 2);
3-{6-[(3-ethyl-1,3-dihydro-2-benzofuran-4-yl)oxy]-3-pyridinyl}-5,5-dimethyl-2,4-imidazolidinedione (racemate mixture, enantiomer 1, enantiomer 2);
(5R)-5-ethyl-5-methyl-3-[2-(4-methylchroman-5-yl)oxypyrimidin-5-yl]imidazolidine-2,4-dione (diastereoisomeric mixture, diastereoisomer 1, diastereoisomer 2);
(5R)-5-ethyl-5-methyl-3-[2-(7-methylspiro[2H-benzofuran-3,1'-cyclopropane]-4-yl)oxypyrimidin-5-yl]imidazolidine-2,4-dione;
(5R)-3-[2-(3,3-dimethylisochroman-5-yl)oxypyrimidin-5-yl]-5-ethyl-5-methyl-imidazolidine-2,4-dione;
(5R)-5-ethyl-5-methyl-3-[2-(7-methylspiro[1H-isobenzofuran-3,1'-cyclobutane]-4-yl)oxypyrimidin-5-yl]imidazolidine-2,4-dione;
(5R)-5-ethyl-5-methyl-3-{2-[(3,3,7-tri methyl-2,3-dihydro-1-benzofuran-4-yl)oxy]-5-pyrimidinyl}-2,4-imidazolidinedione;
(5R)-3-{2-[(2,2-difluoro-7-methyl-1,3-benzodioxol-4-yl)oxy]-5-pyrimidinyl}-5-ethyl-5-methyl-2,4-imidazolidinedione;
(5R)-3-{2-[(2,2-difluoro-1,3-benzodioxol-4-yl)oxy]-5-pyrimidinyl}-5-ethyl-5-methyl-2,4-imidazolidinedione;
(5R)-5-ethyl-5-methyl-3-{2-[(2,4,4-trimethyl-4H-3,1-benzoxazin-5-yl)oxy]-5-pyrimidinyl}-2,4-imidazolidinedione;
5,5-dimethyl-3-[2-(7-methylspiro[2H-benzofuran-3,1'-cyclopropane]-4-yl)oxypyrimidin-5-yl]imidazolidine-2,4-dione;
3-[2-(3,3-dimethylisochroman-5-yl)oxypyrimidin-5-yl]-5,5-dimethyl-imidazolidine-2,4-dione;
5,5-dimethyl-3-[2-(7-methylspiro[1H-isobenzofuran-3,1'-cyclobutane]-4-yl)oxypyrimidin-5-yl]imidazolidine-2,4-dione;
(5R)-5-ethyl-3-[2-(7-methylspiro[2H-benzofuran-3,1'-cyclopropane]-4-yl)oxypyrimidin-5-yl]imidazolidine-2,4-dione;
(5R)-5-ethyl-3-[6-(7-methylspiro[2H-benzofuran-3,1'-cyclopropane]-4-yl)oxy-3-pyridyl]imidazolidine-2,4-dione;
(5R)-5-ethyl-3-{6-[(3,3,7-tri methyl-2,3-dihydro-1-benzofuran-4-yl)oxy]-3-pyridinyl}-2,4-imidazolidinedione;
(5R)-5-ethyl-3-{2-[(3,3,7-tri methyl-2,3-dihydro-1-benzofuran-4-yl)oxy]-5-pyrimidinyl}-2,4-imidazolidinedione;
(5R)-5-ethyl-5-methyl-3-[6-(7-methylspiro[2H-benzofuran-3,1'-cyclopropane]-4-yl)oxy-3-pyridyl]imidazolidine-2,4-dione;
(5R)-3-[6-(3,3-dimethylisochroman-5-yl)oxy-3-pyridyl]-5-ethyl-5-methyl-imidazolidine-2,4-dione;
(5R)-3-[6-[(3,3-diethyl-1H-isobenzofuran-4-yl)oxy]-3-pyridyl]-5-ethyl-5-methyl-imidazolidine-2,4-dione;
(5R)-5-ethyl-5-methyl-3-[6-[(2,4,4-tri methyl-3,1-benzoxazin-5-yl)oxy]-3-pyridyl]imidazolidine-2,4-dione;
(5R)-3-{6-[(3,3-dimethyl-1,3-dihydro-2-benzofuran-4-yl)oxy]-3-pyridinyl}-5-ethyl-5-methyl-2,4-imidazolidinedione;
5,5-dimethyl-3-[6-(7-methylspiro[2H-benzofuran-3,1'-cyclopropane]-4-yl)oxy-3-pyridyl]imidazolidine-2,4-dione;
or a pharmaceutically acceptable salt and/or solvate thereof and/or derivative thereof.

In particular, when Z is (Za) and W is group (Wb) the compound of formula (I) is:
(5R)-5-ethyl-5-methyl-3-[2-(7-methylspiro[2H-benzofuran-3,1'-cyclopropane]-4-yl)oxypyrimidin-5-yl]imidazolidine-2,4-dione;
(5R)-5-ethyl-5-methyl-3-{2-[(3,3,7-tri methyl-2,3-dihydro-1-benzofuran-4-yl)oxy]-5-pyrimidinyl}-2,4-imidazolidinedione;

(5R)-3-{2-[(2,2-difluoro-7-methyl-1,3-benzodioxol-4-yl)oxy]-5-pyrimidinyl}-5-ethyl-5-methyl-2,4-imidazolidinedione;

5,5-dimethyl-3-[2-(7-methylspiro[2H-benzofuran-3,1'-cyclopropane]-4-yl)oxypyrimidin-5-yl]imidazolidine-2,4-dione;

(5R)-5-ethyl-3-[2-(7-methylspiro[2H-benzofuran-3,1'-cyclopropane]-4-yl)oxypyrimidin-5-yl]imidazolidine-2,4-dione;

(5R)-5-ethyl-3-[6-(7-methylspiro[2H-benzofuran-3,1'-cyclopropane]-4-yl)oxy-3-pyridyl]imidazolidine-2,4-dione;

(5R)-5-ethyl-3-{6-[(3,3,7-tri methyl-2,3-dihydro-1-benzofuran-4-yl)oxy]-3-pyridinyl}-2,4-imidazolidinedione;

(5R)-5-ethyl-3-{2-[(3,3,7-tri methyl-2,3-dihydro-1-benzofuran-4-yl)oxy]-5-pyrimidinyl}-2,4-imidazolidinedione;

(5R)-5-ethyl-5-methyl-3-[6-(7-methylspiro[2H-benzofuran-3,1'-cyclopropane]-4-yl)oxy-3-pyridyl]imidazolidine-2,4-dione;

5,5-dimethyl-3-[6-(7-methylspiro[2H-benzofuran-3,1'-cyclopropane]-4-yl)oxy-3-pyridyl]imidazolidine-2,4-dione;

or a pharmaceutically acceptable salt and/or solvate thereof and/or derivative thereof.

When Z is (Za) and W is group (Wc), suitably the compound of formula (I) is selected from:

(5R)-5-methyl-3-{4-[(3-methylphenyl)oxy]phenyl}-2,4-imidazolidinedione;

(5R)-5-methyl-3-(4-{[3-(methyloxy)phenyl]oxy}phenyl)-2,4-imidazolidinedione;

(5R)-3-(4-{[3-(ethyloxy)phenyl]oxy}phenyl)-5-methyl-2,4-imidazolidinedione;

(5R)-3-{4-[(3-chloro-5-fluorophenyl)oxy]phenyl}-5-methyl-2,4-imidazolidinedione;

(5R)-3-{4-[(3-chloro-4-fluorophenyl)oxy]phenyl}-5-methyl-2,4-imidazolidinedione;

(5S)-3-{4-[(3-chloro-4-fluorophenyl)oxy]phenyl}-5-methyl-2,4-imidazolidinedione;

(5R)-5-methyl-3-(4-{[2-methyl-5-(methyloxy)phenyl]oxy}phenyl)-2,4-imidazolidinedione;

(5R)-5-methyl-3-(4-{[4-methyl-3-(methyloxy)phenyl]oxy}phenyl)-2,4-imidazolidinedione;

(5R)-5-methyl-3-(6-{[3-(1-methylethyl)phenyl]oxy}-3-pyridinyl)-2,4-imidazolidinedione;

(5R)-5-methyl-3-[6-({3-[(1-methylethyl)oxy]phenyl}oxy)-3-pyridinyl]-2,4-imidazolidinedione;

(5R)-3-{6-[(2,5-dimethylphenyl)oxy]-3-pyridinyl}-5-methyl-2,4-imidazolidinedione;

(5R)-3-{6-[(2,3-dimethylphenyl)oxy]-3-pyridinyl}-5-methyl-2,4-imidazolidinedione;

(5R)-3-{6-[(2,6-dimethylphenyl)oxy]-3-pyridinyl}-5-methyl-2,4-imidazolidinedione;

(5R)-3-{6-[(2-ethylphenyl)oxy]-3-pyridinyl}-5-methyl-2,4-imidazolidinedione;

(5R)-5-methyl-3-(6-{[4-methyl-3-(methyloxy)phenyl]oxy}-3-pyridinyl)-2,4-imidazolidinedione;

(5R)-5-methyl-3-(6-{[2-methyl-5-(methyloxy)phenyl]oxy}-3-pyridinyl)-2,4-imidazolidinedione;

(5R)-5-methyl-3-(6-{[2-methyl-3-(methyloxy)phenyl]oxy}-3-pyridinyl)-2,4-imidazolidinedione;

(5R)-5-ethyl-3-(4-{[3-(methyloxy)phenyl]oxy}phenyl)-2,4-imidazolidinedione;

(5R)-5-ethyl-3-(6-{[4-methyl-3-(methyloxy)phenyl]oxy}-3-pyridinyl)-2,4-imidazolidinedione;

(5S)-5-ethyl-3-(6-{[4-methyl-3-(methyloxy)phenyl]oxy}-3-pyridinyl)-2,4-imidazolidinedione;

(5R)-5-ethyl-3-(6-{[3-(1-methylethyl)phenyl]oxy}-3-pyridinyl)-2,4-imidazolidinedione;

5,5-dimethyl-3-(4-{[3-(methyloxy)phenyl]oxy}phenyl)-2,4-imidazolidinedione;

3-{4-[(2,3-dimethylphenyl)oxy]phenyl}-5,5-dimethyl-2,4-imidazolidinedione;

3-{6-[(2-ethylphenyl)oxy]-3-pyridinyl}-5,5-dimethyl-2,4-imidazolidinedione;

3-{6-[(2,6-dimethylphenyl)oxy]-3-pyridinyl}-5,5-dimethyl-2,4-imidazolidinedione;

(5R)-5-(1-methylethyl)-3-(4-{[4-methyl-3-(methyloxy)phenyl]oxy}phenyl)-2,4-imidazolidinedione;

(5R)-5-methyl-3-(2-{[3-(1-methylethyl)phenyl]oxy}-5-pyrimidinyl)-2,4-imidazolidinedione;

(5R)-5-ethyl-3-(2-{[3-(ethyloxy)-4-methylphenyl]oxy}-5-pyrimidinyl)-2,4-imidazolidinedione;

(5R)-5-(1,1-dimethylethyl)-3-(6-{[4-methyl-3-(methyloxy)phenyl]oxy}-3-pyridinyl)-2,4-imidazolidinedione;

(5R)-5-ethyl-5-methyl-3-(6-{[4-methyl-3-(methyloxy)phenyl]oxy}-3-pyridinyl)-2,4-imidazolidinedione;

7-(6-{[4-methyl-3-(methyloxy)phenyl]oxy}-3-pyridinyl)-5,7-diazaspiro[3.4]octane-6,8-dione;

6-(6-{[4-methyl-3-(methyloxy)phenyl]oxy}-3-pyridinyl)-4,6-diazaspiro[2.4]heptane-5,7-dione;

4-{[5-(4,4-dimethyl-2,5-dioxo-1-imidazolidinyl)-2-pyridinyl]oxy}-2-(1-methylethyl)benzonitrile;

4-{[5-(4,4-dimethyl-2,5-dioxo-1-imidazolidinyl)-2-pyridinyl]oxy}-2-[(trifluoromethyl)oxy]benzonitrile;

3-{6-[(4-fluoro-3-methylphenyl)oxy]-3-pyridinyl}-5,5-dimethyl-2,4-imidazolidinedione;

3-{6-[(4-fluoro-2-methylphenyl)oxy]-3-pyridinyl}-5,5-dimethyl-2,4-imidazolidinedione;

5,5-dimethyl-3-(6-{[4-methyl-3-(methyloxy)phenyl]oxy}-3-pyridinyl)-2,4-imidazolidinedione;

(5R)-5-(1-methylethyl)-3-(6-{[4-methyl-3-(methyloxy)phenyl]oxy}-3-pyridinyl)-2,4-imidazolidinedione;

3-(6-{[2-(1,1-dimethylethyl)phenyl]oxy}-3-pyridinyl)-5,5-dimethyl-2,4-imidazolidinedione;

3-(2-{[2-(1,1-dimethylethyl)phenyl]oxy}-5-pyrimidinyl)-5,5-dimethyl-2,4-imidazolidinedione;

(5R)-5-ethyl-5-methyl-3-(2-{[4-methyl-3-(methyloxy)phenyl]oxy}-5-pyrimidinyl)-2,4-imidazolidinedione;

(5R)-5-ethyl-3-(2-{[3-(ethyloxy)-4-methylphenyl]oxy}-5-pyrimidinyl)-5-methyl-2,4-imidazolidinedione;

5,5-dimethyl-3-[6-({3-[(trifluoromethyl)oxy]phenyl}oxy)-3-pyridinyl]-2,4-imidazolidinedione;

4-{[5-(4,4-dimethyl-2,5-dioxo-1-imidazolidinyl)-2-pyridinyl]oxy}-3-ethylbenzonitrile;

2-chloro-4-{[5-(4,4-dimethyl-2,5-dioxo-1-imidazolidinyl)-2-pyridinyl]oxy}benzonitrile;

5,5-dimethyl-3-[6-({4-methyl-3-[(trifluoromethyl)oxy]phenyl}oxy)-3-pyridinyl]-2,4-imidazolidinedione;

4-{[5-(4,4-dimethyl-2,5-dioxo-1-imidazolidinyl)-2-pyridinyl]oxy}-2-(methyloxy)benzonitrile;

4-{[5-(4,4-dimethyl-2,5-dioxo-1-imidazolidinyl)-2-pyridinyl]oxy}-3-methylbenzonitrile;

4-{[5-(4,4-dimethyl-2,5-dioxo-1-imidazolidinyl)-2-pyridinyl]oxy}-3-(trifluoromethyl)benzonitrile;

4-{[5-(4,4-dimethyl-2,5-dioxo-1-imidazolidinyl)-2-pyridinyl]oxy}-2-ethylbenzonitrile;

4-{[5-(4,4-dimethyl-2,5-dioxo-1-imidazolidinyl)-2-pyrimidinyl]oxy}-2-ethylbenzonitrile;

3-cyclopropyl-4-{[5-(4,4-dimethyl-2,5-dioxo-1-imidazolidinyl)-2-pyridinyl]oxy}benzonitrile;

4-{[5-(4,4-dimethyl-2,5-dioxo-1-imidazolidinyl)-2-pyridinyl]oxy}-3-(1,1-dimethylethyl)benzonitrile;

2-[(cyclopropylmethyl)oxy]-4-{[5-(4,4-dimethyl-2,5-dioxo-1-imidazolidinyl)-2-pyridinyl]oxy}benzonitrile;

4-{[5-(4,4-dimethyl-2,5-dioxo-1-imidazolidinyl)-2-pyridinyl]oxy}-2-(ethyloxy)benzonitrile;

2-cyclopropyl-4-{[5-(4,4-dimethyl-2,5-dioxo-1-imidazolidinyl)-2-pyridinyl]oxy}benzonitrile;

5,5-dimethyl-3-[2-({4-methyl-3-[(trifluoromethyl)oxy]phenyl}oxy)-5-pyrimidinyl]-2,4-imidazolidinedione;

4-{[5-(4,4-dimethyl-2,5-dioxo-1-imidazolidinyl)-2-pyrimidinyl]oxy}-3-(1,1-dimethylethyl)benzonitrile;

4-{[5-(4,4-dimethyl-2,5-dioxo-1-imidazolidinyl)-2-pyridinyl]oxy}-2-[(1-methylethyl)oxy]benzonitrile;

4-({5-[(4R)-4-ethyl-4-methyl-2,5-dioxo-1-imidazolidinyl]-2-pyridinyl}oxy)-2-[(1-methylethyl)oxy]benzonitrile;

3-cyclopropyl-4-({5-[(4R)-4-ethyl-4-methyl-2,5-dioxo-1-imidazolidinyl]-2-pyridinyl}oxy)benzonitrile;

4-({5-[(4R)-4-ethyl-4-methyl-2,5-dioxo-1-imidazolidinyl]-2-pyridinyl}oxy)-2-[(trifluoromethyl)oxy]benzonitrile;

2-cyclopropyl-4-({5-[(4R)-4-ethyl-4-methyl-2,5-dioxo-1-imidazolidinyl]-2-pyridinyl}oxy)benzonitrile;

(5R)-5-ethyl-5-methyl-3-[2-({4-methyl-3-[(trifluoromethyl)oxy]phenyl}oxy)-5-pyrimidinyl]-2,4-imidazolidinedione;

3-(1,1-dimethylethyl)-4-({5-[(4R)-4-ethyl-4-methyl-2,5-dioxo-1-imidazolidinyl]-2-pyrimidinyl}oxy)benzonitrile;

3-(1,1-dimethylethyl)-4-({5-[(4R)-4-ethyl-4-methyl-2,5-dioxo-1-imidazolidinyl]-2-pyridinyl}oxy)benzonitrile;

4-{[4-(4,4-dimethyl-2,5-dioxo-1-imidazolidinyl)phenyl]oxy}-2-(methyloxy)benzonitrile;

4-{[4-(4,4-dimethyl-2,5-dioxo-1-imidazolidinyl)phenyl]oxy}-2-(ethyloxy)benzonitrile;

4-({4-[(4R)-4-ethyl-2,5-dioxo-1-imidazolidinyl]phenyl}oxy)-2-(ethyloxy)benzonitrile;

3-cyclopropyl-4-({5-[(4R)-4-ethyl-2,5-dioxo-1-imidazolidinyl]-2-pyridinyl}oxy)benzonitrile;

3-(1,1-dimethylethyl)-4-({5-[(4R)-4-ethyl-2,5-dioxo-1-imidazolidinyl]-2-pyridinyl}oxy)benzonitrile;

4-({5-[(4R)-4-ethyl-2,5-dioxo-1-imidazolidinyl]-2-pyridinyl}oxy)-2-(methyloxy)benzonitrile;

4-({4-[(4R)-4-ethyl-2,5-dioxo-1-imidazolidinyl]phenyl}oxy)-2-(methyloxy)benzonitrile;

2-[(cyclopropylmethyl)oxy]-4-({5-[(4R)-4-ethyl-2,5-dioxo-1-imidazolidinyl]-2-pyridinyl}oxy)benzonitrile;

(5R)-5-ethyl-3-[6-({4-methyl-3-[(trifluoromethyl)oxy]phenyl}oxy)-3-pyridinyl]-2,4-imidazolidinedione;

2-cyclopropyl-4-({5-[(4R)-4-ethyl-2,5-dioxo-1-imidazolidinyl]-2-pyridinyl}oxy)benzonitrile;

4-({5-[(4R)-4-ethyl-2,5-dioxo-1-imidazolidinyl]-2-pyridinyl}oxy)-2-(1-methylethyl)benzonitrile;

4-({5-[(4R)-4-ethyl-2,5-dioxo-1-imidazolidinyl]-2-pyridinyl}oxy)-2-(1-methylethyl)benzonitrile;

(5R)-5-ethyl-3-[2-({4-methyl-3-[(trifluoromethyl)oxy]phenyl}oxy)-5-pyrimidinyl]-2,4-imidazolidinedione;

4-({5-[(4R)-4-ethyl-2,5-dioxo-1-imidazolidinyl]-2-pyridinyl}oxy)-2-[(1-methylethyl)oxy]benzonitrile;

4-({5-[(4R)-4-ethyl-2,5-dioxo-1-imidazolidinyl]-2-pyridinyl}oxy)-3-methylbenzonitrile;

4-({5-[(4R)-4-ethyl-2,5-dioxo-1-imidazolidinyl]-2-pyridinyl}oxy)-2-[(trifluoromethyl)oxy]benzonitrile;

3-ethyl-4-({5-[(4R)-4-ethyl-2,5-dioxo-1-imidazolidinyl]-2-pyrimidinyl}oxy)benzonitrile;

4-({5-[(4R)-4-ethyl-2,5-dioxo-1-imidazolidinyl]-2-pyrimidinyl}oxy)-3-methylbenzonitrile;

3-(1,1-dimethylethyl)-4-({5-[(4R)-4-ethyl-2,5-dioxo-1-imidazolidinyl]-2-pyrimidinyl}oxy)benzonitrile;

4-({5-[(4R)-4-ethyl-4-methyl-2,5-dioxo-1-imidazolidinyl]-2-pyrimidinyl}oxy)-2-(1-methylethyl)benzonitrile;

or a pharmaceutically acceptable salt and/or solvate thereof and/or derivative thereof.

In particular, when Z is (Za) and W is group (Wc) the compound of formula (I) is:

(5R)-5-ethyl-5-methyl-3-[2-({4-methyl-3-[(trifluoromethyl)oxy]phenyl}oxy)-5-pyrimidinyl]-2,4-imidazolidinedione;

(5R)-5-ethyl-3-[2-({4-methyl-3-[(trifluoromethyl)oxy]phenyl}oxy)-5-pyrimidinyl]-2,4-imidazolidinedione;

5,5-dimethyl-3-[2-({4-methyl-3-[(trifluoromethyl)oxy]phenyl}oxy)-5-pyrimidinyl]-2,4-imidazolidinedione;

(5R)-5-ethyl-3-[6-({4-methyl-3-[(trifluoromethyl)oxy]phenyl}oxy)-3-pyridinyl]-2,4-imidazolidinedione 5,5-dimethyl-3-[6-({4-methyl-3-[(trifluoromethyl)oxy]phenyl}oxy)-3-pyridinyl]-2,4-imidazolidinedione (5R)-5-ethyl-3-(6-{[4-methyl-3-(methyloxy)phenyl]oxy}-3-pyridinyl)-2,4-imidazolidinedione;

or a pharmaceutically acceptable salt and/or solvate thereof and/or derivative thereof.

When Z is (Zb) and W is (Wa), suitably the compound of formula (I) is selected from:

4-{6-[(3,3-diethyl-1,3-dihydro-2-benzofuran-5-yl)oxy]pyridin-3-yl}-5-methyl-2,4-dihydro-3H-1,2,4-triazol-3-one;

4-{6-[(3-tert-butyl-1,3-dihydro-2-benzofuran-5-yl)oxy]pyridin-3-yl}-5-methyl-2,4-dihydro-3H-1,2,4-triazol-3-one (enantiomer 1);

4-{6-[(3-tert-butyl-1,3-dihydro-2-benzofuran-5-yl)oxy]pyridin-3-yl}-5-methyl-2,4-dihydro-3H-1,2,4-triazol-3-one (enantiomer 2);

5-methyl-4-(6-{[3-methyl-3-(trifluoromethyl)-1,3-dihydro-2-benzofuran-5-yl]oxy}pyridin-3-yl)-2,4-dihydro-3H-1,2,4-triazol-3-one (enantiomer 1);

5-methyl-4-(6-{[3-methyl-3-(trifluoromethyl)-1,3-dihydro-2-benzofuran-5-yl]oxy}pyridin-3-yl)-2,4-dihydro-3H-1,2,4-triazol-3-one (enantiomer 2);

5-methyl-4-[6-(3H-spiro[2-benzofuran-1,1'-cyclobutan]-6-yloxy)pyridin-3-yl]-2,4-dihydro-3H-1,2,4-triazol-3-one;

5-methyl-4-[6-(3H-spiro[2-benzofuran-1,1'-cyclopentan]-6-yloxy)pyridin-3-yl]-2,4-dihydro-3H-1,2,4-triazol-3-one;

or a pharmaceutically acceptable salt and/or solvate thereof and/or derivative thereof.

When Z is (Zb) and W is (Wb), suitably the compound of formula (I) is selected from:

4-{6-[(3,3-dimethyl-2,3-dihydro-1-benzofuran-4-yl)oxy]pyridin-3-yl}-5-methyl-2,4-dihydro-3H-1,2,4-triazol-3-one;

4-{6-[(3-tert-butyl-1,3-dihydro-2-benzofuran-4-yl)oxy]pyridin-3-yl}-5-methyl-2,4-dihydro-3H-1,2,4-triazol-3-one 5-methyl-4-{6-[(3,3,7-tri methyl-2,3-dihydro-1-benzofuran-4-yl)oxy]-3-pyridinyl}-2,4-dihydro-3H-1,2,4-triazol-3-one;

4-{6-[(3,3-dimethyl-2,3-dihydro-1-benzofuran-4-yl)oxy]-5-methylpyridin-3-yl}-5-methyl-2,4-dihydro-3H-1,2,4-triazol-3-one;

5-methyl-4-[5-methyl-6-(spiro[1-benzofuran-3,1'-cyclopropan]-4-yloxy)pyridin-3-yl]-2,4-dihydro-3H-1,2,4-triazol-3-one;

5-methyl-4-{5-methyl-6-[(7-methylspiro[1-benzofuran-3,1'-cyclopropan]-4-yl)oxy]pyridin-3-yl}-2,4-dihydro-3H-1,2,4-triazol-3-one;

5-methyl-4-{6-[(7-methylspiro[1-benzofuran-3,1'-cyclopropan]-4-yl)oxy]pyridin-3-yl}-2,4-dihydro-3H-1,2,4-triazol-3-one;

5-methyl-4-[6-(spiro[1-benzofuran-3,1'-cyclopropan]-4-yloxy)pyridin-3-yl]-2,4-dihydro-3H-1,2,4-triazol-3-one; and 5-methyl-4-{2-[(7-methylspiro[1-benzofuran-3,1'-cyclopropan]-4-yl)oxy]pyrimidin-5-yl}-2,4-dihydro-3H-1,2,4-triazol-3-one;

or a pharmaceutically acceptable salt and/or solvate thereof and/or derivative thereof.

In particular, when Z is (Zb) and W is group (Wb) the compound of formula (I) is:

5-methyl-4-{6-[(7-methylspiro[1-benzofuran-3,1'-cyclopropan]-4-yl)oxy]pyridin-3-yl}-2,4-dihydro-3H-1,2,4-triazol-3-one;

5-methyl-4-[6-(spiro[1-benzofuran-3,1'-cyclopropan]-4-yloxy)pyridin-3-yl]-2,4-dihydro-3H-1,2,4-triazol-3-one;

or a pharmaceutically acceptable salt and/or solvate thereof and/or derivative thereof.

When Z is (Zb) and W is (Wd), suitably the compound of formula (I) is selected from:

5-methyl-4-(4-{[4-methyl-3-(methyloxy)phenyl]oxy}phenyl)-2,4-dihydro-3H-1,2,4-triazol-3-one;

5-methyl-4-(4-{[3-(methyloxy)phenyl]oxy}phenyl)-2,4-dihydro-3H-1,2,4-triazol-3-one;

4-{4-[(3-ethylphenyl)oxy]phenyl}-5-methyl-2,4-dihydro-3H-1,2,4-triazol-3-one;

4-{4-[(2,6-dimethylphenyl)oxy]phenyl}-5-methyl-2,4-dihydro-3H-1,2,4-triazol-3-one;

4-(4-{[4-chloro-3-(methyloxy)phenyl]oxy}phenyl)-5-methyl-2,4-dihydro-3H-1,2,4-triazol-3-one;

4-(4-{[4-fluoro-3-(methyloxy)phenyl]oxy}phenyl)-5-methyl-2,4-dihydro-3H-1,2,4-triazol-3-one;

4-{4-[(3-chlorophenyl)oxy]phenyl}-5-methyl-2,4-dihydro-3H-1,2,4-triazol-3-one;

4-{4-[(3,4-dichlorophenyl)oxy]phenyl}-5-methyl-2,4-dihydro-3H-1,2,4-triazol-3-one;

4-{4-[(2,4-dichlorophenyl)oxy]phenyl}-5-methyl-2,4-dihydro-3H-1,2,4-triazol-3-one;

4-{4-[(3-chloro-2-fluorophenyl)oxy]phenyl}-5-methyl-2,4-dihydro-3H-1,2,4-triazol-3-one;

4-(4-{[3-chloro-5-(methyloxy)phenyl]oxy}phenyl)-5-methyl-2,4-dihydro-3H-1,2,4-triazol-3-one;

5-methyl-4-[4-({3-[(trifluoromethyl)oxy]phenyl}oxy)phenyl]-2,4-dihydro-3H-1,2,4-triazol-3-one;

4-{4-[(3-methylphenyl)oxy]phenyl}-5-methyl-2,4-dihydro-3H-1,2,4-triazol-3-one;

5-methyl-4-(4-{[3-(trifluoromethyl)phenyl]oxy}phenyl)-2,4-dihydro-3H-1,2,4-triazol-3-one;

4-{4-[(3-chloro-4-fluorophenyl)oxy]phenyl}-5-methyl-2,4-dihydro-3H-1,2,4-triazol-3-one;

4-{4-[(3-chloro-5-fluorophenyl)oxy]phenyl}-5-methyl-2,4-dihydro-3H-1,2,4-triazol-3-one;

4-{4-[(2,3-dimethylphenyl)oxy]phenyl}-5-methyl-2,4-dihydro-3H-1,2,4-triazol-3-one;

5-methyl-4-(4-{[2-methyl-5-(methyloxy)phenyl]oxy}phenyl)-2,4-dihydro-3H-1,2,4-triazol-3-one;

4-{4-[(3,4-dimethylphenyl)oxy]phenyl}-5-methyl-2,4-dihydro-3H-1,2,4-triazol-3-one;

4-{4-[(3,5-dimethylphenyl)oxy]phenyl}-5-methyl-2,4-dihydro-3H-1,2,4-triazol-3-one;

4-{4-[(2,5-dimethylphenyl)oxy]phenyl}-5-methyl-2,4-dihydro-3H-1,2,4-triazol-3-one;

5-methyl-4-{4-[(2-methylphenyl)oxy]phenyl}-2,4-dihydro-3H-1,2,4-triazol-3-one;

4-{4-[(2-ethylphenyl)oxy]phenyl}-5-methyl-2,4-dihydro-3H-1,2,4-triazol-3-one;

5-methyl-4-(4-{[3-(1-methylethyl)phenyl]oxy}phenyl)-2,4-dihydro-3H-1,2,4-triazol-3-one;

4-(4-{[3-(dimethylamino)phenyl]oxy}phenyl)-5-methyl-2,4-dihydro-3H-1,2,4-triazol-3-one;

4-{4-[(2-fluoro-6-methylphenyl)oxy]phenyl}-5-methyl-2,4-dihydro-3H-1,2,4-triazol-3-one;

5-methyl-4-(4-{[2-methyl-3-(methyloxy)phenyl]oxy}phenyl)-2,4-dihydro-3H-1,2,4-triazol-3-one;

4-(4-{[3-(ethyloxy)phenyl]oxy}phenyl)-5-methyl-2,4-dihydro-3H-1,2,4-triazol-3-one;

4-{4-[(3-methylphenyl)oxy]phenyl}-2,4-dihydro-3H1,2,4-triazol-3-one;

4-(4-{[3-trifluoromethyl)phenyl]oxy}phenyl)-2,4-dihydro-3H-1,2,4-triazol-3-one;

4-[4-[4-fluoro-3-(trifluoromethoxy)phenoxy]phenyl]-3-methyl-1H-1,2,4-triazol-5-one;

5-methyl-4-(5-methyl-6-{[3-(1-methylethyl)phenyl]oxy}-3-pyridinyl)-2,4-dihydro-3H-1,2,4-triazol-3-one;

4-(6-{[3-(ethyloxy)phenyl]oxy}-5-methyl-3-pyridinyl)-5-methyl-2,4-dihydro-3H-1,2,4-triazol-3-one;

4-{6-[(2,3-dimethylphenyl)oxy]-3-pyridinyl}-5methly-2,4-dihydro-3H-1,2,4-triazol-3-one;

4-(6-{[3-(1-methylethyl)phenyl]oxy}-3-pyridinyl)-2,4-dihydro-3H-1,2,4-triazol-3-one;

5-methyl-4-(6-{[3-(1-methylethyl)phenyl]oxy}-3-pyridinyl)-2,4-dihydro-3H-1,2,4-triazol-3-one;

4-(6-{[2-(1,1-dimethylethyl)phenyl]oxy}-3-pyridinyl)-5-methyl-2,4,dihydro-3H-1,2,4trazol-3-one;

5-methyl-4-{6-[4-methyl-3-(trifluoromethoxy)phenoxy]pyridin-3-yl}-2,4-dihydro-3H-1,2,4-triazol-3-one;

or a pharmaceutically acceptable salt and/or solvate thereof and/or derivative thereof.

Suitably, the compound of formula (I) is not a pharmaceutically acceptable salt (or not any salt).

Suitably, the compound of formula (I) is not a solvate.

Suitably, the compound of formula (I) is not a derivative.

In respect of the specifically mentioned compounds listed above, the terms enantiomer 1, enantiomer 2, diastereomer 1 and diastereomer 2 refer to the particular enantiomer or disasteriomers named accordingly and described in the original disclosures of these compounds (see WO2011/069951, WO2012/076877, WO2012/168710, WO2013/175215, WO2013/083994 and WO2013/182850, which are incorporated herein by reference for the purposes of providing compounds of use in the present invention).

For the avoidance of doubt, the embodiments of any one feature of the compounds of the invention may be combined with any embodiment of another feature of compounds of the invention to create a further embodiment.

The term 'halo' or 'halogen' as used herein, refers to a fluorine, chlorine, bromine or iodine atom. Particular examples of halo are fluorine and chlorine, especially fluorine.

When the compound contains a $C_{1-4}$alkyl group, whether alone or forming part of a larger group, e.g. $C_{1-4}$alkoxy, the alkyl group may be straight chain, branched, cyclic, or a combination thereof. Examples of $C_{1-4}$alkyl are methyl, ethyl, n-propyl, isopropyl, n-butyl, isobutyl, sec-butyl, tert-butyl, cyclopropyl and cyclobutyl. A particular group of exemplary $C_{1-4}$alkyl groups are methyl, ethyl, n-propyl, isopropyl, n-butyl, isobutyl, sec-butyl, tert-butyl. An example of $C_{1-4}$alkoxy is methoxy.

The term 'halo$C_{1-4}$alkyl' as used herein, includes straight chain, branched chain or cyclic alkyl groups containing 1 to 4 carbon atoms substituted by one or more halo atoms, for example fluoromethyl, difluoromethyl and trifluoromethyl. A particular group of exemplary halo$C_{1-4}$ alkyl include methyl and ethyl groups substituted with one to three halo atoms, in particular one to three fluoro atoms, such as trifluoromethyl or 2,2,2-trifluoroethyl.

The term 'halo$C_{1-4}$alkoxy' as used herein, includes straight chain, branched chain or cyclic alkoxy groups containing 1 to 4 carbon atoms substituted by one or more halo atoms, for example fluoromethoxy, difluoromethoxy and trifluoromethoxy. A particular group of exemplary haloC$_{1-4}$ alkyl include methoxy and ethoxy groups substituted with one to three halo atoms, in particular one to three fluoro atoms.

The term '5 or 6 membered saturated or unsaturated heterocycle, with at least one O atom' includes for example dihydrofuran, dihydropyran, furan, pyran, oxazole, isoxazole, oxazine, dioxine, morpholine or 1,3-dioxalane.

It will be appreciated that for use in medicine the salts of the compounds of formula (I) should be pharmaceutically acceptable. Suitable pharmaceutically acceptable salts will be apparent to those skilled in the art. Pharmaceutically acceptable salts include those described by Berge et al., 1977. Such pharmaceutically acceptable salts include acid addition salts formed with inorganic acids e.g. hydrochloric, hydrobromic, sulphuric, nitric or phosphoric acid and organic acids e.g. succinic, maleic, acetic, fumaric, citric, tartaric, benzoic, p-toluenesulfonic, methanesulfonic or naphthalenesulfonic acid. Other salts e.g. oxalates or formates, may be used, for example in the isolation of compounds of formula (I) and are included within the scope of this invention.

Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form and, if crystalline, may optionally be solvated, e.g. as the hydrate. This invention includes within its scope stoichiometric solvates (e.g. hydrates) as well as compounds containing variable amounts of solvent (e.g. water).

It will be understood that the invention includes pharmaceutically acceptable derivatives of compounds of formula (I) for use in the prophylaxis or treatment of pain, a method of prophylaxis or treatment of pain by administering a derivative of a compound of formula (I), and the use of a derivative of a compound of formula (I) in the manufacture of a medicament for the prophylaxis or treatment of pain.

As used herein "pharmaceutically acceptable derivative" includes any pharmaceutically acceptable prodrug such as an ester or salt of such ester of a compound of formula (I) which, upon administration to the recipient is capable of providing (directly or indirectly) a compound of formula (I) or an active metabolite or residue thereof.

Suitably, a pharmaceutically acceptable prodrug is formed by functionalising the secondary nitrogen of the hydantoin or triazolone, for example with a group "L" as illustrated in each Z group below:

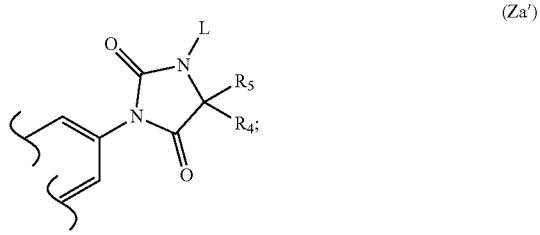

(Za')

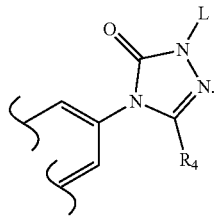

(Zb')

A compound of formula (I) may be functionalised via the secondary nitrogen of the hydantoin or triazolone with a group L, wherein L is selected from:
a) —PO(OH)O$^-$.M, wherein M$^+$ is a pharmaceutically acceptable monovalent counterion,
b) —PO(O$^-$)$_2$.2M$^+$,
c) —PO(O$^-$)$_2$.D$^{2+}$, wherein D$^{2+}$ is a pharmaceutically acceptable divalent counterion,
d) —CH(R$^X$)—PO(OH)O$^-$.M$^+$, wherein R$^X$ is hydrogen or C$_{1-3}$ alkyl,
e) —CH(R$^X$)—PO(O$^-$)$_2$.2M$^+$,
f) —CH(R$^X$)—PO(O$^-$)$_2$.D$^{2+}$
g) —SO$_3$$^-$.M$^+$,
h) —CH(R$^X$)—SO$_3$$^-$.M$^+$, and
i) —CO—CH$_2$CH$_2$—CO$_2$.M$^+$.

All isomers of formula (I) and their pharmaceutically acceptable derivatives, including all geometric, tautomeric and optical forms, and mixtures thereof (e.g. racemic mixtures) are contemplated for the uses and method of the invention. Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

Isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment") are also contemplated for the uses and method of the invention. Examples of isotopes that can be incorporated into compounds of the invention include isotopes of hydrogen, carbon, nitrogen, oxygen, fluorine, iodine and chlorine such as $^2$H (deuterium), $^3$H, $^{11}$C, $^{13}$C, $^{14}$C, $^{18}$F, $^{123}$I or $^{125}$I, which may be naturally occurring or non-naturally occurring isotopes. Unless isotopic enrichment is required, suitably the isotope content of the compound of formula (I) is not altered from that commonly found in nature.

Compounds of formula (I) and pharmaceutically acceptable salts of said compounds that contain the aforementioned isotopes and/or other isotopes of other atoms are contemplated for use for the uses and method of the present invention. Isotopically labelled compounds of the present invention, for example those into which radioactive isotopes such as $^3$H or $^{14}$C have been incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

In general, the compounds of formula (I) may be made according to the organic synthesis techniques known to those skilled in this field, as well as by the representative methods set forth below, those in the Examples, and modifications thereof.

Compounds of formula (I), and salts and solvates thereof wherein W is group (Wa) may be prepared by the general methods outlined in WO2012/168710.

Compounds of formula (I), and salts and solvates thereof wherein W is group (Wb) may be prepared by the general methods outlined in WO2012/076877.

Compounds of formula (I), and salts and solvates thereof wherein W is group (Wc) may be prepared by the general methods outlined in WO2011/069951.

Compounds of formula (I), and salts and solvates thereof wherein W is group (Wd) may be prepared by the general methods outlined in WO 2013/175215.

Certain compounds of formula (I) wherein W is group (Wb) may also be prepared by the following method or analogous approaches:

Scheme 1

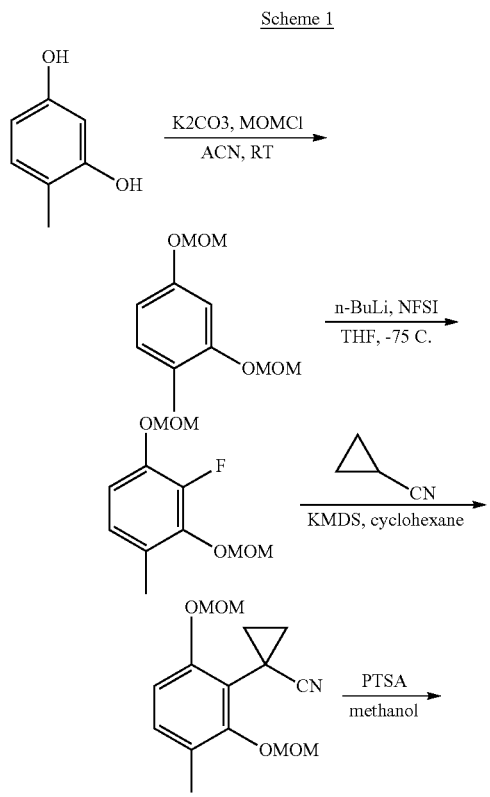

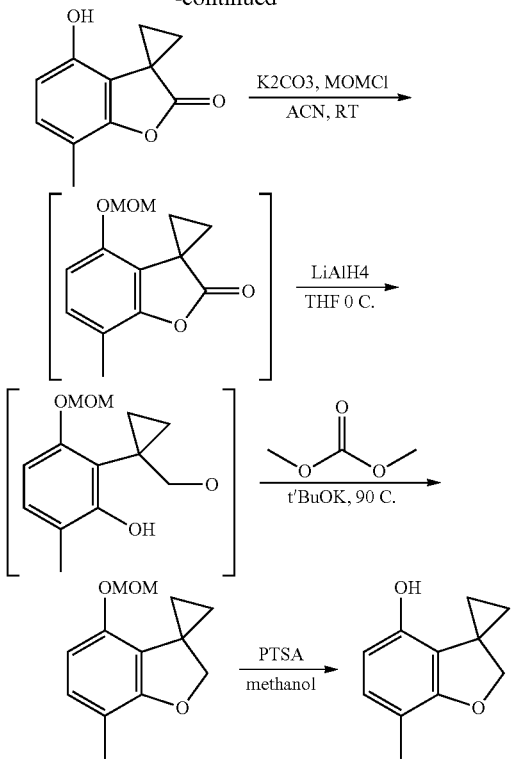

Consequently, the present invention provides the novel compounds:

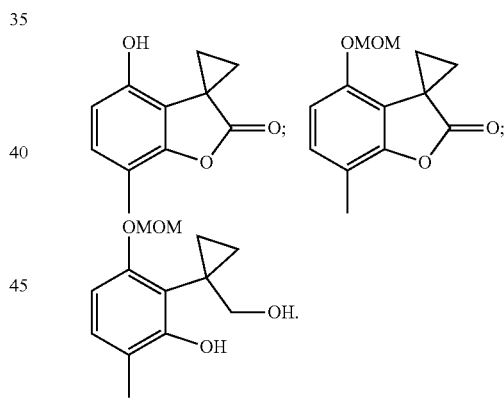

The present invention provides a modulator of Kv3.1 and/or Kv3.2 and/or Kv3.3 channels for use in the prophylaxis or treatment of pain wherein the modulator of Kv3.1 and/or Kv3.2 and/or Kv3.3 channels is a compound of formula (I) or a pharmaceutically acceptable salt and/or solvate thereof and/or derivative thereof, as defined above.

The present invention further provides the use of a modulator of Kv3.1 and/or Kv3.2 and/or Kv3.3 channels in the manufacture of a medicament for the prophylaxis or treatment of pain wherein the modulator of Kv3.1 and/or Kv3.2 and/or Kv3.3 channels is a compound of formula (I) or a pharmaceutically acceptable salt and/or solvate thereof and/or derivative thereof, as defined above.

The present invention also provides a method of prophylaxis or treatment of pain by administering a modulator of Kv3.1 and/or Kv3.2 and/or Kv3.3 channels wherein the modulator of Kv3.1 and/or Kv3.2 and/or Kv3.3 channels is a compound of formula (I) or a pharmaceutically acceptable salt and/or solvate thereof and/or derivative thereof, as defined above.

Modulators of Kv3.1 and/or Kv3.2 and/or Kv3.3 Channels

A 'modulator' as used herein refers to a compound which is capable of producing at least 20% potentiation of whole-cell currents mediated by human Kv3.1 and/or human Kv3.2 and/or human Kv3.3 channels recombinantly expressed in mammalian cells. Compounds of the invention may be tested in an assay such as provided in Example 1 to determine their modulatory properties.

In one embodiment the modulator is capable of producing at least 20% potentiation of whole-cell currents mediated by human Kv3.1 channels recombinantly expressed in mammalian cells. Suitably the $pEC_{50}$ of the modulator is in the range of 4-7 (such as 5-6.5).

In one embodiment the modulator is capable of producing at least 20% potentiation of whole-cell currents mediated by human Kv3.2 channels recombinantly expressed in mammalian cells. Suitably the $pEC_{50}$ of the modulator is in the range of 4-7 (such as 5-6.5).

In one embodiment the modulator is capable of producing at least 20% potentiation of whole-cell currents mediated by human Kv3.3 channels recombinantly expressed in mammalian cells. Suitably the $pEC_{50}$ of the modulator is in the range of 4-7 (such as 5-6.5).

In another embodiment the modulator is capable of producing at least 20% potentiation of whole-cell currents mediated by human Kv3.1 and Kv3.2 channels recombinantly expressed in mammalian cells.

In another embodiment the modulator is capable of producing at least 20% potentiation of whole-cell currents mediated by human Kv3.1 and Kv3.3 channels recombinantly expressed in mammalian cells.

In another embodiment the modulator is capable of producing at least 20% potentiation of whole-cell currents mediated by human Kv3.2 and Kv3.3 channels recombinantly expressed in mammalian cells.

In a further embodiment the modulator is capable of producing at least 20% potentiation of whole-cell currents mediated by human Kv3.1, Kv3.2 and Kv3.3 channels recombinantly expressed in mammalian cells.

In one embodiment of the invention the modulator (such as the compound of formula (I) or a pharmaceutically acceptable salt and/or solvate and/or derivative) is selective for modulation of Kv3.1 channels over modulation of Kv3.2 channels. By selective, it is meant that the modulator demonstrates, for example, at least a 2 fold, 5 fold or 10 fold activity for Kv3.1 channels than for Kv3.2 channels. The activity of a modulator is suitably quantified by its potency as indicated by an $EC_{50}$ value.

In another embodiment of the invention the modulator (such as a compound of formula (I) or a pharmaceutically acceptable salt and/or solvate and/or derivative) is selective for modulation of Kv3.2 channels over modulation of Kv3.1 channels. Once again, by selective it is meant that the modulator demonstrates, for example at least a 2 fold, 5 fold or 10 fold activity for Kv3.2 channels than for Kv3.1 channels. Compounds of formula (I) or their pharmaceutically acceptable salts and/or solvates wherein W is Wb and $R_1$ is H may demonstrate greater activity for the Kv3.2 channel over the Kv3.1 channel. Example 15 disclosed in WO2013/175215 is a compound of the invention which demonstrates selectivity for Kv3.2 channels.

In one embodiment of the invention the modulator (such as the compound of formula (I) or a pharmaceutically acceptable salt and/or solvate and/or derivative) is selective for modulation of Kv3.1 channels over modulation of Kv3.3 channels. By selective, it is meant that the modulator demonstrates, for example, at least a 2 fold, 5 fold or 10 fold activity for Kv3.1 channels than for Kv3.3 channels. The activity of a modulator is suitably quantified by its potency as indicated by an $EC_{50}$ value.

In another embodiment of the invention the modulator (such as a compound of formula (I) or a pharmaceutically acceptable salt and/or solvate and/or derivative) is selective for modulation of Kv3.3 channels over modulation of Kv3.1 channels. Once again, by selective it is meant that the modulator demonstrates, for example at least a 2 fold, 5 fold or 10 fold activity for Kv3.3 channels than for Kv3.1 channels. The activity of a modulator is suitably quantified by its potency as indicated by an $EC_{50}$ value.

In one embodiment of the invention the modulator (such as the compound of formula (I) or a pharmaceutically acceptable salt and/or solvate and/or derivative) is selective for modulation of Kv3.2 channels over modulation of Kv3.3 channels. By selective, it is meant that the modulator demonstrates, for example, at least a 2 fold, 5 fold or 10 fold activity for Kv3.2 channels than for Kv3.3 channels. The activity of a modulator is suitably quantified by its potency as indicated by an $EC_{50}$ value.

In another embodiment of the invention the modulator (such as a compound of formula (I) or a pharmaceutically acceptable salt and/or solvate and/or derivative) is selective for modulation of Kv3.3 channels over modulation of Kv3.2 channels. Once again, by selective it is meant that the modulator demonstrates, for example at least a 2 fold, 5 fold or 10 fold activity for Kv3.3 channels than for Kv3.2 channels. The activity of a modulator is suitably quantified by its potency as indicated by an $EC_{50}$ value.

In a further embodiment of the invention the modulator (such as a compound of formula (I) or a pharmaceutically acceptable salt and/or solvate and/or derivative) demonstrates comparable activity between modulation of Kv3.1 and Kv3.2 channels, for example the activity for one channel is less than 2 fold that for the other channel, such as less than 1.5 fold or less than 1.2 fold. Compounds of formula (I) or their pharmaceutically acceptable salts and/or solvates wherein W is Wb, $R_1$ is $C_{1-4}$alkyl, in particular methyl, in the para position may demonstrate comparable activity between modulation of Kv3.1 and Kv3.2 channels. Compound 3 is a compound of the invention which demonstrates a comparable activity between modulation of Kv3.1 and Kv3.2 channels. The activity of a modulator is suitably quantified by its potency as indicated by an $EC_{50}$ value.

In a further embodiment of the invention the modulator (such as a compound of formula (I) or a pharmaceutically acceptable salt and/or solvate and/or derivative) demonstrates comparable activity between modulation of Kv3.1 and Kv3.3 channels, for example the activity for one channel is less than 2 fold that for the other channel, such as less than 1.5 fold or less than 1.2 fold. The activity of a modulator is suitably quantified by its potency as indicated by an $EC_{50}$ value.

In a further embodiment of the invention the modulator (such as a compound of formula (I) or a pharmaceutically acceptable salt and/or solvate and/or derivative) demonstrates comparable activity between modulation of Kv3.2 and Kv3.3 channels, for example the activity for one channel is less than 2 fold that for the other channel, such as less than 1.5 fold or less than 1.2 fold. The activity of a modulator is suitably quantified by its potency as indicated by an $EC_{50}$ value.

Suitably the modulator of Kv3.1 and/or Kv3.2 and/or Kv3.3 is selective over other channels which have been associated with pain. For example, while the modulator of Kv3.1 and/or Kv3.2 and/or Kv3.3 is capable of providing an increase of whole-cell currents of, on average, at least 20% of the increase observed with 50 micromolar N-cyclohexyl-N-[(7,8-dimethyl-2-oxo-1,2-dihydro-3-quinolinyl)methyl]-N'-phenylurea, the modulator of Kv3.1 and/or Kv3.2 and/or Kv3.3 does not have a notable effect on Kv3.4, Kv7.2/7.3, and/or Nav 1.7 currents. The Examples herein provide suitable methods for the testing of Kv3.1, Kv3.2, Kv3.3, Kv 3.4, Kv7.2/7.3, and Nav 1.7 currents.

In one embodiment the modulator of Kv3.1 and/or Kv3.2 and/or Kv3.3 is selective over Kv3.4. Namely, the modulator of Kv3.1 and/or Kv3.2 and/or Kv3.3 is capable of providing an increase of Kv3.1 and/or Kv3.2 and/or Kv3.3 whole-cell currents of, on average, at least 20% of the increase observed with 50 micromolar N-cyclohexyl-N-[(7,8-dimethyl-2-oxo-1,2-dihydro-3-quinolinyl)methyl]-N'-phenylurea but provides an increase of less than 10% (such as less than 5%, especially less than 1% or suitably no increase) in Kv3.4 current at the same concentration (e.g. 10 uM).

In one embodiment the modulator of Kv3.1 and/or Kv3.2 and/or Kv3.3 is selective over Kv7.2/7.3. Namely, the modulator of Kv3.1 and/or Kv3.2 and/or Kv3.3 is capable of providing an increase of Kv3.1 and/or Kv3.2 and/or Kv3.3 whole-cell currents of, on average, at least 20% of the increase observed with 50 micromolar N-cyclohexyl-N-[(7,8-dimethyl-2-oxo-1,2-dihydro-3-quinolinyl)methyl]-N'-phenylurea but provides an increase of less than 10% (such as less than 5%, especially less than 1% or suitably no increase) in Kv7.2/7.3 current at the same concentration (e.g. 10 uM).

In one embodiment the modulator of Kv3.1 and/or Kv3.2 and/or Kv3.3 is selective over Nav1.7. Namely, the modulator of Kv3.1 and/or Kv3.2 and/or Kv3.3 is capable of providing an increase of Kv3.1 and/or Kv3.2 and/or Kv3.3 whole-cell currents of, on average, at least 20% of the increase observed with 50 micromolar N-cyclohexyl-N-[(7,8-dimethyl-2-oxo-1,2-dihydro-3-quinolinyl)methyl]-N'-phenylurea but provides an increase of less than 10% (such as less than 5%, especially less than 1% or suitably no increase) in Nav1.7 current at the same concentration (e.g. 10 uM).

Pain Indications

The term "treatment" or "treating" as used herein includes the control, mitigation, reduction, or modulation of the disease state or its symptoms.

The term "prophylaxis" is used herein to mean preventing symptoms of a disease or disorder in a subject or preventing recurrence of symptoms of a disease or disorder in an afflicted subject and is not limited to complete prevention of an affliction.

In one embodiment of the invention, pain that may be mediated by a modulator of Kv3.1 and/or Kv3.2 and/or Kv3.3 channels is chronic pain. In another embodiment of the invention, pain is acute pain.

In an embodiment of the invention, the pain indications that may be mediated by a modulator of Kv3.1 and/or Kv3.2 and/or Kv3.3 channels is nociceptive, neuropathic, inflammatory or miscellaneous pain.

Nociceptive pain represents the normal response to noxious insult or injury of tissues such as skin, muscles, visceral organs, joints, tendons, or bones. Examples of nociceptive pain which form part of the invention include somatic pain: musculoskeletal (joint pain, myofascial pain) or cutaneous, which is often well localized; or visceral pain: hollow organs or smooth muscle.

Neuropathic pain is pain initiated or caused by a primary lesion or disease in the somatosensory nervous system. Sensory abnormalities range from deficits perceived as paraesthesia (numbness) to hypersensitivity (hyperalgesia or allodynia), and dysaesthesia (tingling and other sensations). Examples of neuropathic pain which form part of the invention include, but are not limited to, diabetic neuropathy, post-herpetic neuralgia, spinal cord injury pain, phantom limb (post-amputation) pain, and post-stroke central pain. Other causes of neuropathic pain include trauma, chemotherapy and heavy metal exposure.

Inflammatory pain occurs as a result of activation and sensitization of the nociceptive pain pathway by a variety of mediators released at a site of tissue inflammation. Mediators that have been implicated as key players in inflammatory pain are pro-inflammatory cytokines such IL-1-alpha, IL-1-beta, IL-6 and TNF-alpha, chemokines, reactive oxygen species, vasoactive amines, lipids, ATP, acid, and other factors released by infiltrating leukocytes, vascular endothelial cells, or tissue resident mast cells. Examples causes of inflammatory pain which form part of the invention include appendicitis, rheumatoid arthritis, inflammatory bowel disease, and herpes zoster.

Miscellaneous pain refers to pain conditions or disorders which are not easily classifiable. The current understanding of their underlying mechanisms is still rudimentary though specific therapies for those disorders are well known; they include cancer pain, migraine and other primary headaches and wide-spread pain of the fibromyalgia type.

Suitably, specific pain indications that may be mediated by a modulator of Kv3.1 and/or Kv3.2 and/or Kv3.3 channels are neuropathic pain and/or inflammatory pain.

The neuropathic pain that may be ameliorated by a modulator of Kv3.1 and/or Kv3.2 and/or Kv3.3 channels may be central or peripheral neuropathic pain. Central neuropathic pain is caused by damage to or dysfunction of the central nervous system (CNS), which includes but is not limited to the brain, brainstem, and spinal cord. Peripheral neuropathic pain is caused by damage to or dysfunction of the peripheral nervous system, which includes but is not limited to sensory nerves, motor nerves and autonomic nerves. In one embodiment, the neuropathic pain is central neuropathic pain. In another embodiment, the neuropathic pain is peripheral neuropathic pain.

Pain is a subjective condition and in a clinical setting tends to be measured by a patient's self-assessment. Therefore, it can be difficult to measure and quantify pain threshold. For chronic pain, typically a subjective 11-point rating scale is used where 0 is no pain and 10 is the worst pain imaginable. Subjects generally record their worst pain over a given period, usually a day. A minimum mean baseline score is also recorded and response to the medication is measured relative to the baseline, for example, a reduction of at least 10%, 20%, 30%, 40% or 50% in pain from the baseline score may be observed.

Since individual responses to medicaments may vary, not all individuals may experience a reduction in pain from the baseline score. Consequently, suitably a reduction is observed in at least at least 10%, 20%, 30%, 40%, 50%, 60%, 70%, 80%, 90% or all individuals tested.

Therefore, in one embodiment of the invention, a reduction of at least 10%, 20%, 30%, 40% or 50% in pain from the baseline score is observed upon administration of a Kv3.1/Kv3.2/Kv3.3 modulator, such as a compound of formula (I) or a pharmaceutically acceptable salt, solvate and/or derivative thereof to a subject in need thereof.

Administration of a Kv3.1/Kv3.2/Kv3.3 modulator can occur before an anticipated onset of pain or after the onset of pain. In cases where it is anticipated that development of a disease or disorder may lead to an increase in pain experienced by the subject, a Kv3.1/Kv3.2/Kv3.3 modulator, such as a compound of formula (I) or a pharmaceutically acceptable salt, solvate and/or derivative thereof can be administered. In cases where a subject is already experiencing pain, a Kv3.1/Kv3.2/Kv3.3 modulator, such as a compound of formula (I) or a pharmaceutically acceptable salt, solvate and/or derivative thereof may be administered to a subject in need thereof.

Treatment of the subject in need thereof may continue for as long as treatment is required, for example, 1 day, 1 week, 2 weeks, 3 weeks, 1 month, 6 months, 1 year, more than 1 year more than 2 years, more than 5 years or more than 10 years. Therefore in one embodiment of the invention, a therapeutically effective amount of a Kv3.1/Kv3.2/Kv3.3 modulator, such as a compound of formula (I) or a pharmaceutically acceptable salt, solvate and/or derivative thereof, is administered to a subject in need thereof for 1 day to 1 month, 1 week to 3 months, 1 month to 6 months, 3 months to 1 year or more than 1 year.

Reduction in pain in a subject can be measured by assessing the response to an external stimuli such as mechanical or thermal (e.g. cold) stimuli (such as described in the Experimental section). The reduction can either be considered as a percentage reversal (calculated by measuring the pre- and post-dose thresholds of the affected pain site with a non-affected pain site, such as described in more detail under Data Analysis in the Experimental Section) or by measuring withdrawal thresholds of the affected pain site. Preferably, the percentage reversal calculation is used.

Therefore, in one embodiment of the invention, the sensitivity to pain (such as neuropathic pain or inflammatory pain) is reversed by more than 20%, more than 30%, more than 40%, more than 50%, more than 60%, more than 70%, more than 80% or more than 90%, upon administration of a therapeutically effective amount of a Kv3.1/Kv3.2/Kv3.3 modulator, such as a compound of formula (I) or a pharmaceutically acceptable salt, solvate and/or derivative thereof. Suitably, the sensitivity to pain is reversed by more than 80% or more than 90%.

Subjects receiving the Kv3.1/Kv3.2/Kv3.3 modulator may experience secondary benefits, such as one or more of improved function, mood, sleep, quality of life, reduced time off work.

Suitably, the prophylaxis or treatment of pain does not include the prophylaxis or treatment of sleep disorder due to neuropathic pain. Suitably, the prophylaxis or treatment of pain does not include the prophylaxis or treatment of sleep disorder due to pain.

Administration

For use in therapy the modulators are usually administered as a pharmaceutical composition. The invention also provides a pharmaceutical composition comprising a modulator of Kv3.1 and/or Kv3.2 and/or Kv3.3 (such as a compound of formula (I), or a pharmaceutically acceptable salt and/or solvate and/or derivative thereof), and a pharmaceutically acceptable carrier.

The modulator of Kv3.1 and/or Kv3.2 and/or Kv3.3 may be administered by any convenient method, e.g. by oral, parenteral, buccal, sublingual, nasal, rectal, intrathecal or transdermal administration, and the pharmaceutical compositions adapted accordingly.

A modulator of Kv3.1 and/or Kv3.2 and/or Kv3.3 which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochlorohydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches. In one embodiment the composition is in unit dose form such as a tablet, capsule or ampoule.

The composition may contain from 0.1% to 100% by weight, for example from 10 to 60% by weight, of the active material, depending on the method of administration. The composition may contain from 0% to 99% by weight, for example 40% to 90% by weight, of the carrier, depending on the method of administration. The composition may contain from 0.05 mg to 1000 mg, for example from 1.0 mg to 500 mg, of the active material, depending on the method of administration. The composition may contain from 50 mg to 1000 mg, for example from 100 mg to 400 mg of the carrier, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 500 mg, and such unit doses may be administered more than once a day, for example two or three a day. Such therapy may extend for a number of weeks or months.

In one embodiment of the invention, the modulator of Kv3.1 and/or Kv3.2 and/or Kv3.3 is used in combination with a further therapeutic agent or agents. When the modulators are used in combination with other therapeutic agents, the compounds may be administered either sequentially or simultaneously by any convenient route. Alternatively, the compounds may be administered separately.

The combinations referred to above may conveniently be presented for use in the form of a pharmaceutical formulation. However, the individual components of such combinations may be administered either sequentially or simultaneously in separate or combined pharmaceutical formulations. The individual components of combinations may also be administered separately, through the same or different routes.

Therapeutic agents which may be used in combination with the present invention include NSAIDS (such as aspirin, naproxen, ibuprofen, parecoxib, diclofenac), paracetamol, pregabalin, gabapentin or opioids (such as fentanyl, sufentanil, oxycodone, morphine, tramadol, codeine).

Therapeutic agents which may be used in combination for neuropathic pain include pregabalin, duloxetine and capsaicin.

Appropriate doses will be readily appreciated by those skilled in the art. The Kv3.1/Kv3.2/Kv3.3 modulator, such as a compound of formula (I) or a pharmaceutically acceptable salt, solvate and/or derivative thereof will suitably be administered at a dosage level which achieves the desired medical outcome without undue adverse effects—namely a safe and effective dose. Example dosages may be in the range of 10 mg to 3 g per day, such as 200 mg to 1.5 g per day.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

EXAMPLES

The invention is illustrated using the compounds described below:

Compound 1

5,5-dimethyl-3-[2-(7-methylspiro[2H-benzofuran-3,1'-cyclopropane]-4-yl)oxypyrimidin-5-yl]imidazolidine-2,4-dione—Example 58 in WO2012/076877

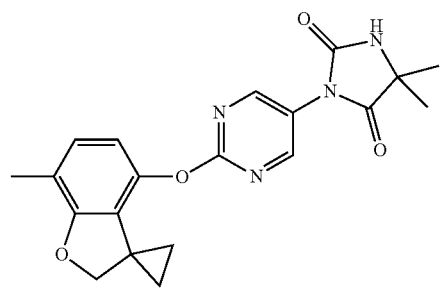

Compound 2

(5R)-5-ethyl-5-methyl-3-[2-({4-methyl-3-[(trifluoromethyl)oxy]phenyl}oxy)-5-pyrimidinyl]-2,4-imidazolidinedione—Example 64 in WO2011/069951

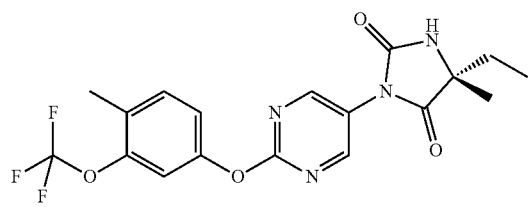 [SMILES: CC[C@@]1(C)NC(=O)N(c2cnc(Oc3ccc(C)c(OC(F)(F)F)c3)nc2)C1=O]

Compound 3

5-methyl-4-{6-[(7-methylspiro[1-benzofuran-3,1'-cyclopropan]-4-yl)oxy]pyridin-3-yl}-2,4-dihydro-3H-1,2,4-triazol-3-one—Example 14 in WO2013/175215

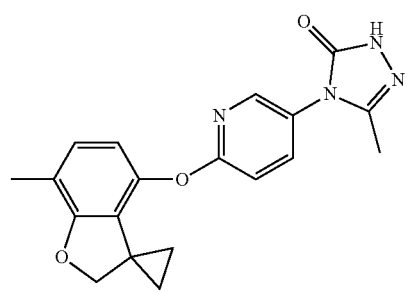 [SMILES: Cc1ccc(Oc2ccc(-n3c(C)n[nH]c3=O)cn2)c2c1OCC21CC1]

Compound 4

(5R)-5-ethyl-3-[6-(7-methylspiro[2H-benzofuran-3,1'-cyclopropane]-4-yl)oxy-3-pyridyl]imidazolidine-2,4-dione—Example 6 in WO2013/083994

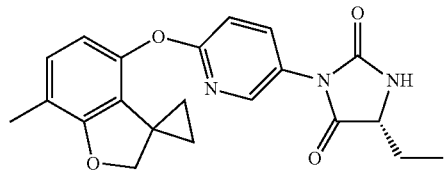 [SMILES: CC[C@H]1NC(=O)N(c2ccc(Oc3ccc(C)c4c3C3(CC3)CO4)nc2)C1=O]

Example 1: Measurement of Kv3 Channel Modulation

The ability of the compounds of the invention to modulate the voltage-gated potassium channel subtypes Kv3.3/Kv3.2/Kv3.1 may be determined using the following assay. Analogous methods may be used to investigate the ability of the compounds of the invention to modulate other channel subtypes.

Cell Biology

To assess compound effects on human Kv3.3 channels (hKv3.3), a stable cell line expressing human Kv3.3 channels was created by transfecting Chinese Hamster Ovary (CHO)-K1 cells with a pBacMire_KCNC-3 vector. Cells were cultured in DMEM/F12 (Gibco) supplemented with 10% Foetal Bovine Serum (Gibco), 1× non-essential amino acids (Invitrogen) and geneticin (G418) 400 microg/mL. Cells were grown and maintained at 37° C. in a humidified environment containing 5% $CO_2$ in air.

To assess compound effects on human Kv3.2 channels (hKv3.2), a stable cell line expressing human Kv3.2 channels (hKv3.2) was created by transfecting CHO-K1 cells with a pCIH5-hKv3.2 vector. Cells were cultured in DMEM/F12 medium supplemented by 10% Foetal Bovine Serum, 1× non-essential amino acids (Invitrogen) and 100 ug/ml of Hygromycin-B (Invitrogen). Cells were grown and maintained at 37° C. in a humidified environment containing 5% $CO_2$ in air.

To assess compound effects on human Kv3.1 channels (hKv3.1), CHO/Gam/E1A-clone22 alias CGE22 cells were transduced using a hKv3.1 BacMam reagent. This cell line was designed to be an improved CHO-K1-based host for enhanced recombinant protein expression as compared to wild type CHO-K1. The cell line was generated following the transduction of CHO-K1 cells with a BacMam virus expressing the Adenovirus-Gam1 protein and selection with Geneticin-G418, to generate a stable cell line, CHO/Gam-A3. CHO/Gam-A3 cells were transfected with pCDNA3-E1A-Hygro, followed by hygromycin-B selection and FACS sorting to obtain single-cell clones. BacMam-Luciferase and BacMam-GFP viruses were then used in transient transduction studies to select the clone based on highest BacMam transduction and recombinant protein expression. CGE22 cells were cultured in the same medium used for the hKv3.2 CHO-K1 stable cell line with the addition of 300 ug/ml hygromycin-B and 300 ug/ml G418. All other conditions were identical to those for hKv3.2 CHO-K1 cells. The day before an experiment 10 million CGE22 cells were plated in a T175 culture flask and the hKv3.1 BacMam reagent (pFBM/human Kv3.1) was added (MOI of 50). Transduced cells were used 24 hours later.

Cell Preparation for IonWorks Quattro™ Experiments

The day of the experiment, cells were removed from the incubator and the culture medium removed. Cells were washed with 5 ml of Dulbecco's PBS (DPBS) calcium and magnesium free and detached by the addition of 3 ml Versene (Invitrogen, Italy) followed by a brief incubation at 37° C. for 5 minutes. The flask was tapped to dislodge cells and 10 ml of DPBS containing calcium and magnesium was added to prepare a cell suspension. The cell suspension was then placed into a 15 ml centrifuge tube and centrifuged for 2 min at 1200 rpm. After centrifugation, the supernatant was removed and the cell pellet re-suspended in 4 ml of DPBS containing calcium and magnesium using a 5 ml pipette to break up the pellet. Cell suspension volume was then corrected to give a cell concentration for the assay of approximately 3 million cells per ml.

All the solutions added to the cells were pre-warmed to 37° C.

Electrophysiology

Experiments were conducted at room temperature using IonWorks Quattro™ planar array electrophysiology technology (Molecular Devices Corp.) with PatchPlate™ PPC. Stimulation protocols and data acquisition were carried out using a microcomputer (Dell Pentium 4). Planar electrode hole resistances (Rp) were determined by applying a 10 mV voltage step across each well. These measurements were performed before cell addition. After cell addition and seal formation, a seal test was performed by applying a voltage step from −80 mV to −70 mV for 160 ms. Following this, amphotericin-B solution was added to the intracellular face of the electrode to achieve intracellular access. Cells were held at −70 mV. Leak subtraction was conducted in all experiments by applying 50 ms hyperpolarizing (10 mV) prepulses to evoke leak currents followed by a 20 ms period at the holding potential before test pulses. For hKv3.2 and hKv3.1 assays, from the holding potential of −70 mV, a first test pulse to −15 mV was applied for 100 ms and following a further 100 ms at −70 mV, a second pulse to 40 mV was applied for 50 ms. Cells were then maintained for a further 100 ms at −100 mV and then a voltage ramp from −100 mV to 40 mV was applied over 200 ms. For hKv3.3 assays, from the holding potential of −70 mV, a first test pulse to 0 mV was applied for 500 ms and following a further 100 ms at −70 mV, a second pulse to 40 mV was applied for 200 ms. These longer test pulses were used to study inactivation of hKv3.3 channels.

Test pulses protocol may be performed in the absence (pre-read) and presence (post-read) of the test compound. Pre- and post-reads may be separated by the compound addition followed by a 3-minute incubation.

Solutions and Drugs

The intracellular solution contained the following (in mM): K-gluconate 100, KCl 54, $MgCl_2$ 3.2, HEPES 5, adjusted to pH 7.3 with KOH. Amphotericin-B solution was prepared as 50 mg/ml stock solution in DMSO and diluted to a final working concentration of 0.1 mg/ml in intracellular solution. The external solution was Dulbecco's Phosphate Buffered Saline (DPBS) and contained the following (in mM): $CaCl_2$ 0.90, KCl 2.67, $KH_2PO_4$ 1.47, $MgCl.6H_2O$ 0.493, NaCl 136.9, $Na_3PO_4$ 8.06, with a pH of 7.4.

Compounds of use in the invention (or reference compounds such as N-cyclohexyl-N-[(7,8-dimethyl-2-oxo-1,2-dihydro-3-quinolinyl)methyl]-N'-phenylurea were dissolved in dimethylsulfoxide (DMSO) at a stock concentration of 10 mM. These solutions were further diluted with DMSO using a Biomek FX (Beckman Coulter) in a 384 compound plate. Each dilution (1 µL) was transferred to another compound plate and external solution containing 0.05% pluronic acid (66 µL) was added. 3.5 µL from each plate containing a compound of the invention was added and incubated with the cells during the IonWorks Quattro™ experiment. The final assay dilution was 200 and the final compound concentrations were in the range 50 µM to 50 nM.

Data Analysis

The recordings were analysed and filtered using both seal resistance (>20 MΩ) and peak current amplitude (>500 pA at the voltage step of 40 mV) in the absence of compound to eliminate unsuitable cells from further analysis. For hKv3.2 and hKv3.1 assays, paired comparisons of evoked currents between pre- and post-drug additions measured for the −15 mV voltage step were used to determine the positive modulation effect of each compound. Kv3 channel-mediated outward currents were measured determined from the mean amplitude of the current over the final 10 ms of the −15 mV voltage pulse minus the mean baseline current at −70 mV over a 10 ms period just prior to the −15 mV step. These Kv3 channel currents following addition of the test compound were then compared with the currents recorded prior to compound addition. Data were normalised to the maximum effect of the reference compound (50 microM of N-cyclohexyl-N-[(7,8-dimethyl-2-oxo-1,2-dihydro-3-quinolinyl)methyl]-N'-phenylurea) and to the effect of a vehicle control (0.5% DMSO). The normalised data were analysed using ActivityBase or Excel software. The concentration of compound required to increase currents by 50% of the maximum increase produced by the reference compound ($EC_{50}$) was determined by fitting of the concentration-response data using a four parameter logistic function in ActivityBase. For hKv3.3 assays, paired comparisons of evoked currents between pre- and post-drug additions were measured for the 0 mV step, considering the peak current and the decay (inactivation) of the current over the duration of the 0 mv test pulse (500 ms).

N-cyclohexyl-N-[(7,8-dimethyl-2-oxo-1,2-dihydro-3-quinolinyl)methyl]-N'-phenylurea was obtained from ASINEX (Registry Number: 552311-06-5).

All of the Example compounds were tested in the above hKv3.1 and hKv3.2 assay measuring potentiation of Kv3.1 or Kv3.2 or Kv3.1 and Kv3.2. Kv3.1 and/or Kv3.2 positive modulators produce in the above assay an increase of whole-cell currents of, on average, at least 20% of the increase observed with 50 micromolar N-cyclohexyl-N-[(7,8-dimethyl-2-oxo-1,2-dihydro-3-quinolinyl)methyl]-N'-phenylurea.

Compound 1 was found to have a pEC50 for Kv3.3 of 5.17. Compound 2 was found to have a pEC50 for Kv3.3 of 4.93. Compound 3 was found to have a pEC50 for Kv3.3 of 4.76.

Compound 2 at 12.5 micromolar produced a mean 113% increase in human Kv3.3 peak current at 0 mV (n=4). Compound 1 at 12.5 micromolar produced a mean 192% increase in human Kv3.3 peak current at 0 mV (n=2).

Compound 4 at 12.5 micromolar produced a mean 365% increase in human Kv3.3 peak current at 0 mV (n=2).

A secondary analysis of the data from the hKv3.1, hKv3.2 and hKv3.3 assays described in Example 1 may be used to investigate the effect of the compounds on rate of rise of the current from the start of the depolarising voltage pulses. The magnitude of the effect of a compound can be determined from the time constant ($Tau_{act}$) obtained from a non-linear fit, using the equation given below, of the rise in Kv3.1, Kv3.2 and Kv3.3 currents following the start of the −15 mV depolarising voltage pulse.

$$Y=(Y0-Y\max)*\exp(-K*X)+Y\max$$

where:
 Y0 is the current value at the start of the depolarising voltage pulse;
 Ymax is the plateau current;
 K is the rate constant, and $Tau_{act}$ is the activation time constant, which is the reciprocal of K.

Similarly, the effect of the compounds on the time taken for Kv3.1, Kv3.2 or Kv3.3 currents to decay on closing of the channels at the end of the −15 mV depolarising voltage pulses can also be investigated. In this latter case, the magnitude of the effect of a compound on channel closing can be determined from the time constant ($Tau_{deact}$) of a non-linear fit of the decay of the current ("tail current") immediately following the end of the depolarising voltage pulse.

Kv3.1, Kv3.2 and Kv3.3 channels must activate and deactivate very rapidly in order to allow neurons to fire actions potentials at high frequency (Rudy et al., 2001). Slowing of activation is likely to delay the onset of action potential repolarisation; slowing of deactivation could lead to hyperpolarising currents that reduce the excitability of the neuron and delay the time before the neuron can fire a further action potential. Together these two slowing effects on channel activation and deactivation are likely to lead to a reduction rather than a facilitation of the neurons ability to fire at high frequencies. Thus compounds that have this slowing effect on the Kv3.1 and/or Kv3.2, and/or Kv3.3 channels will effectively behave as negative modulators of the channels, leading to a slowing of neuronal firing. This latter effect has been shown for certain of the compounds disclosed in WO2011/069951, where marked increases in $Tau_{act}$ can be observed from recordings made from "fast-firing" interneurons in the cortex of rat brain, using electrophysiological techniques, in vitro. The addition of the relevant compounds reduces the ability of the neurons to fire in response to trains of depolarising pulses at 300 Hz.

Therefore, although certain compounds may be identified act as positive modulators in the recombinant cell assay of Example 1, those compounds which markedly increase the value of $Tau_{act}$ can reduce the ability of neurons in native tissues to fire at high frequency.

Example 2: Evaluation of the Effect of Modulators of Kv3.1/Kv3.2 Channels on Sensitivity to Mechanical and Cold Stimuli in Models of Neuropathic and Inflammatory Pain in the Rat The efficacy of Compounds 1, 2, 3 and 4 was investigated using rat models of neuropathic and/or persistant inflammatory pain.

Materials and Methods

Subjects comprised male, Wistar Hanover rats, 6 animals per group (225±2 g for Compound 1 studies and Compound 2 studies; 214±1 g for Compound 3 studies; 236±1 g for Compound 4 studies).

Vehicle (12% Captisol®; 0.5% w/v HPMC and 0.1% w/v Tween-80; 5 ml/kg via the intraperitoneal route) was prepared using autoclaved deionized water not more than one week prior to use.

The details of the studies performed are outlined in Table 1.

TABLE 1

Dosing regimen for neuropathic and inflammatory pain models.

| Compound | Neuropathic Pain | | Inflammatory Pain |
| --- | --- | --- | --- |
| | Study 1 | Study 2 | |
| Compound 1 | 30 mg/kg (i.p.)[1]<br>60 mg/kg (i.p.) | 10 mg/kg (i.p.)<br>30 mg/kg (i.p.)<br>60 mg/kg (i.p.) | 10 mg/kg (i.p.)<br>30 mg/kg (i.p.)<br>60 mg/kg (i.p.) |
| Compound 2 | 30 mg/kg (i.p.)<br>60 mg/kg (i.p.) | 10 mg/kg (i.p.)<br>30 mg/kg (i.p.)<br>60 mg/kg (i.p.) | 10 mg/kg (i.p.)<br>30 mg/kg (i.p.)<br>60 mg/kg (i.p.) |
| Compound 3 | 30 mg/kg (i.p.)<br>60 mg/kg (i.p.) | N/A | 10 mg/kg (i.p.)<br>30 mg/kg (i.p.)<br>60 mg/kg (i.p.) |
| Compound 4 | N/A | N/A | 3 mg/kg (i.p.)<br>10 mg/kg (i.p.)<br>30 mg/kg (i.p.) |

[1](i.p.) intraperitoneal administration

The control for the neuropathic pain model was lamotrigine, administered at 30 mg/kg via oral delivery. The control for the inflammatory pain model was diclofenac, administered at 30 mg/kg via oral delivery. Statistical analysis was performed using one-way ANOVA, and comparisons were performed with time-matched vehicle group using Tukey's HSD test wherein * $p<0.05$,  $p<0.01$, * $p<0.001$.

Experimental Protocol

All experimental procedures were approved following review by an institutional ethics committee on the use of animals is research, and were carried out in accordance with the UK Home Office Animal Procedures Act (1986).

Treatment groups were randomised and blinded. Groups of 6 rats were used.

Neuropathic Pain

Neuropathic pain was induced by partial ligation of the sciatic nerve. Briefly, the rats were anaesthetised (isoflurane/ $O_2$ inhalation), the left sciatic nerve exposed at mid-thigh level through a small incision and ⅓ to ½ of the nerve thickness tightly ligated within a 7.0 silk suture. The wound was closed with surgical glue. Animals were allowed to recover and tested 12-15 days following surgery.

Withdrawal thresholds or latencies were measured on both the ipsilateral (ligated) and contralateral (non-ligated) paws, prior to (predose) and then up to 24 h following drug or vehicle administration.

Pre-dose behavioural measurements were obtained by measuring paw withdrawals 14 days following nerve ligation; before the initiation of drug treatment. Following treatment, further readings were taken at 1, 3, 6 and 24 hour after administration.

Inflammatory Pain

Mechanical hyperalgesia was examined in a model of persistent inflammatory pain. The hyperalgesia was induced by an intraplantar injection (25 µl) of Freund's Complete Adjuvant (FCA) into the left hind paw.

To assess the effect of the test compound, paw withdrawal thresholds or latencies were measured on both the ipsilateral (FCA-injected) and contralateral (non-injected) paws, prior to (naïve) and 24 hours following FCA injection (predose), and then at 1, 3, 6 and 24 hours after drug or vehicle administration.

Behavioural Tests

Mechanical hyperalgesia was examined in a model of neuropathic pain by measuring paw withdrawal thresholds (PWT) to increasing mechanical force applied to the dorsal surface of the rat paw using an Analgesymeter (Ugo-Basile, Milan) equipped with a wedge-shaped probe (area 1.75 $mm^2$). Cut-off was set at 250 g and the end-point was taken as withdrawal of the hind paw. Both ipsilateral and contralateral paw withdrawal readings were taken.

Cold sensitivity was assessed using a commercially available cold-plate (Ugo Basile, Milan). The cold plate was allowed to stabilize for 5 minutes at the set temperature prior to testing. Paw withdrawal latencies (PWL) were determined with the cold-plate set at 10° C. The animals were lightly restrained and each hind paw in turn placed onto the surface of the cold-plate. The end point was taken as the withdrawal of the paw and recorded as the withdrawal latency for the ipsilateral and the contralateral paw. A maximum cut-off of 30 seconds was used for each paw.

General Observations

In addition to behavioural pain readings, each rat was observed throughout the study for changes in general behaviour.

Data Analysis

Neuropathic Pain

Data were expressed as withdrawal threshold (g) or withdrawal latencies (s) and percentage reversals calculated according to the following formula:

$$\% \text{ reversal} = \frac{\text{ipsilaterd threshold postdose} - \text{ipsilaterd threshold predose}}{\text{contralateral threshold predose} - \text{ipsilaterd threshold predose}} \times 100$$

Inflammatory Pain

Data were expressed as withdrawal threshold (g) or withdrawal latencies (s) and percentage reversals calculated according to the following formula:

$$\% \text{ reversal} = \left(\frac{\text{left postdose } PWT/L - \text{left predose } PWT/L}{\text{left naïve } PWT/L - \text{left predose } PWT/L}\right) \times 100$$

Statistical analysis was carried out on withdrawal threshold readings using ANOVA with repeated measures followed by Tukey's HSD test. The level for statistical significance was set as $p<0.05$.

Results

Compound 1

Neuropathic Pain Study 1

Partial ligation of the sciatic nerve resulted in a marked decrease in withdrawal threshold to a mechanical stimulus and in withdrawal latency to a cold stimulus of the affected paw.

Figure 1B:
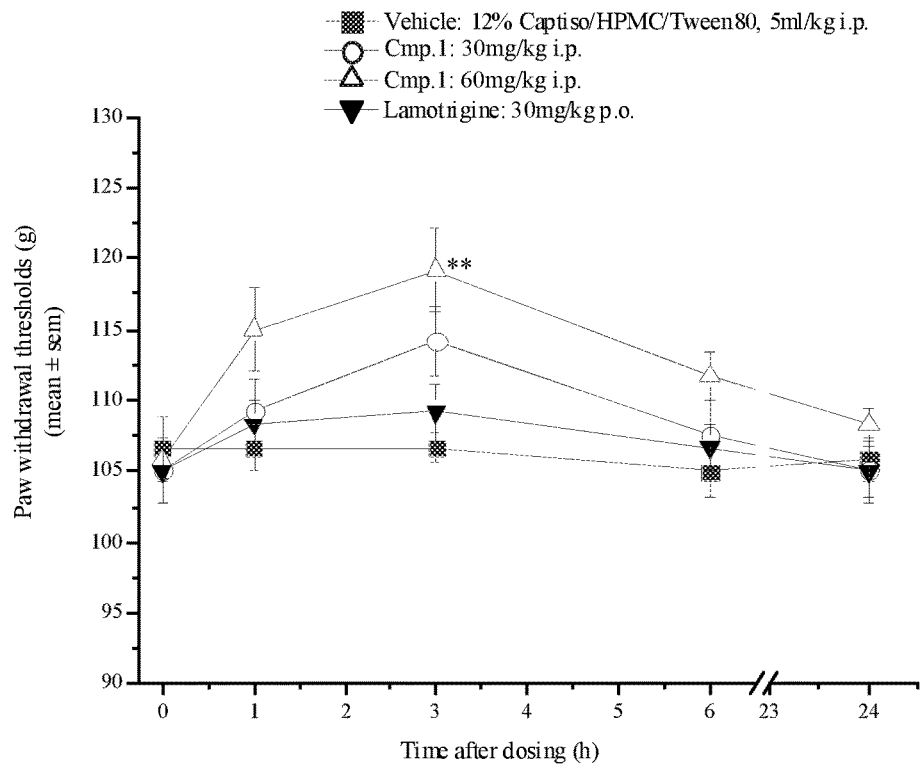
Figure 2A:
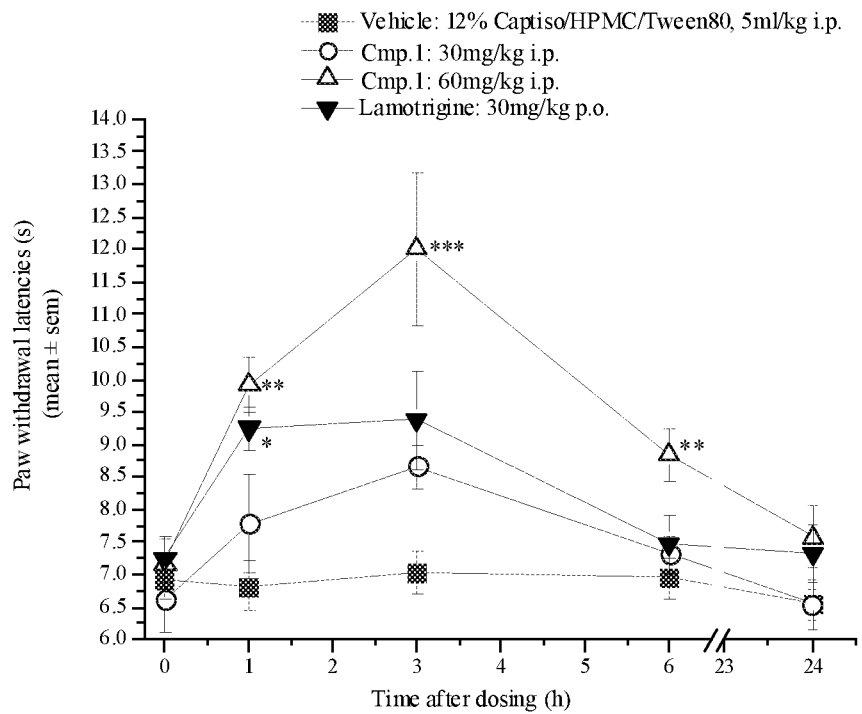
FIG. 2 shows the effect of Compound 1 on paw withdrawal thresholds to a cold stimulus (10° C.) in a neuropathic pain model (Study 1): ipsilateral paw (FIG. 2a); contralateral paw (FIG. 2b); and percentage reversals (FIG. 2c).
Figure 2B:
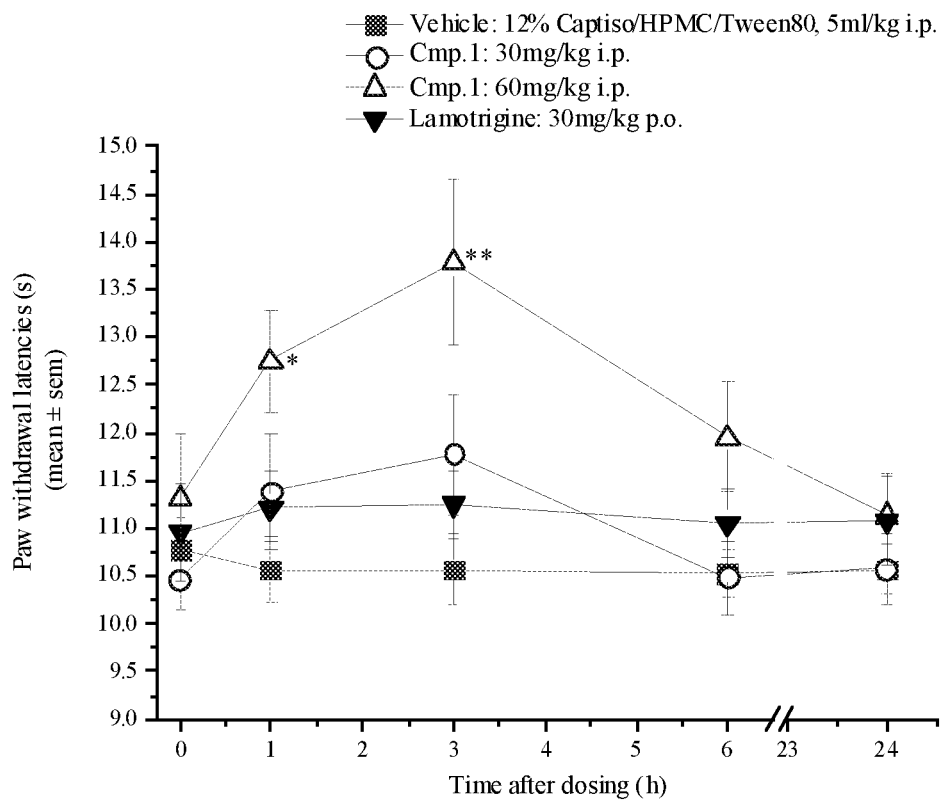

Fourteen days after nerve ligation, predose threshold readings of 66±1 g were measured in the ipsilateral paws compared to 106±1 g in the contralateral paws (FIG. 1a, FIG. 1b). Cold latencies of 7.0±0.2 s were measured in the ipsilateral paws compared to 10.9±0.2 s in the contralateral paws (FIG. 2a, FIG. 2b).

Figure 1C:
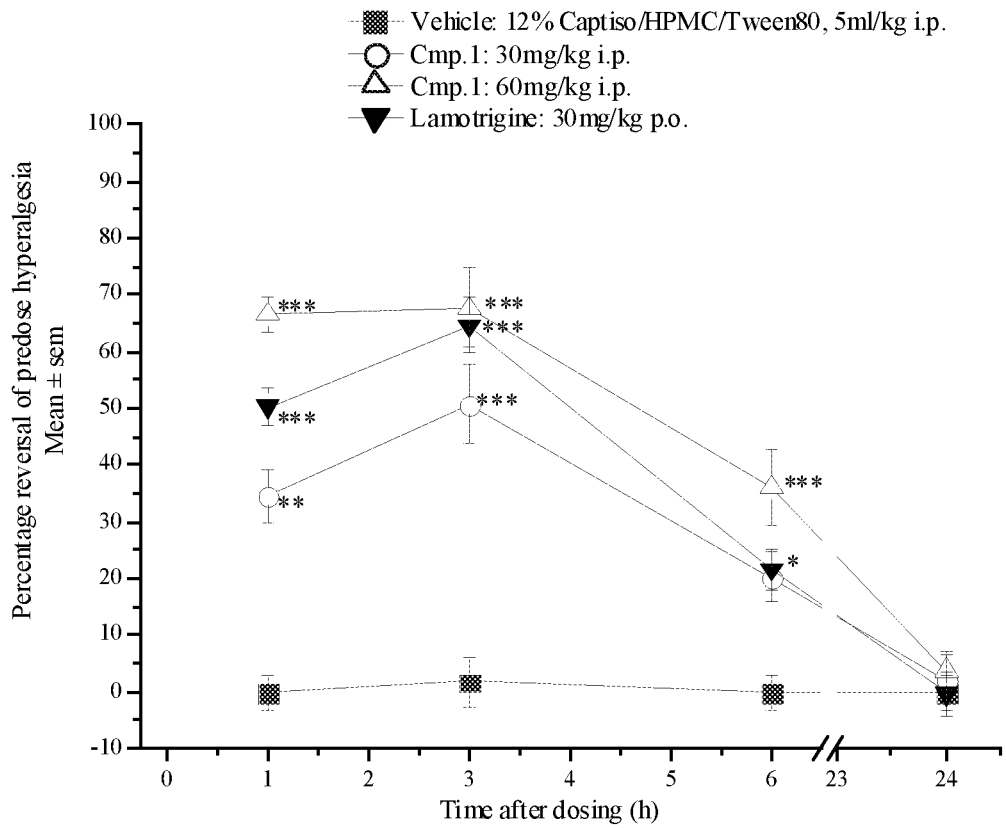
Figure 2C:
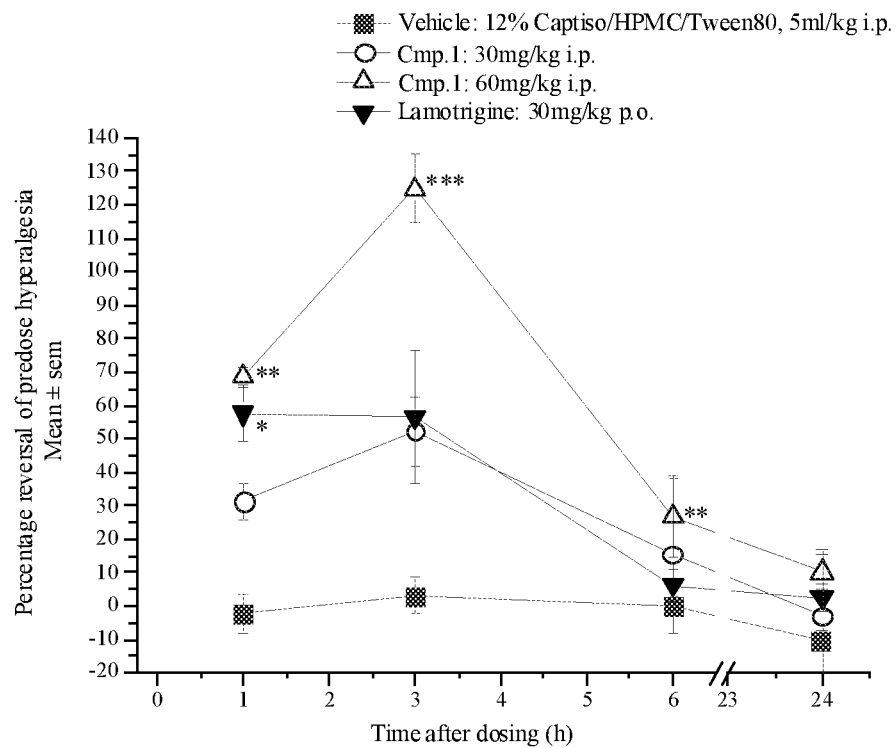

Compound 1 produced a reversal of both mechanical (FIG. 1a, FIG. 1c) and cold sensitivity (FIG. 2a, FIG. 2c) with rapid onset of action and good dose separation.

Peak reversal of mechanical sensitivity was seen at 3 hours post-dose (51% at 30 mg/kg and 68% by 60 mg/kg). Cold sensitivity was reversed at 3 hours post-dose by 52% and 125% by 30 mg/kg and 60 mg/kg respectively. The lower dose of the compound was only statistically active against mechanical hyperalgesia. At 60 mg/kg the compound was still efficacious at 6 hours post-dose. The positive control, lamotrigine, gave peak reversals of 65% (at 3 hours post-dose) and 58% (at 1 hour post-dose) in mechanical and cold respectively.

There were significant changes in contralateral paw withdrawals and latencies with Compound 1 at 60 mg/kg and rats treated with Compound 1 were slightly flaccid at the 1 and 3 hour post-dose time points (both doses).

Neuropathic Pain Study 2

Partial ligation of the sciatic nerve resulted in a marked decrease in withdrawal threshold to a mechanical stimulus and in withdrawal latency to a cold stimulus of the affected paw.

Figure 3A:
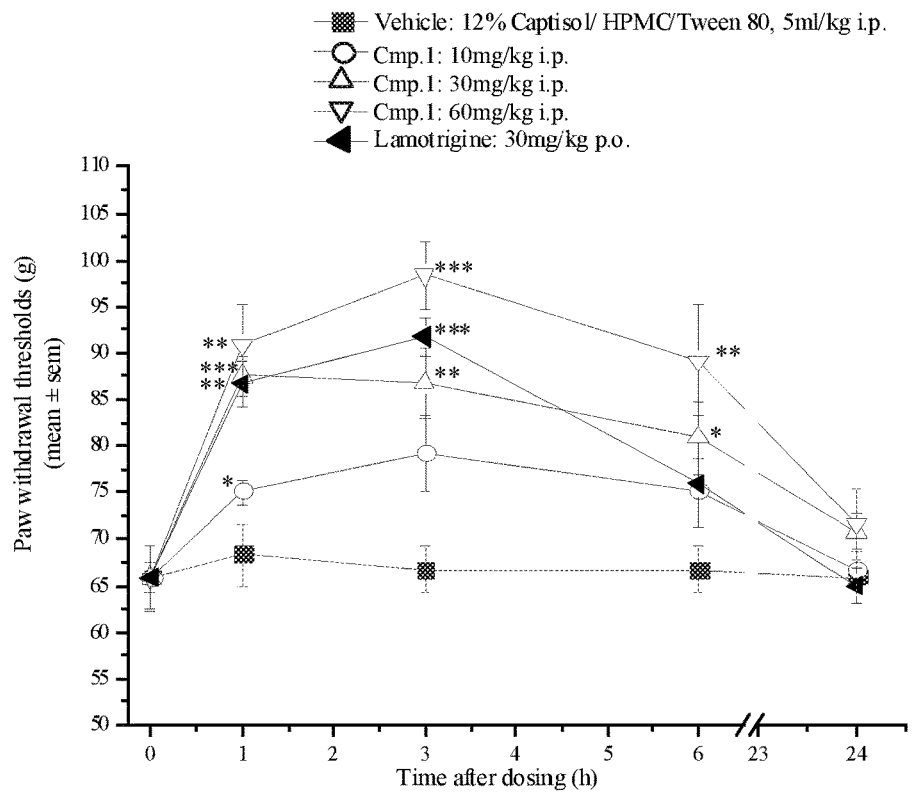
FIG. 3 shows the effect of Compound 1 on paw withdrawal thresholds under mechanical pressure in a neuropathic pain model (Study 2): ipsilateral paw (FIG. 3a); contralateral paw (FIG. 3b); and percentage reversals (FIG. 3c).
Figure 3B:
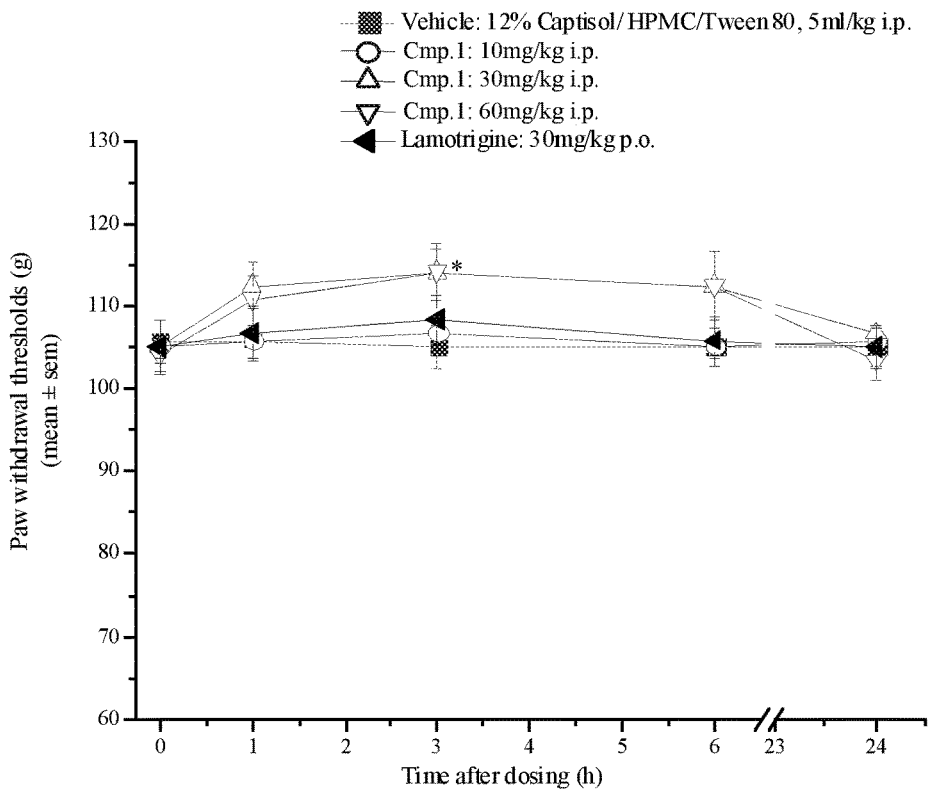
Figure 4A:
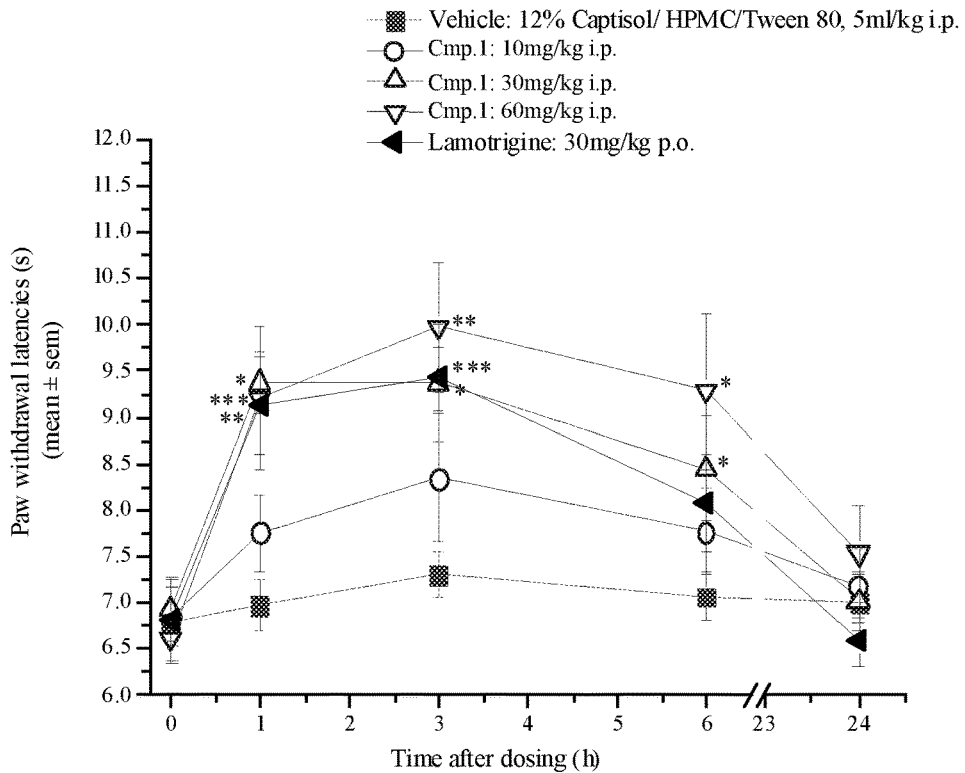
FIG. 4 shows the effect of Compound 1 on paw withdrawal thresholds to a cold stimulus (10° C.) in a neuropathic pain model (Study 2): ipsilateral paw (FIG. 4a); contralateral paw (FIG. 4b); and percentage reversals (FIG. 4c).
Figure 4B:
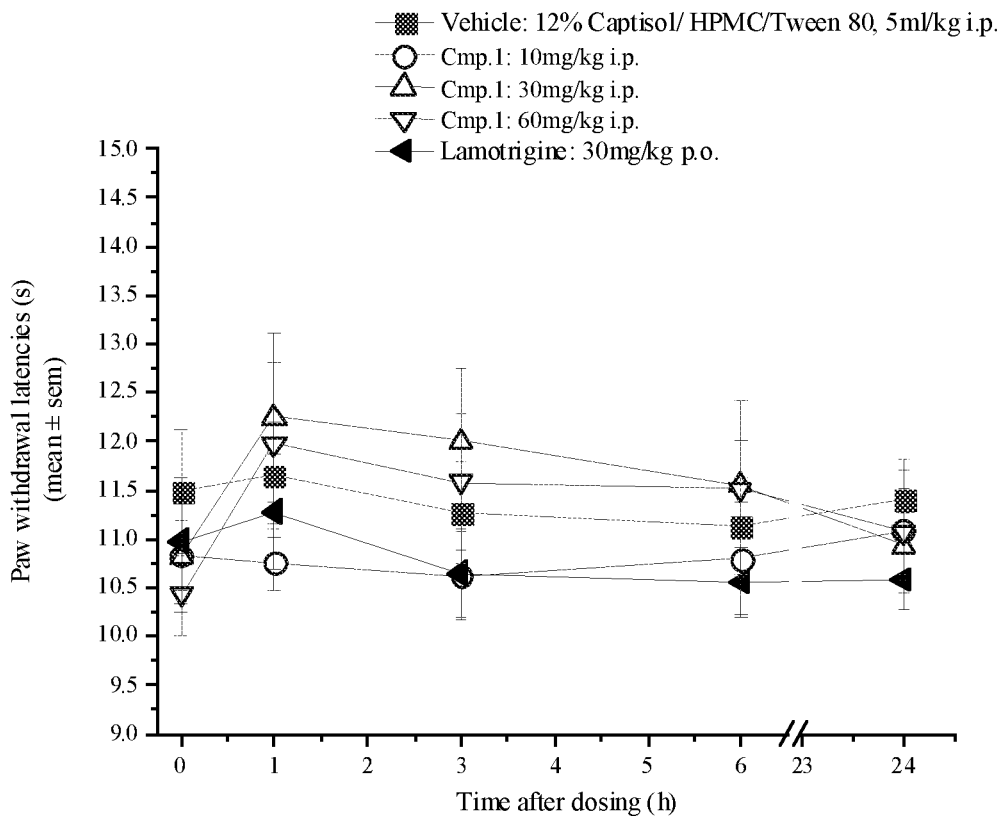

Fourteen days after nerve ligation, predose threshold readings of 66±1 g were measured in the ipsilateral paws compared to 104±1 g in the contralateral paws (FIG. 3a, FIG. 3b). Cold latencies of 6.8±0.1 s were measured in the ipsilateral paws compared to 10.8±0.2 s in the contralateral paws (FIG. 4a, FIG. 4b).

Figure 3C:
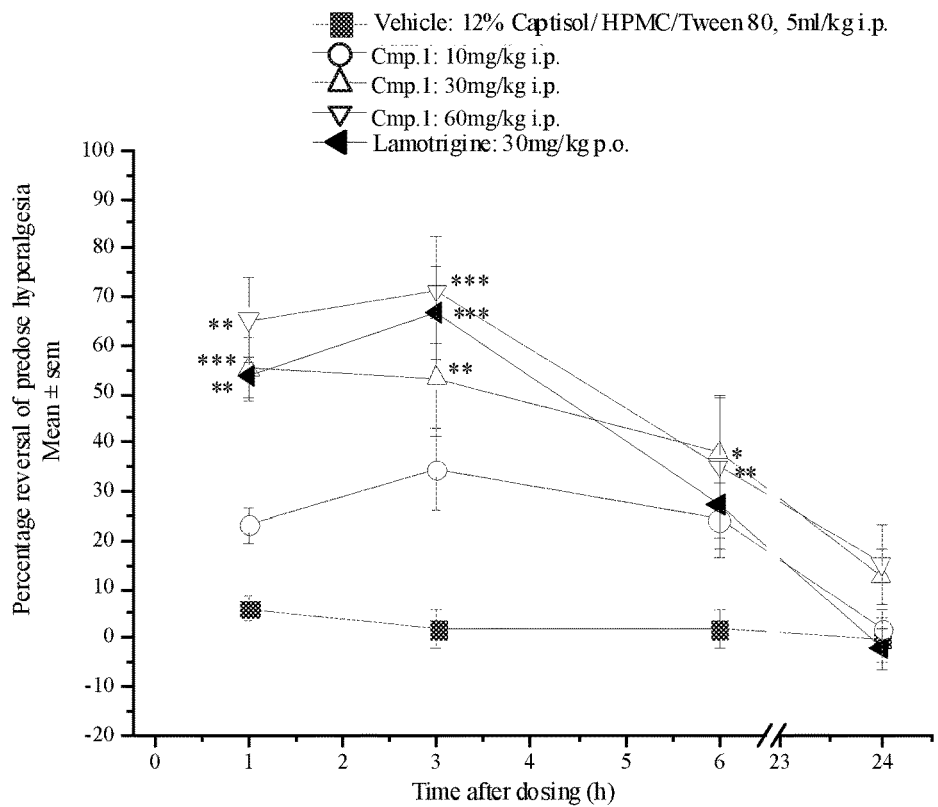
Figure 4C:
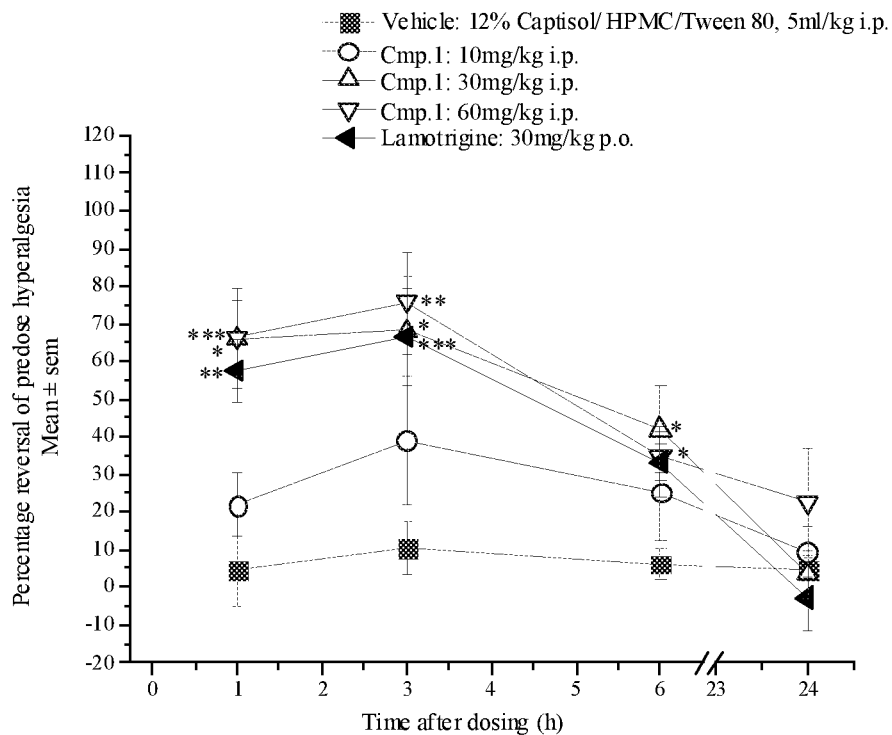

Compound 1 produced a dose-related reversal of mechanical (FIG. 3a, FIG. 3c) and cold sensitivity (FIG. 4a, FIG. 4c) with rapid onset and long duration of action.

Peak reversal of mechanical sensitivity was seen at 3 hours post-dose (31% at 10 mg/kg, 73% at 30 mg/kg and 81% by 60 mg/kg). Cold sensitivity was reversed at 3 hours post-dose by 39%, 68% and 76% by 10, 30 and 60 mg/kg respectively. The positive control, lamotrigine, gave peak reversals at 3 hours post-dose of 67% and 67% in mechanical and cold respectively.

There were small changes in contralateral paw withdrawals and latencies with Compound 1 which just attained significance at 3 hours on mechanical thresholds and there was some mild flaccidity observed in some of the Compound 1 treated rats (⅙ at 30 mg/kg and ⅔ at 60 mg/kg).

Inflammatory Pain Study

Figure 5A:
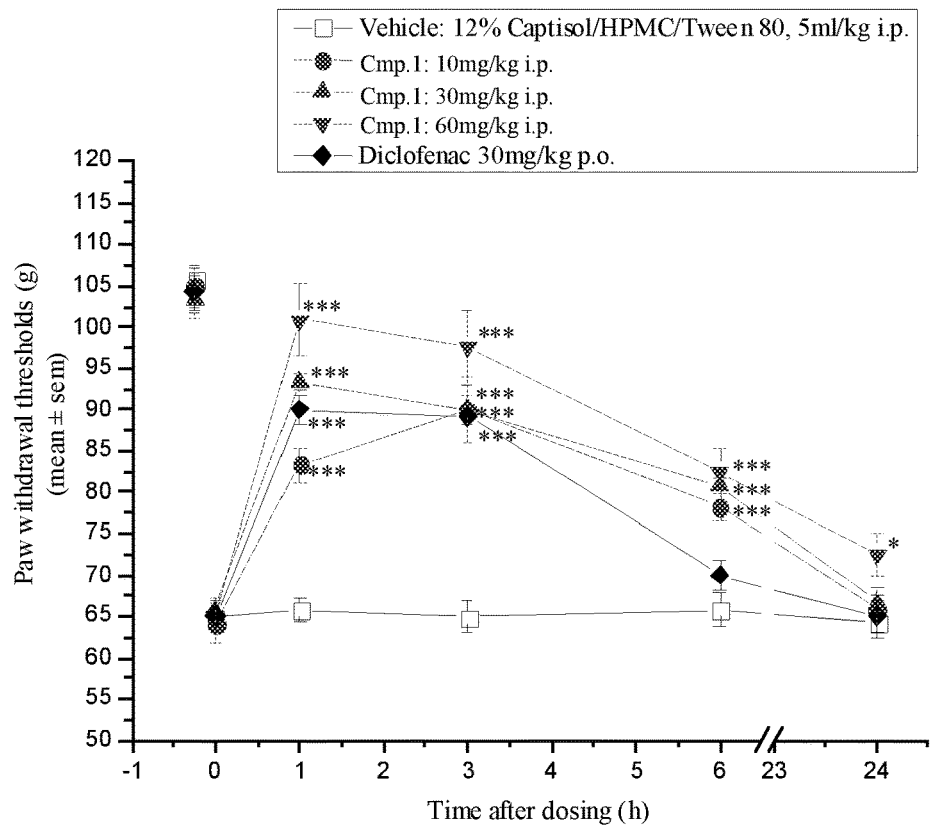
FIG. 5 shows the effect of Compound 1 on paw withdrawal thresholds under mechanical pressure in an inflammatory pain model: ipsilateral paw (FIG. 5a); contralateral paw (FIG. 5b); and percentage reversals (FIG. 5c).
Figure 5B:
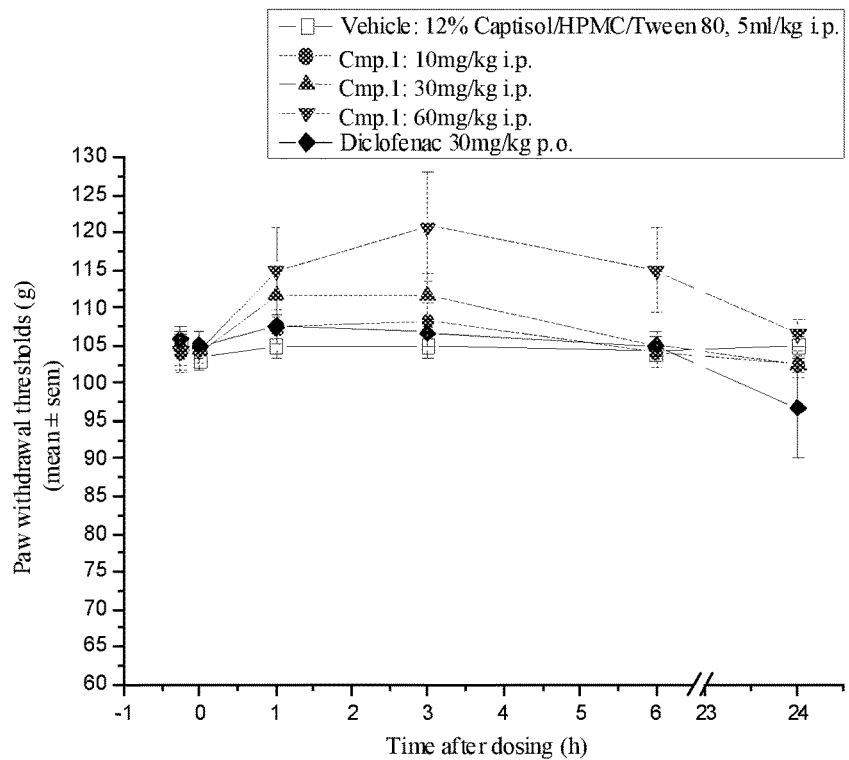
Figure 6A:
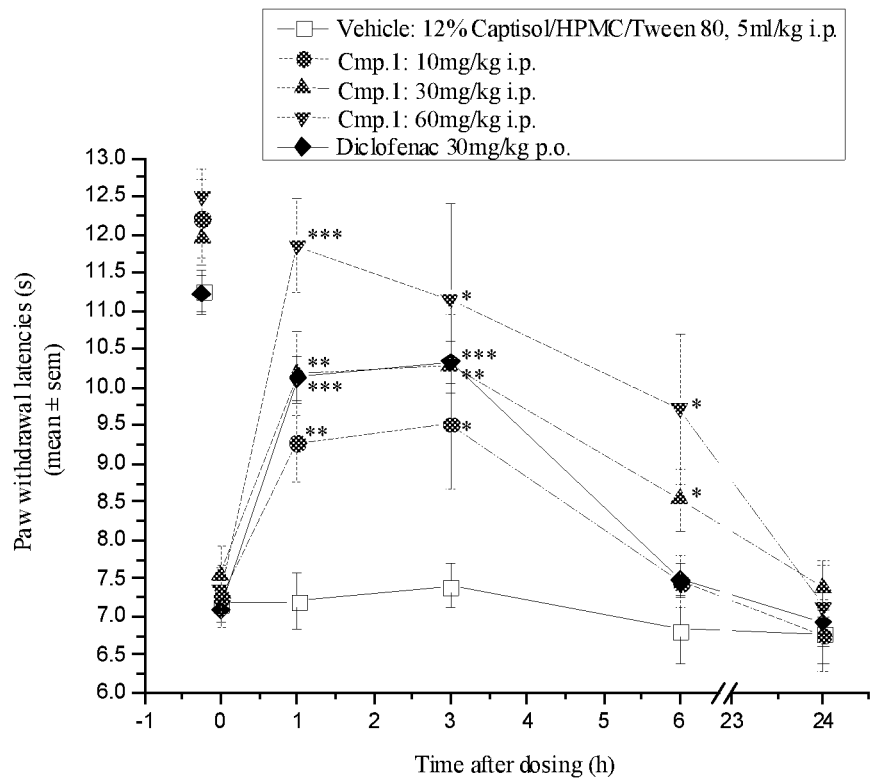
FIG. 6 shows the effect of Compound 1 on paw withdrawal thresholds to a cold stimulus (10° C.) in an inflammatory pain model: ipsilateral paw (FIG. 6a); contralateral paw (FIG. 6b); and percentage reversals (FIG. 6c).
Figure 6B:
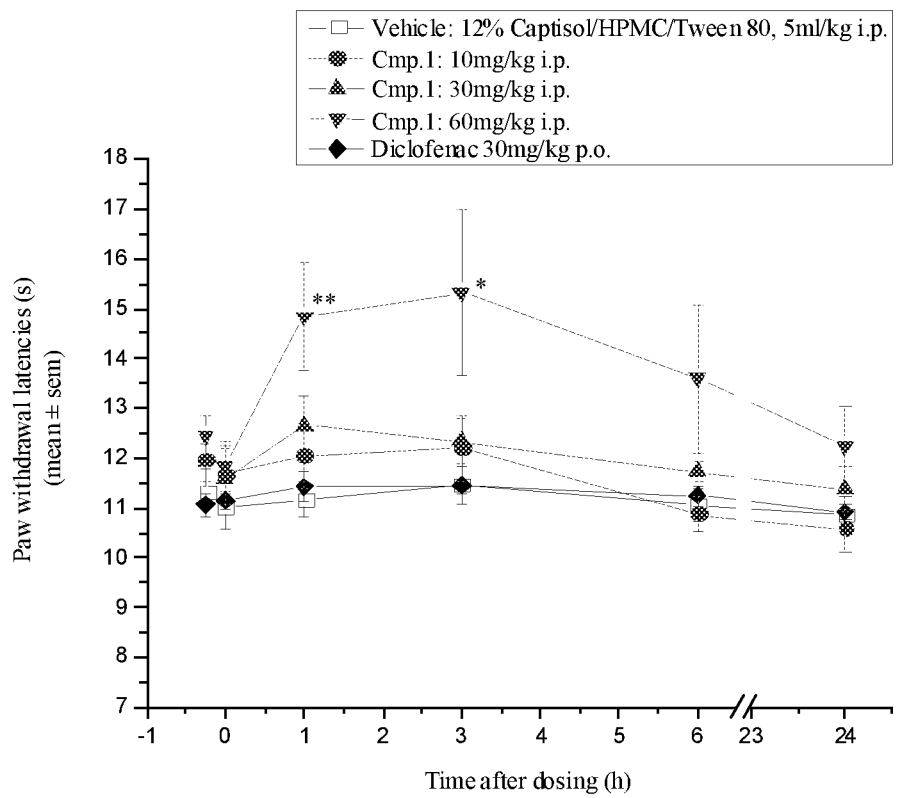
Figure 6C:
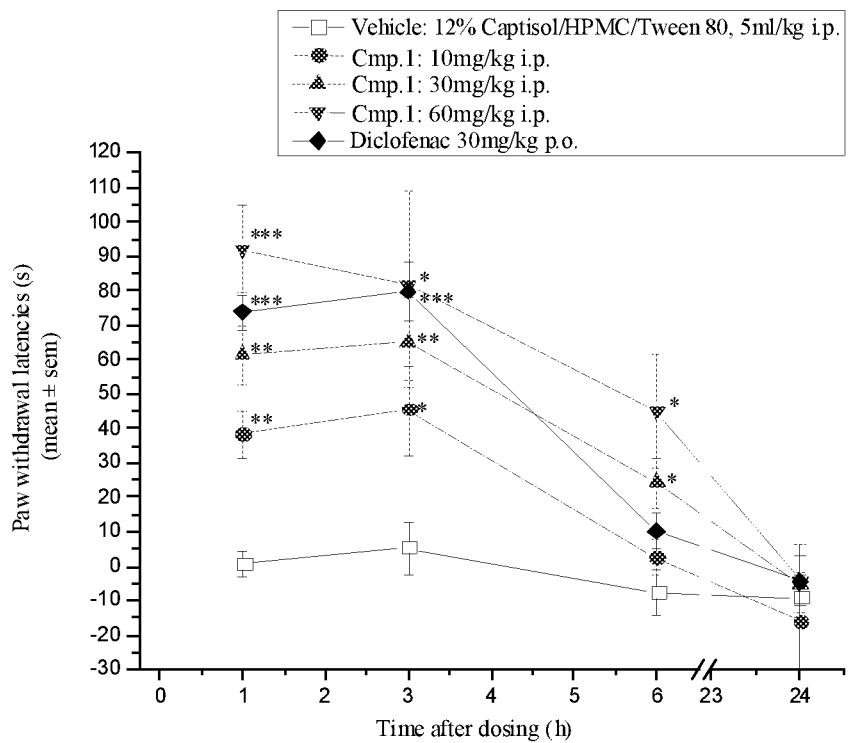

The intraplantar injection of FCA resulted in a marked decrease in withdrawal threshold to a mechanical stimulus and in withdrawal latency to a cold stimulus of the affected paw. The mean naïve threshold readings were 105±1 g. Twenty-four hours after FCA injection, predose threshold readings of 65±1.0 g were measured in the ipsilateral paws compared to 104±1.0 g in the contralateral paws (FIG. 5a, FIG. 5b). The mean naïve cold latency readings were 11.8±0.2 s. Twenty-four hours after FCA injection, predose threshold readings of 7.3±0.1 s were measured in the ipsilateral paws compared to 11.5±0.2 s in the contralateral paws (FIG. 6a, FIG. 6b).

Figure 5C:
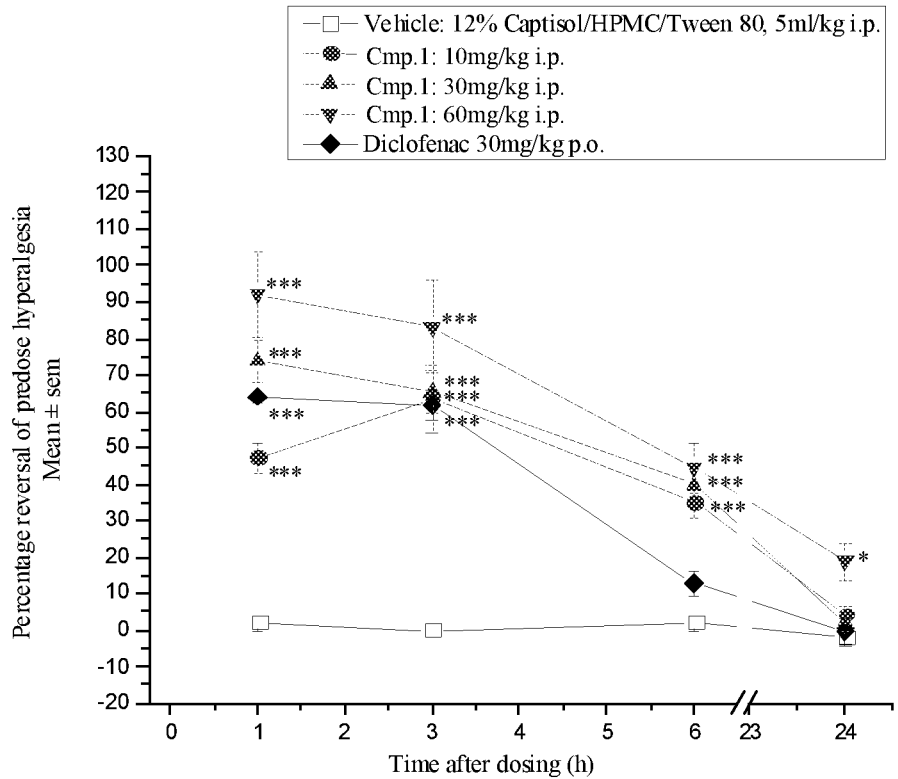

Compound 1 produced a dose-related reversal of both mechanical (FIG. 5a, FIG. 5c) and cold sensitivity (FIG. 6a, FIG. 6b) with rapid onset of action and peak reversal at 1-3 h post-dose. Peak reversal of mechanical sensitivity was seen at 1 hour post-dose for 30 mg/kg and 60 mg/kg (74% and 92% respectively) and at 3 hours post-dose for 10 mg/kg (64% reversal). Peak reversal of cold sensitivity was seen at 3 hours post-dose for 10 mg/kg and 30 mg/kg (45% and 65% respectively) and at 1 hour post-dose for 60 mg/kg (92% reversal). The reversal was long lasting with significant activity still evident at 6 h post-dose: mechanical sensitivity and cold sensitivity were both reversed by 45% with 60 mg/kg. The positive control, diclofenac, gave peak reversals of 64% and 79% in mechanical (1 hour post-dose) and cold (3 hours post-dose) respectively.

Pronounced increases in the contralateral paw withdrawals/latencies were seen with Compound 1 at 60 mg/kg. However, these changes were variable, as shown by the error bars, with only ⅗ animals showing the effect. There was also a noticeable flaccidity seen with ⅔ rats at 30 mg/kg and ⅘ rats at 60 mg/kg (1-6 h post-dose).

Compound 2

Neuropathic Pain Study 1

Partial ligation of the sciatic nerve resulted in a marked decrease in withdrawal threshold to a mechanical stimulus and in withdrawal latency to a cold stimulus of the affected paw.

Figure 7A:
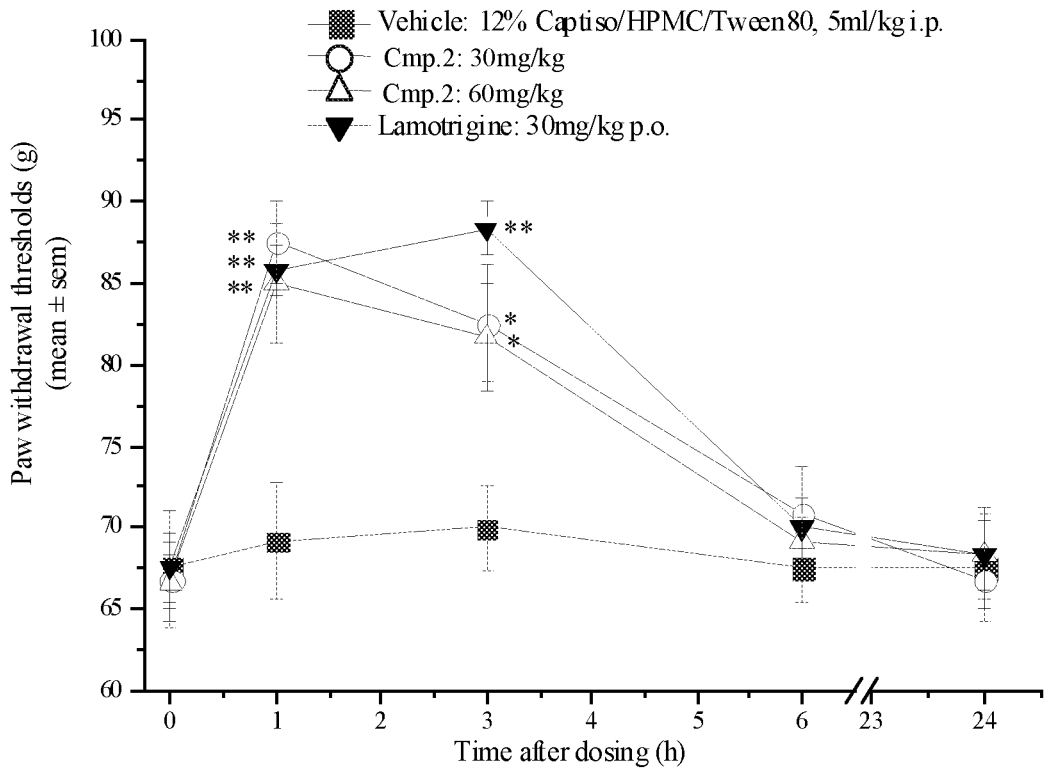
FIG. 7 shows the effect of Compound 2 on paw withdrawal thresholds under mechanical pressure in a neuropathic pain model (Study 1): ipsilateral paw (FIG. 7a); contralateral paw (FIG. 7b); and percentage reversals (FIG. 7c).
Figure 7B:
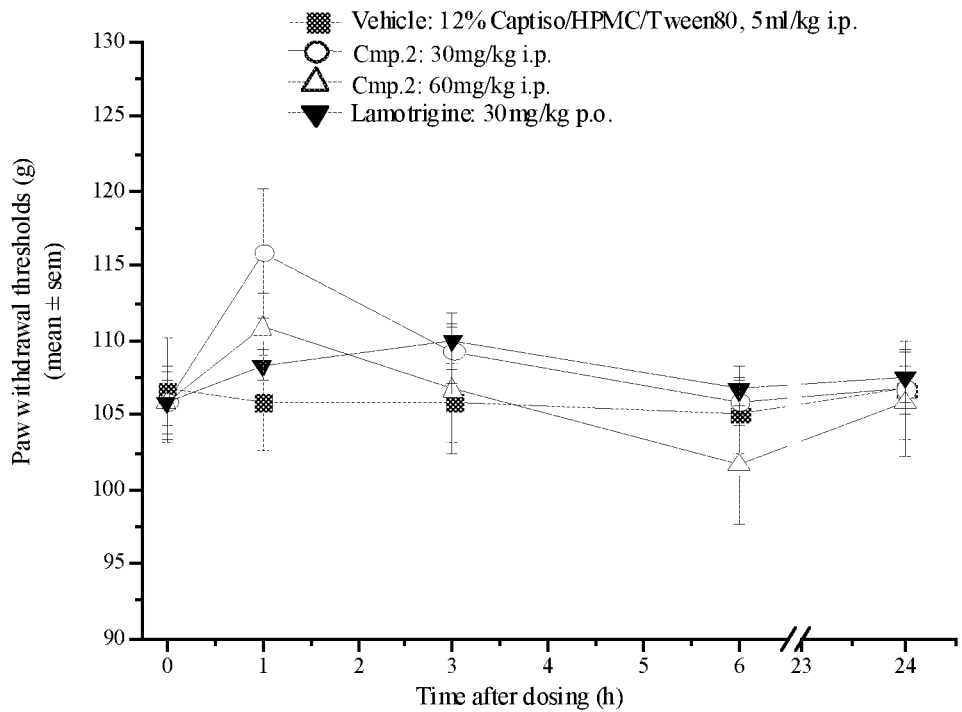
Figure 8A:
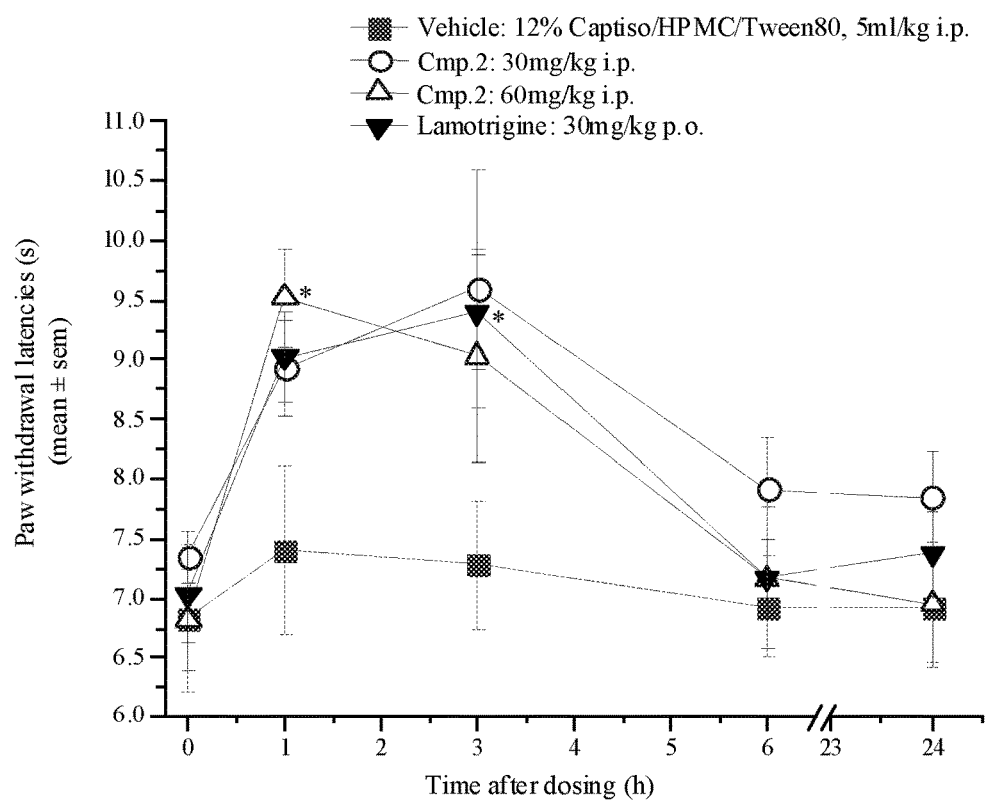
FIG. 8 shows the effect of Compound 2 on paw withdrawal thresholds to a cold stimulus (10° C.) in a neuropathic pain model (Study 1): ipsilateral paw (FIG. 8a); contralateral paw (FIG. 8b); and percentage reversals (FIG. 8c).
Figure 8B:
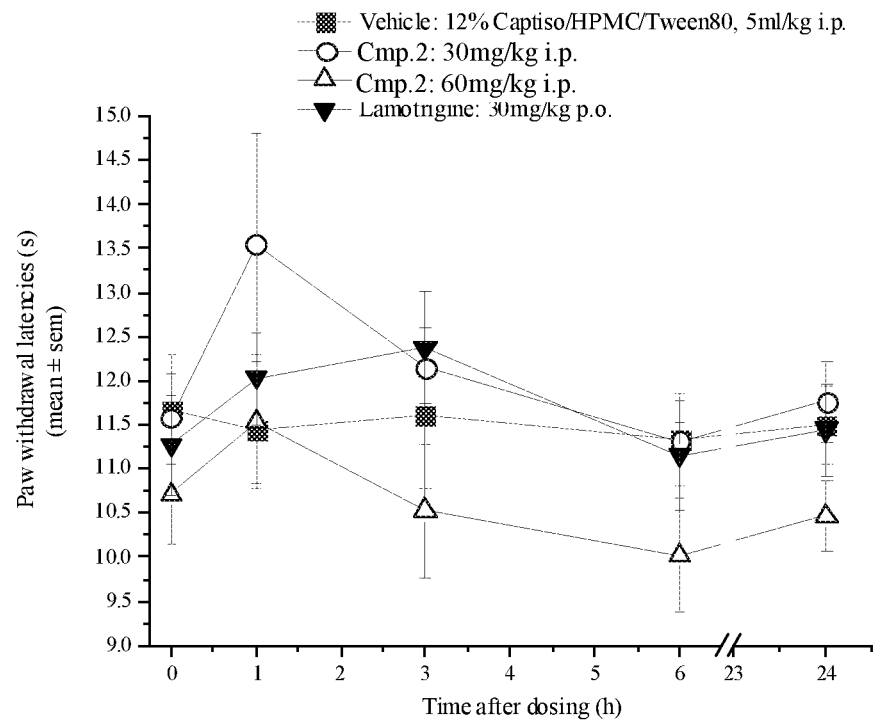

Fourteen days after nerve ligation, predose threshold readings of 67±1 g were measured in the ipsilateral paws compared to 106±1 g in the contralateral paws (FIG. 7a, FIG. 7b). Cold latencies of 7.0±0.2 s were measured in the ipsilateral paws compared to 11.3±0.3 s in the contralateral paws (FIG. 8a, FIG. 8b).

Figure 7C:
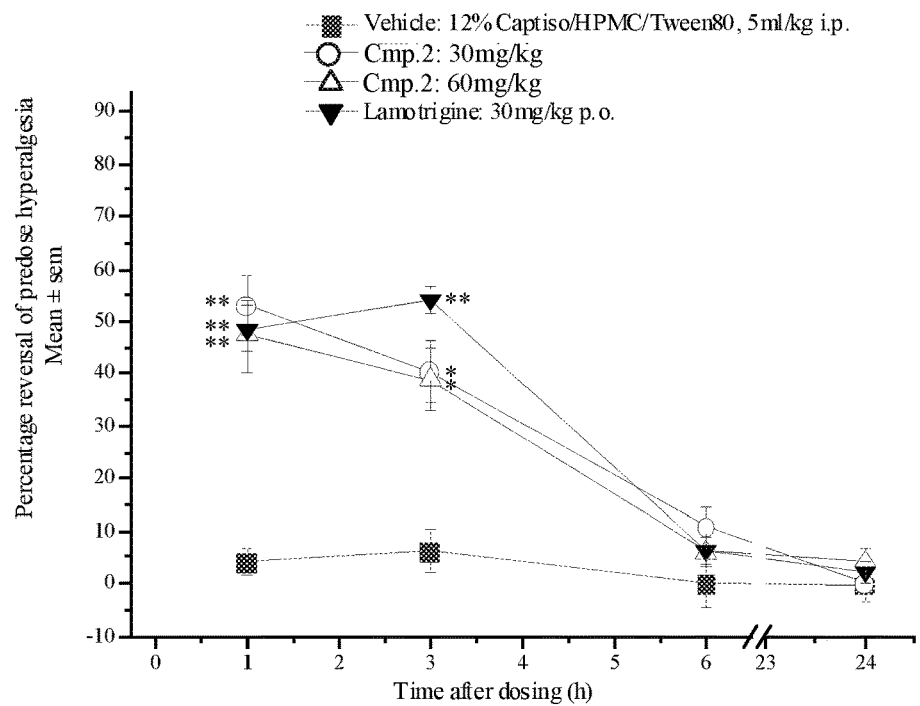
Figure 8C:
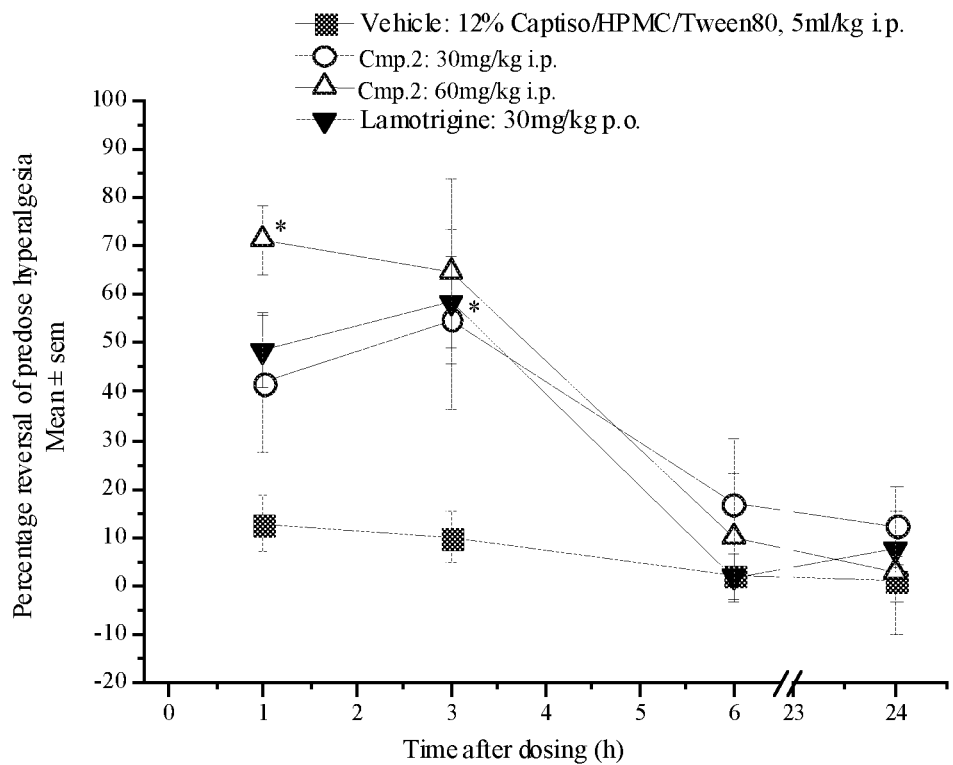

Compound 2 produced a reversal of both mechanical (FIG. 7a, FIG. 7c) and cold sensitivity (FIG. 8a, FIG. 8c) with rapid onset of action and efficacy similar to lamotrigine.

There was little difference in efficacy between the 2 doses of the compound. Peak reversal of mechanical sensitivity was seen at 1 hour post-dose (53% at 30 mg/kg and 47% by 60 mg/kg). Cold sensitivity was reversed at 1 hour post-dose by 42% and 71% by 30 mg/kg and 60 mg/kg respectively, although peak reversal was observed at 3 hours post-dose for 30 mg/kg (55% reversal). Both doses of the compound were efficacious at 3 hours by not by 6 hours post-dose. The positive control, lamotrigine, gave peak reversals at 3 hours post-dose of 54% and 58% in mechanical and cold respectively.

There were no apparent behavioural changes in the rats.

Neuropathic Pain Study 2

Partial ligation of the sciatic nerve resulted in a marked decrease in withdrawal threshold to a mechanical stimulus and in withdrawal latency to a cold stimulus of the affected paw.

Figure 9A:
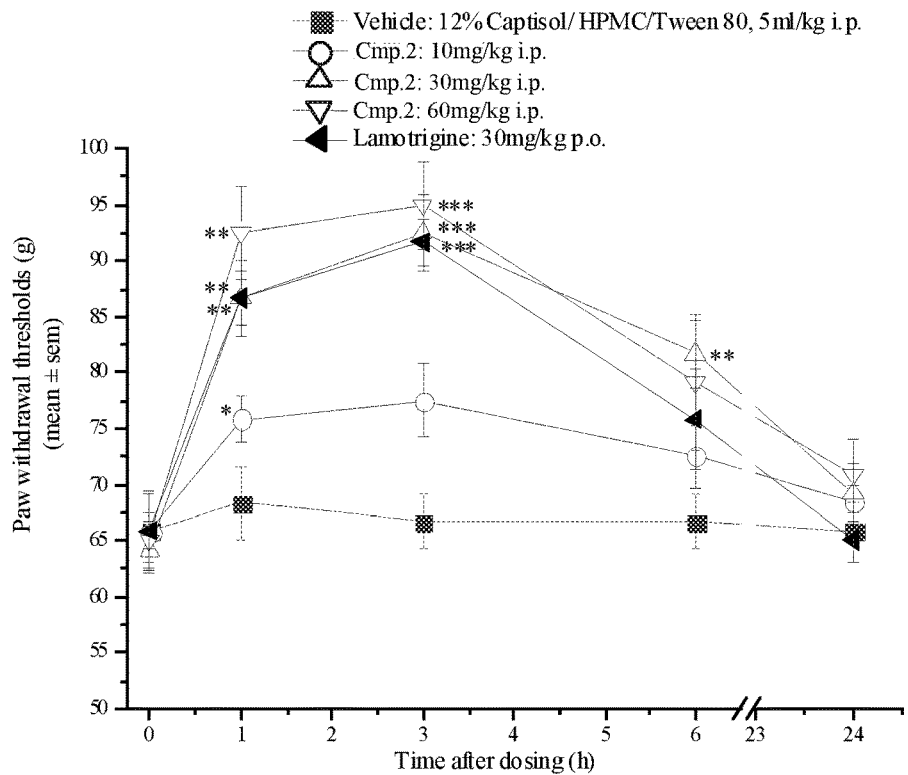
FIG. 9 shows the effect of Compound 2 on paw withdrawal thresholds under mechanical pressure in a neuropathic pain model (Study 2): ipsilateral paw (FIG. 9a); contralateral paw (FIG. 9b); and percentage reversals (FIG. 9c).
Figure 9B:
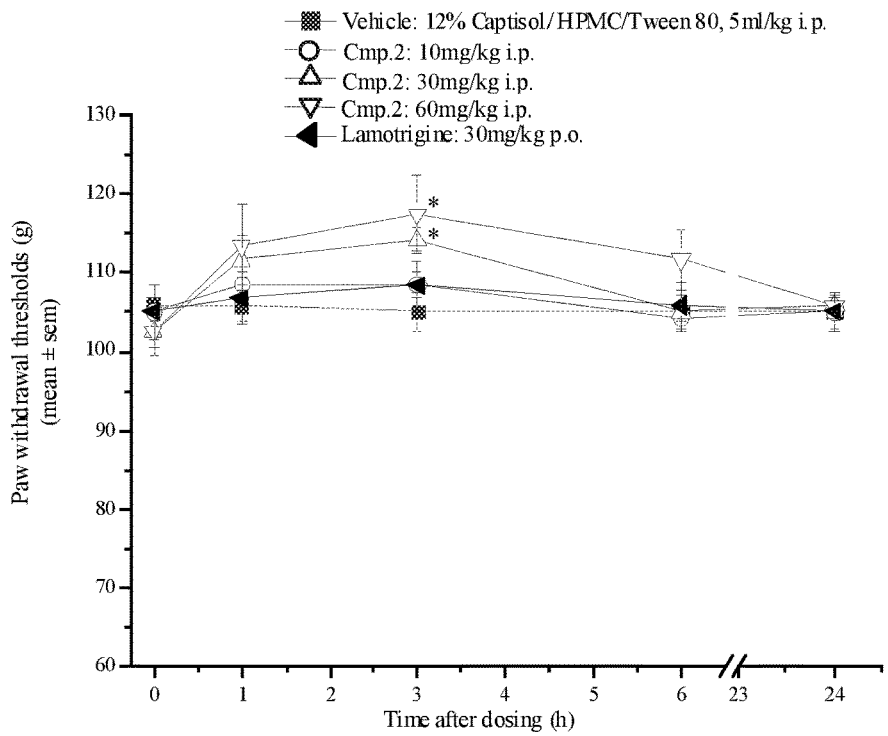
Figure 10A:
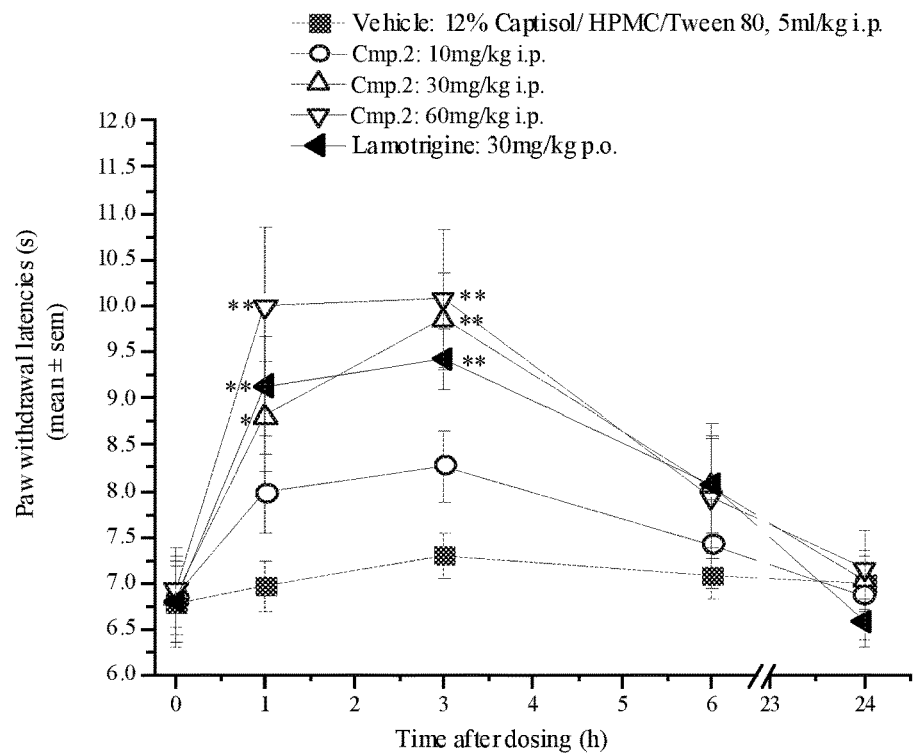
FIG. 10 shows the effect of Compound 2 on paw withdrawal thresholds to a cold stimulus (10° C.) in a neuropathic pain model (Study 2): ipsilateral paw (FIG. 10a); contralateral paw (FIG. 10b); and percentage reversals (FIG. 10c).
Figure 10B:
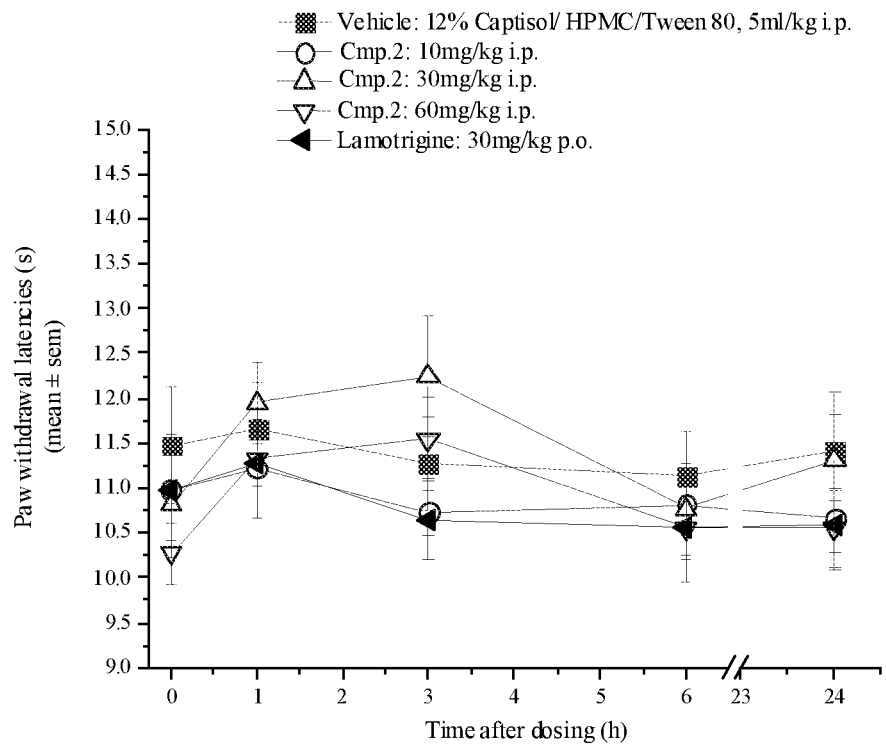

Fourteen days after nerve ligation, predose threshold readings of 66±1 g were measured in the ipsilateral paws compared to 104±1 g in the contralateral paws (FIG. 9a, FIG. 9b). Cold latencies of 6.8±0.1 s were measured in the ipsilateral paws compared to 10.8±0.2 s in the contralateral paws (FIG. 10a, FIG. 10b).

Figure 9C:
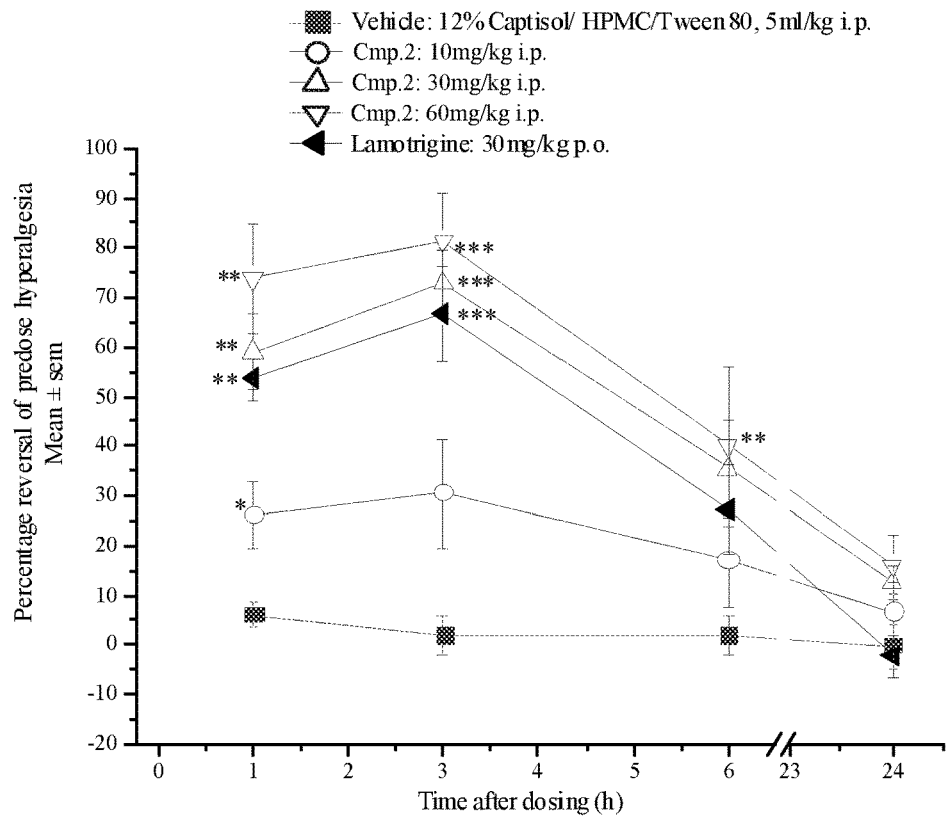
Figure 10C:
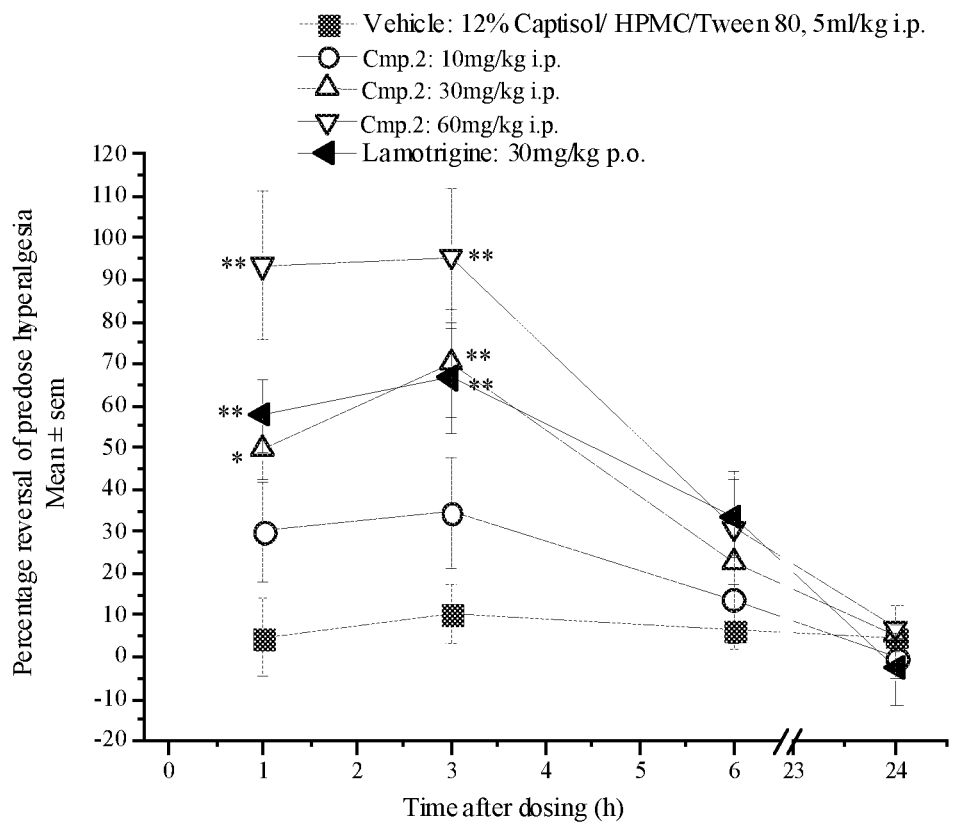

Compound 2 produced a dose-related reversal of mechanical (FIG. 9a, FIG. 9c) and cold sensitivity (FIG. 10a, FIG. 10c) with rapid onset of action.

Peak reversal of mechanical sensitivity was seen at 3 hours post-dose (31% at 10 mg/kg, 72% at 30 mg/kg and 81% by 60 mg/kg). Cold sensitivity was reversed at 3 hours post-dose by 35%, 70% and 95% by 10, 30 and 60 mg/kg respectively. The positive control, lamotrigine, gave peak reversals at 3 hours post-dose of 67% and 67% in mechanical and cold respectively.

There were small changes in contralateral paw withdrawals and latencies with Compound 2 which just attained significance at 3 hours on mechanical.

There were no apparent behavioural changes in the rats.

Inflammatory Pain Study

The intraplantar injection of FCA resulted in a marked decrease in withdrawal threshold to a mechanical stimulus and in withdrawal latency to a cold stimulus of the affected paw. The mean naïve threshold readings were 106±1 g.

Figure 11A:
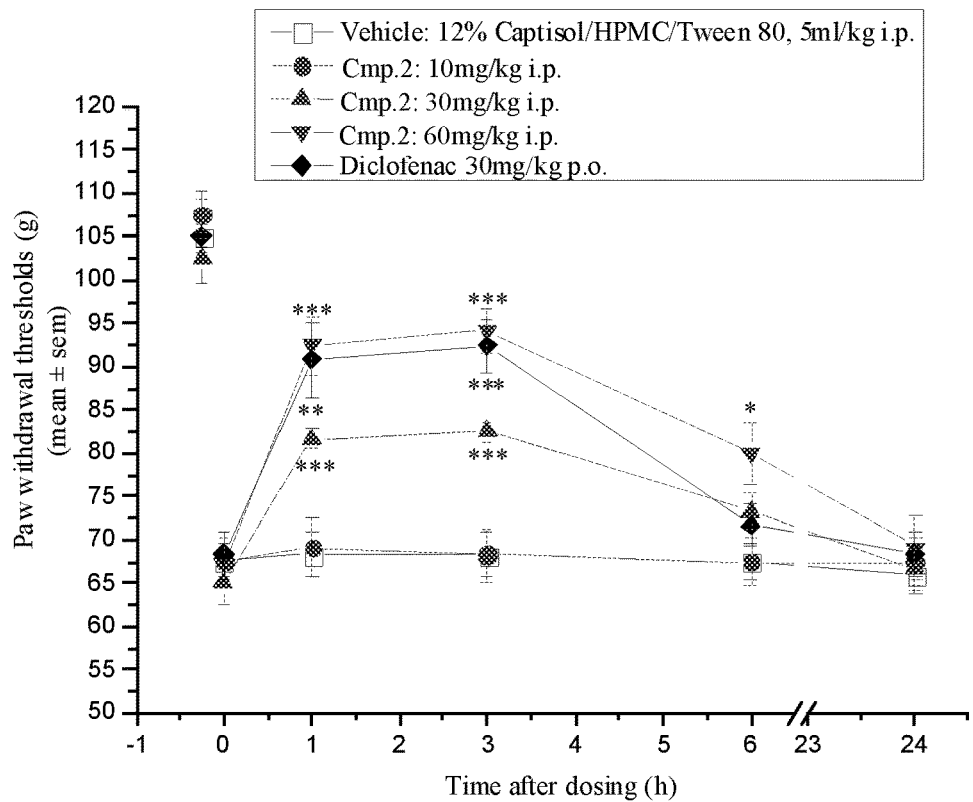
FIG. 11 shows the effect of Compound 2 on paw withdrawal thresholds under mechanical pressure in an inflammatory pain model: ipsilateral paw (FIG. 11a); contralateral paw (FIG. 11b); and percentage reversals (FIG. 11c).
Figure 11B:
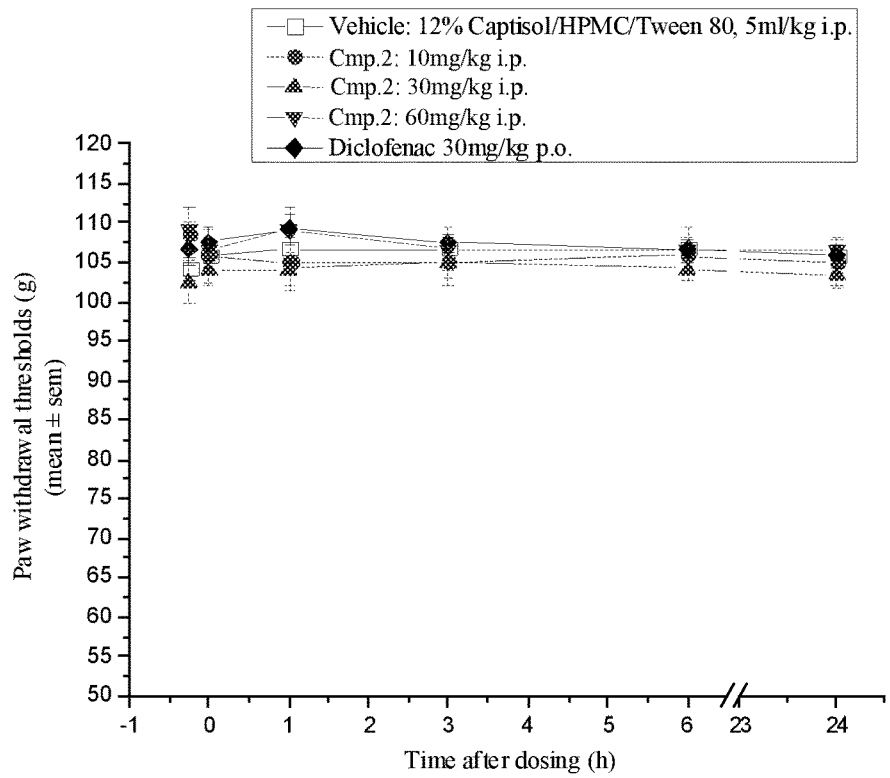
Figure 12A:
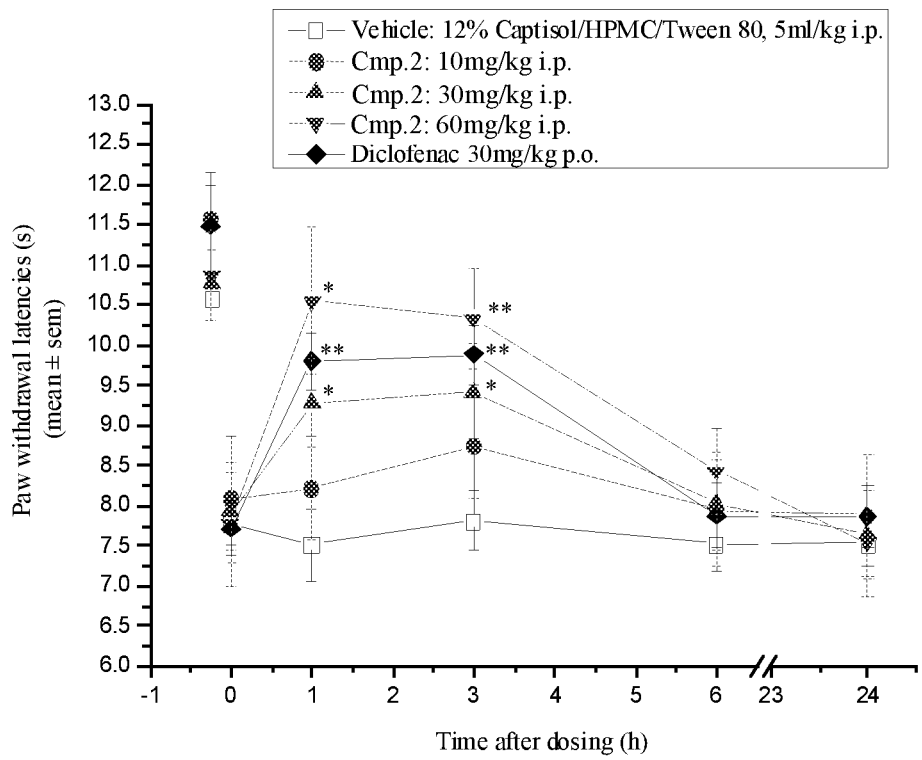
FIG. 12 shows the effect of Compound 2 on paw withdrawal thresholds to a cold stimulus (10° C.) in an inflammatory pain model: ipsilateral paw (FIG. 12a); contralateral paw (FIG. 12b); and percentage reversals (FIG. 12c).
Figure 12B:
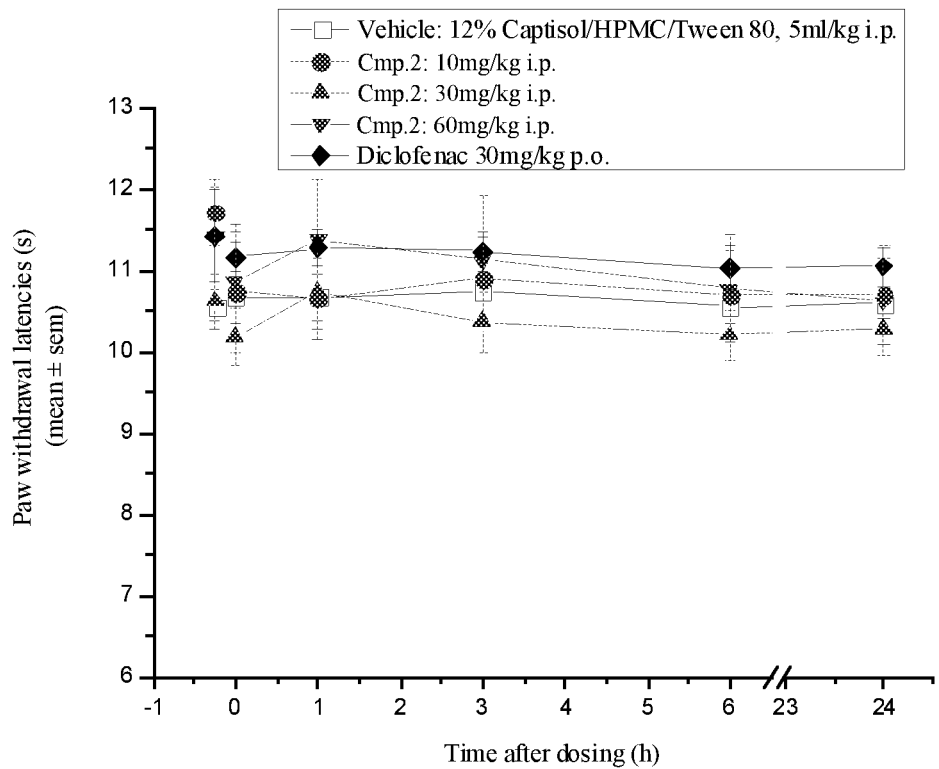

Twenty-four hours after FCA injection, predose threshold readings of 67±1.0 g were measured in the ipsilateral paws compared to 106±1.0 g in the contralateral paws (FIG. 11a, FIG. 11b). The mean naïve cold latency readings were 11.1±0.2 s. Twenty-four hours after FCA injection, predose threshold readings of 7.9±0.2 s were measured in the ipsilateral paws compared to 10.7±0.2 s in the contralateral paws (FIG. 12a, FIG. 12b).

Figure 11C:
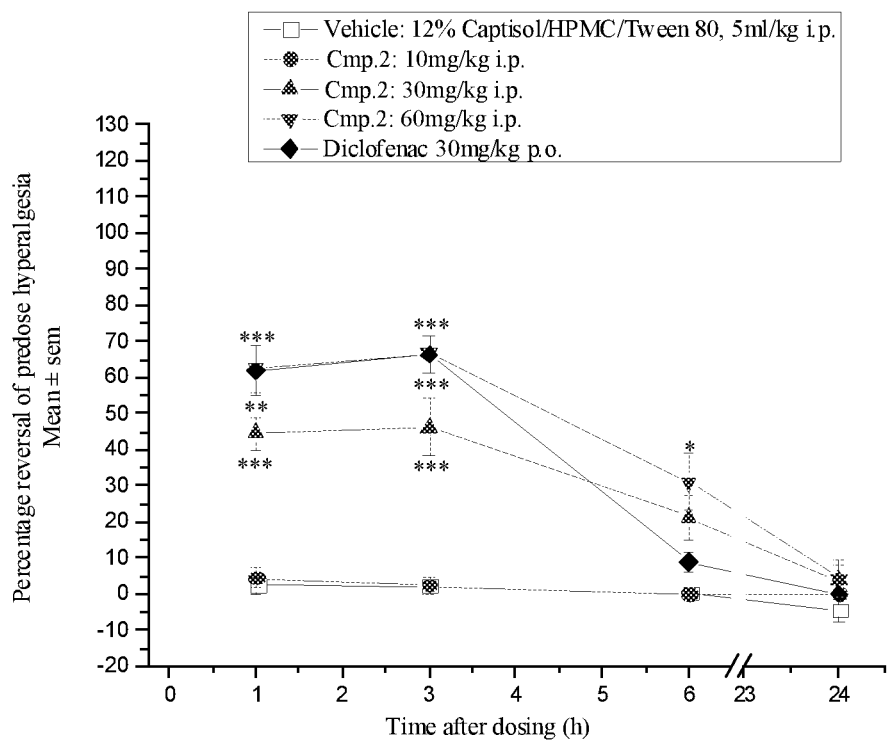
Figure 12C:
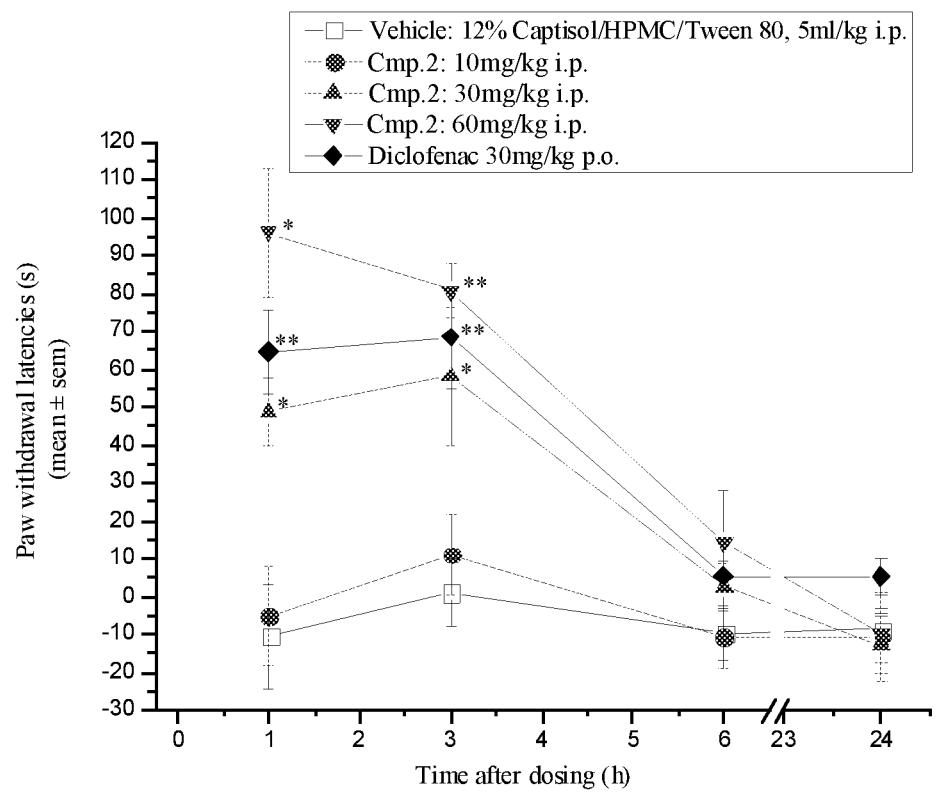

Compound 2 produced a dose-related reversal of both mechanical (FIG. 11a, FIG. 11c) and cold sensitivity (FIG. 12a, FIG. 12c) with rapid onset of action and peak reversal at 1-3 h post-dose.

Peak reversal of mechanical sensitivity was seen at 3 hours post-dose (46% at 10 mg/kg and 67% at 60 mg/kg). Peak reversal of cold sensitivity was seen at 1 hour post-dose (96% with 60 mg/kg), and seen at 3 hours post-dose for 30 mg/kg (58% reversal). At 3 hours post-dose, the compound was still efficacious at 60 mg/kg (81% reversal).

The cold sensitivity was particularly good in this study. Following FCA at 24 h the paw swelling often results in variable cold withdrawal latencies. Here, although more variable than the mechanical readouts, there were fairly consistent withdrawals latencies to cold.

The positive control, diclofenac, gave peak reversals at 3 hours post-dose of 66% and 69% in mechanical and cold respectively.

No changes in contralateral paw withdrawals or latencies were seen with Compound 2.

There were no apparent behavioural changes in the rats.

Compound 3

Neuropathic Pain Study

Partial ligation of the sciatic nerve resulted in a marked decrease in withdrawal threshold to a mechanical stimulus and in withdrawal latency to a cold stimulus of the affected paw.

Figure 13A:
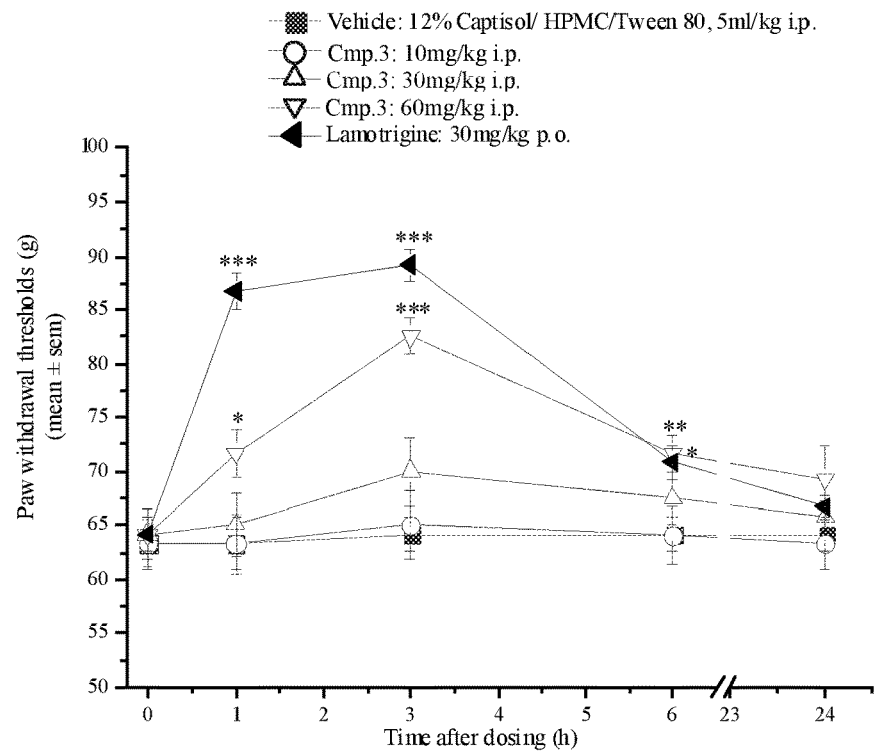
FIG. 13 shows the effect of Compound 3 on paw withdrawal thresholds under mechanical pressure in a neuropathic pain model: ipsilateral paw (FIG. 13a); contralateral paw (FIG. 13b); and percentage reversals (FIG. 13c).
Figure 13B:
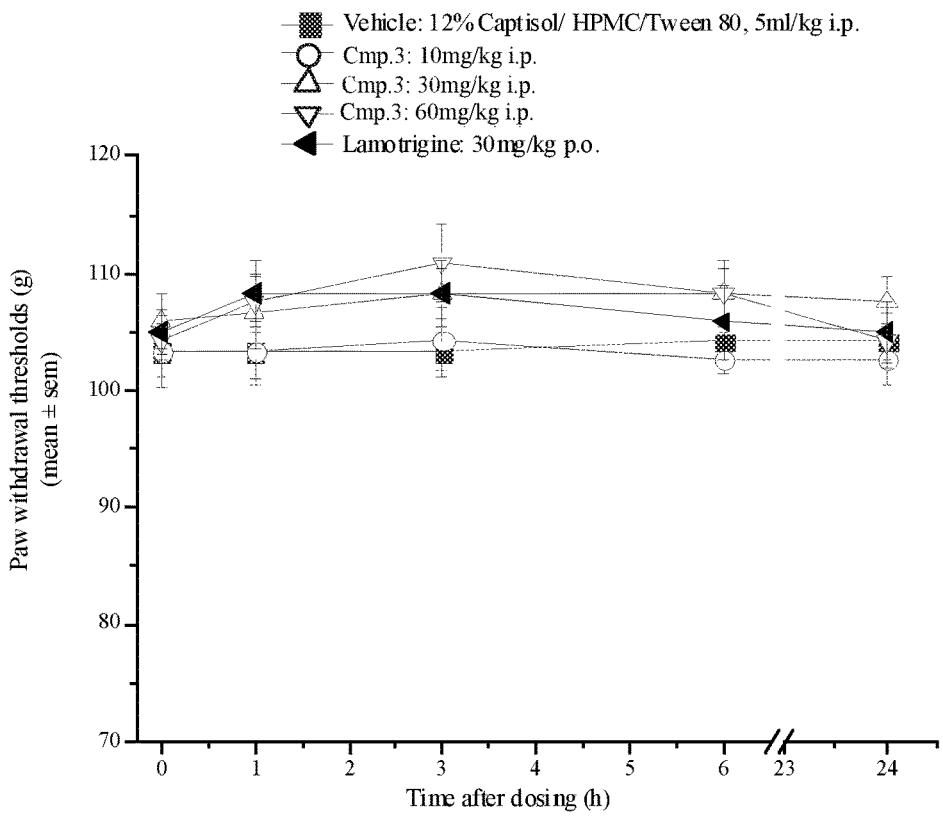
Figure 14A:
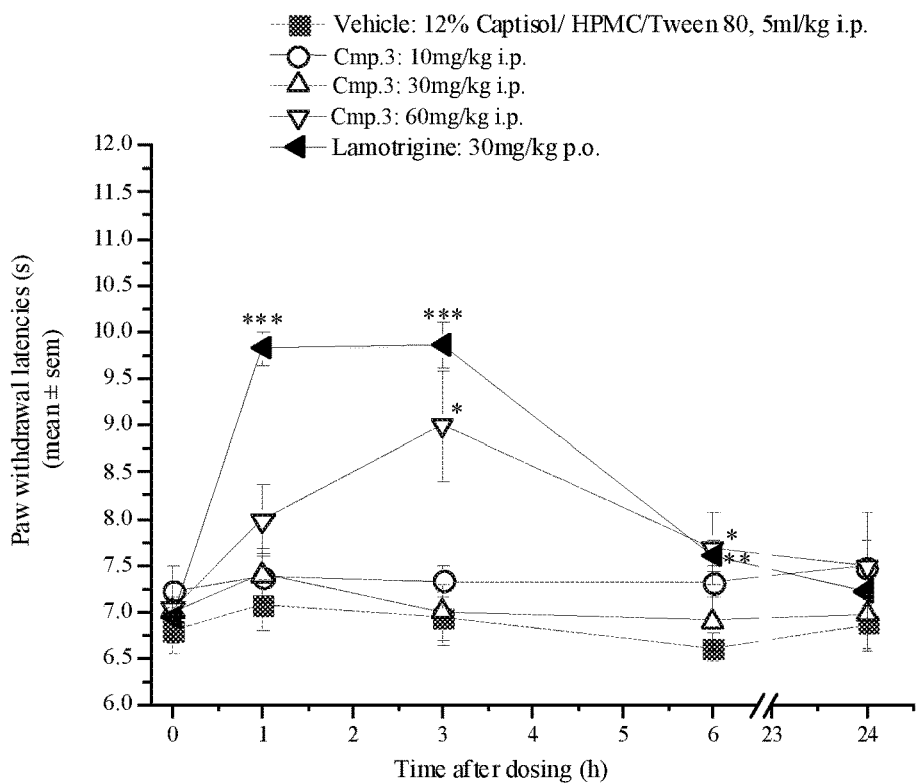
FIG. 14 shows the effect of Compound 3 on paw withdrawal thresholds to a cold stimulus (10° C.) in a neuropathic pain model: ipsilateral paw (FIG. 14a); contralateral paw (FIG. 14b); and percentage reversals (FIG. 14c).
Figure 14B:
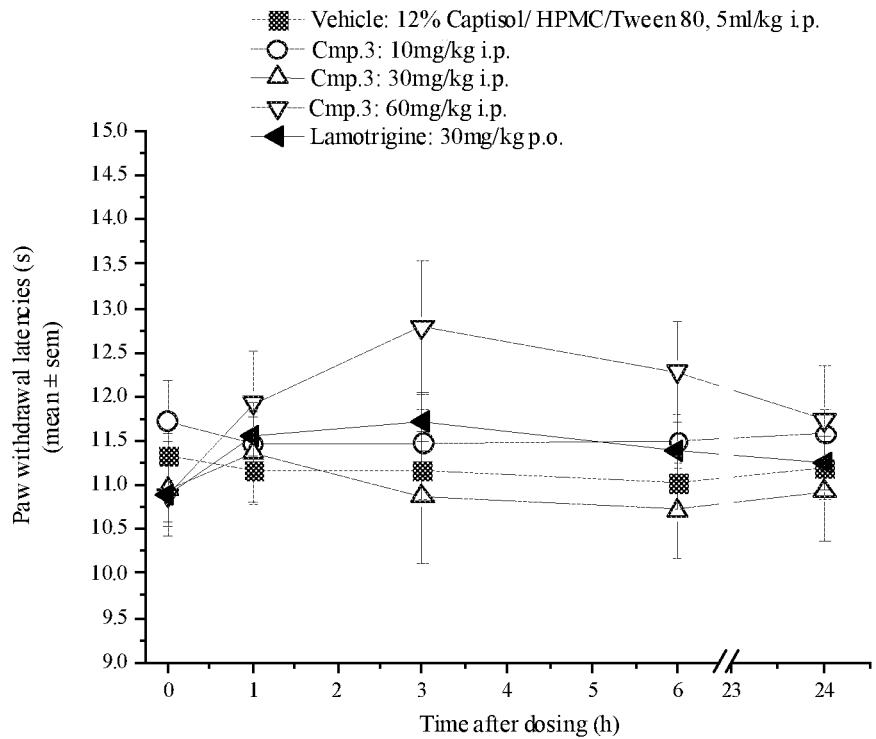

Fourteen days after nerve ligation, predose threshold readings of 64±1 g were measured in the ipsilateral paws compared to 104±1 g in the contralateral paws (FIG. 13a, FIG. 13b). Cold latencies of 7.0±0.2 s were measured in the ipsilateral paws compared to 11.2±0.2 s in the contralateral paws (FIG. 14a, FIG. 14b).

Figure 13C:
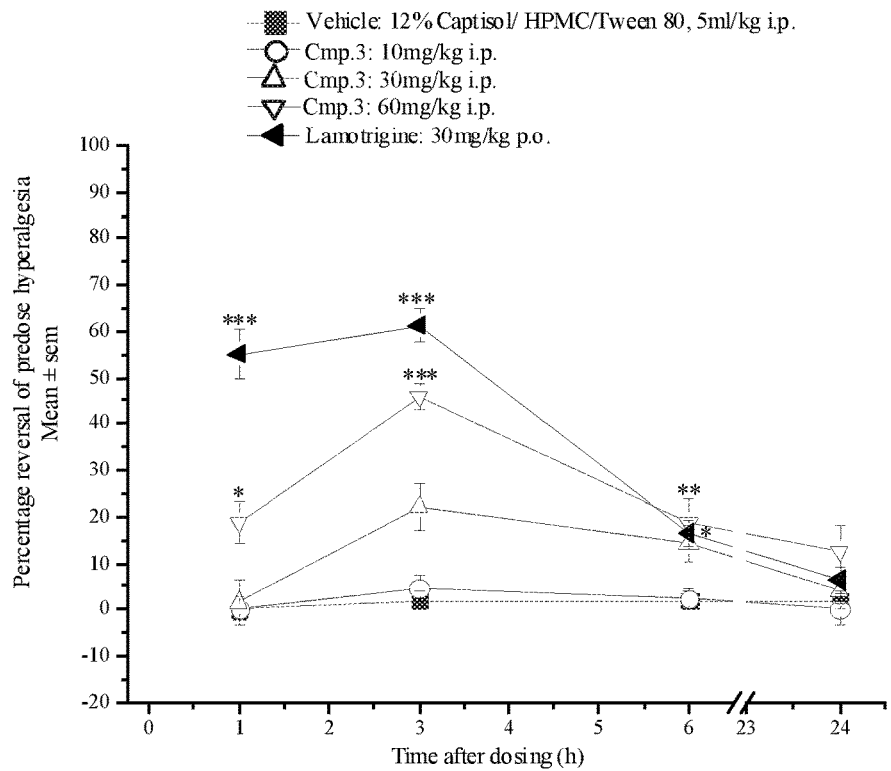
Figure 14C:
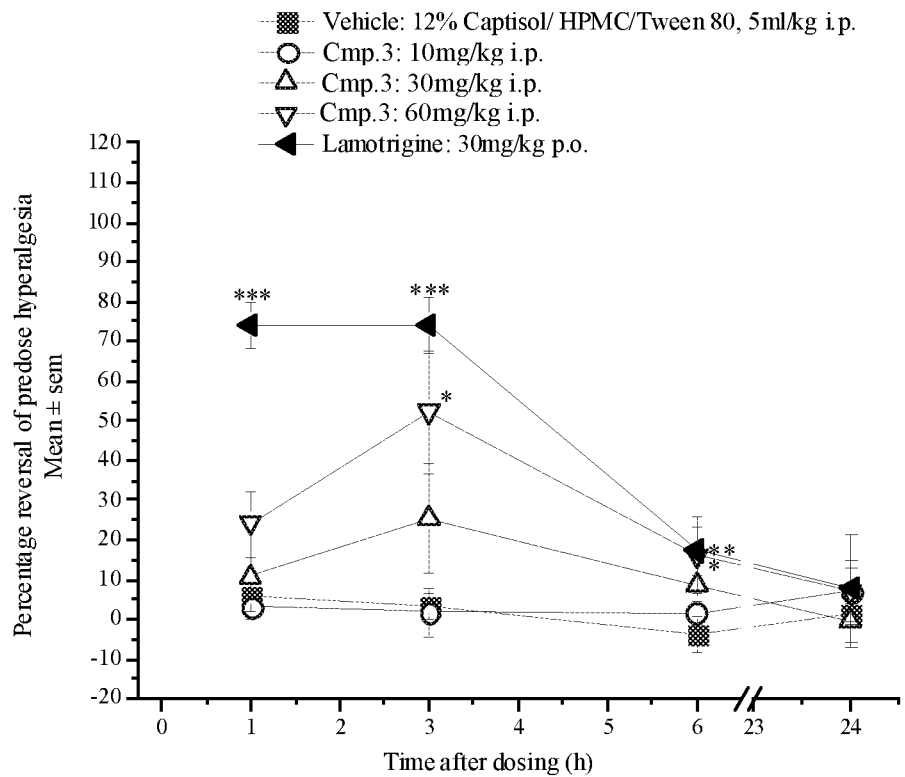

Compound 3 produced a dose-related reversal of both mechanical (FIG. 13a, FIG. 13c) and cold sensitivity (FIG. 14a, FIG. 14c) with slow onset of action.

Peak reversal of mechanical sensitivity was seen at 3 hours post-dose (46% at 60 mg/kg) after which it declined and activity was still evident at 6 hours post-dose. Cold sensitivity was reversed by 52% at 60 mg/kg at 3 hours post-dose. A dose level of 60 mg/kg attained statistical significance against mechanical and cold hyperalgesia. The positive control, lamotrigine, gave peak reversals at 3 hours post-dose of 61% and 74% in mechanical and cold respectively.

There were no significant changes in the contralateral paw withdrawals/latencies following treatment with Compound 3 and no behavioural changes noted.

Inflammatory Pain Study

The intraplantar injection of FCA resulted in a marked decrease in withdrawal threshold to a mechanical stimulus and in withdrawal latency to a cold stimulus of the affected paw.

Figure 15A:
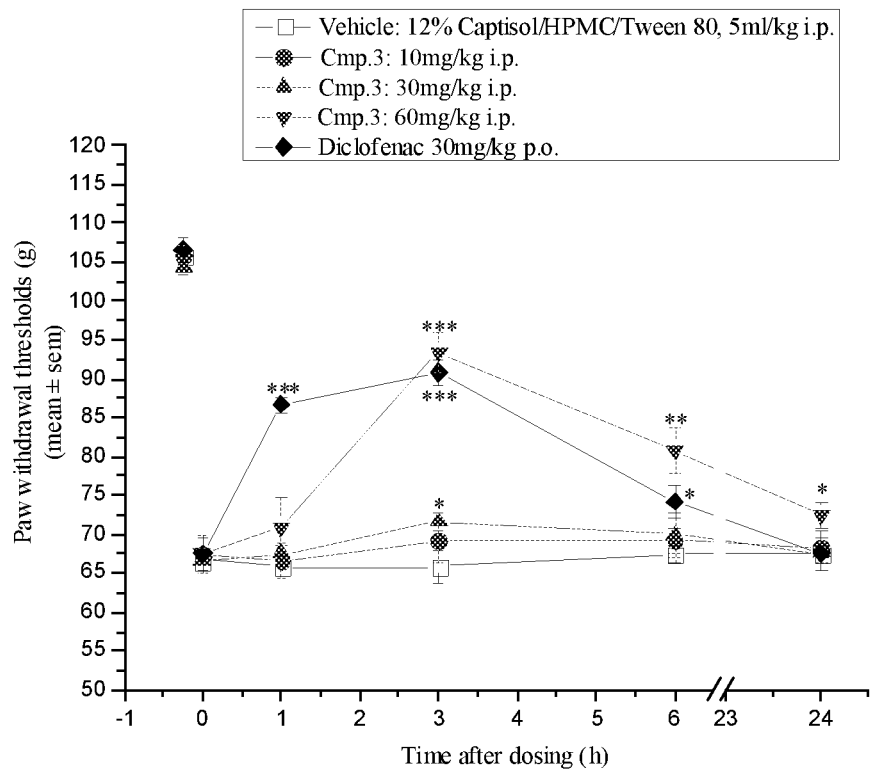
FIG. 15 shows the effect of Compound 3 on paw withdrawal thresholds under mechanical pressure in an inflammatory pain model: ipsilateral paw (FIG. 15a); contralateral paw (FIG. 15b); and percentage reversals (FIG. 15c).
Figure 15C:
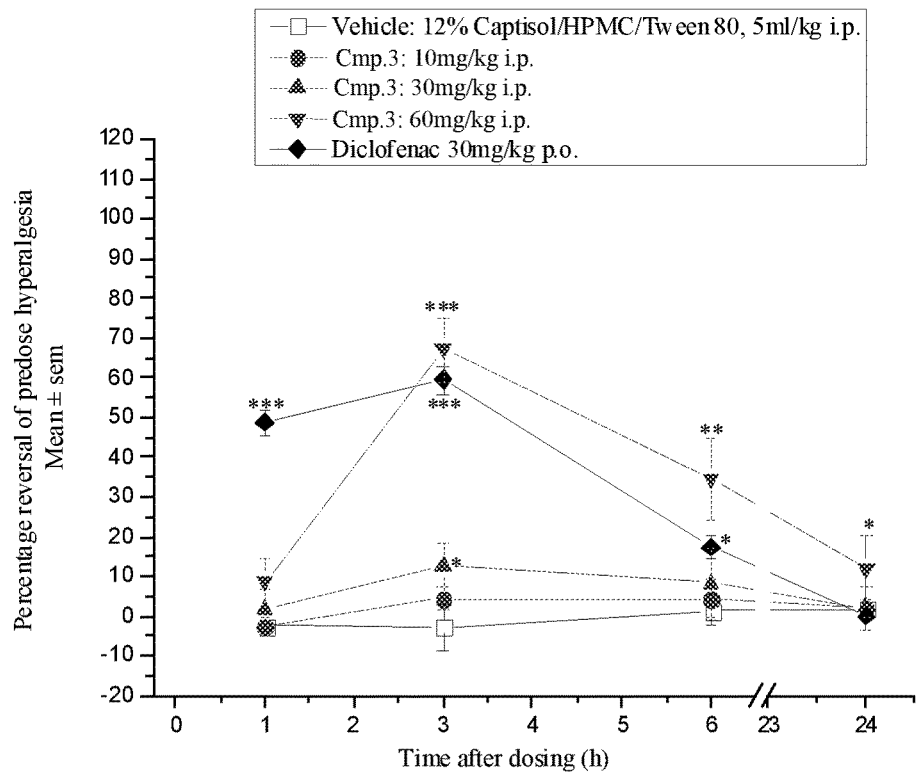
Figure 16A:
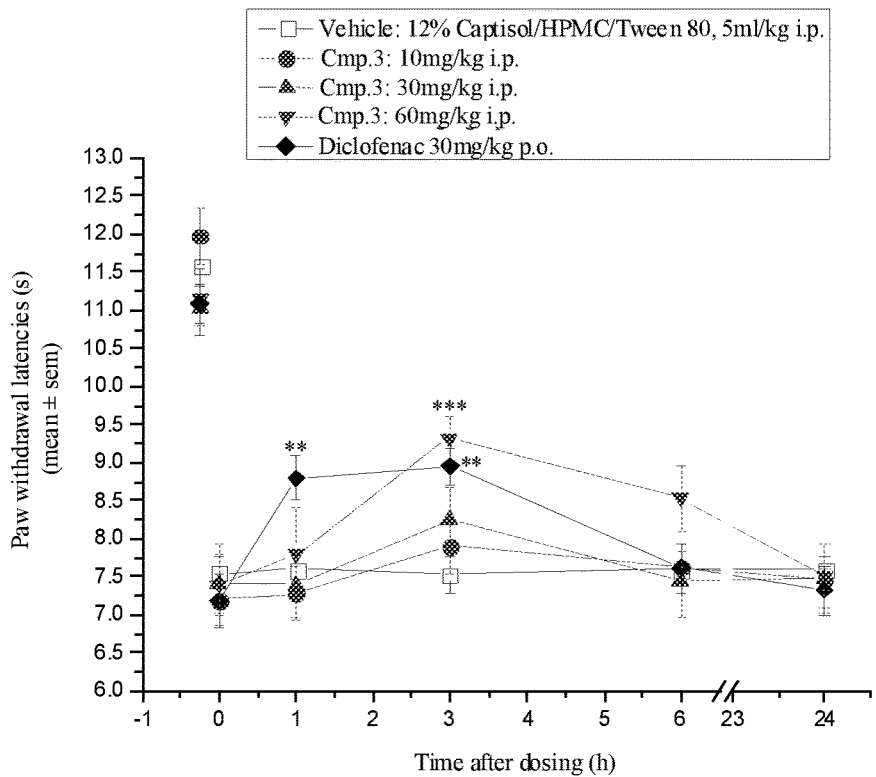
FIG. 16 shows the effect of Compound 3 on paw withdrawal thresholds to a cold stimulus (10° C.) in an inflammatory pain model: ipsilateral paw (FIG. 16a); contralateral paw (FIG. 16b); and percentage reversals (FIG. 16c).
Figure 16B:
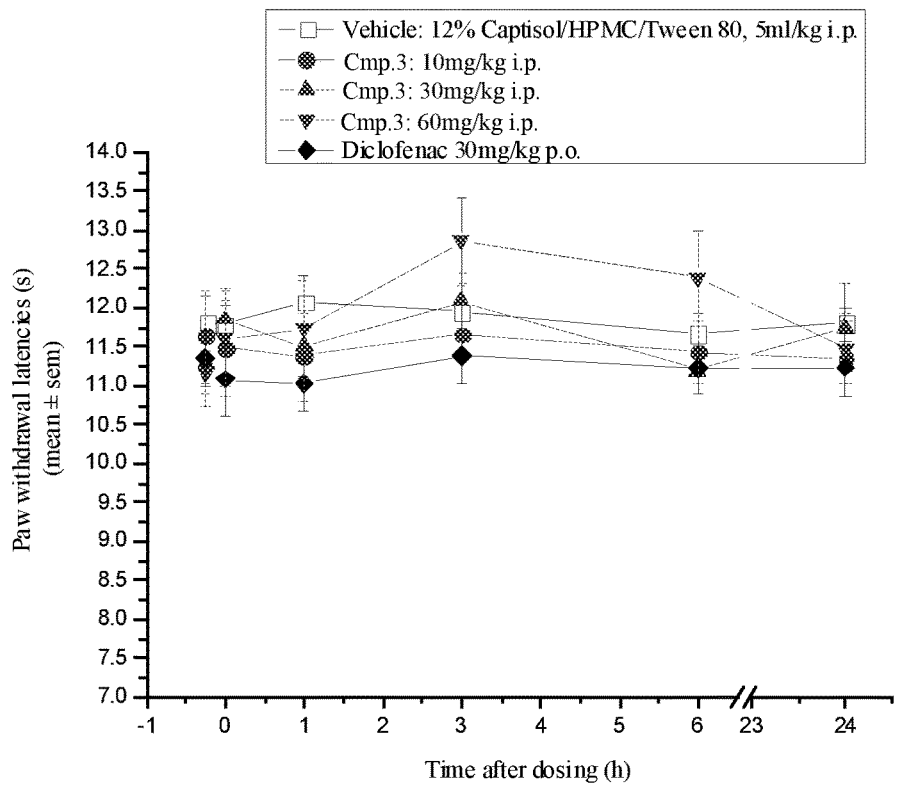
Figure 16C:
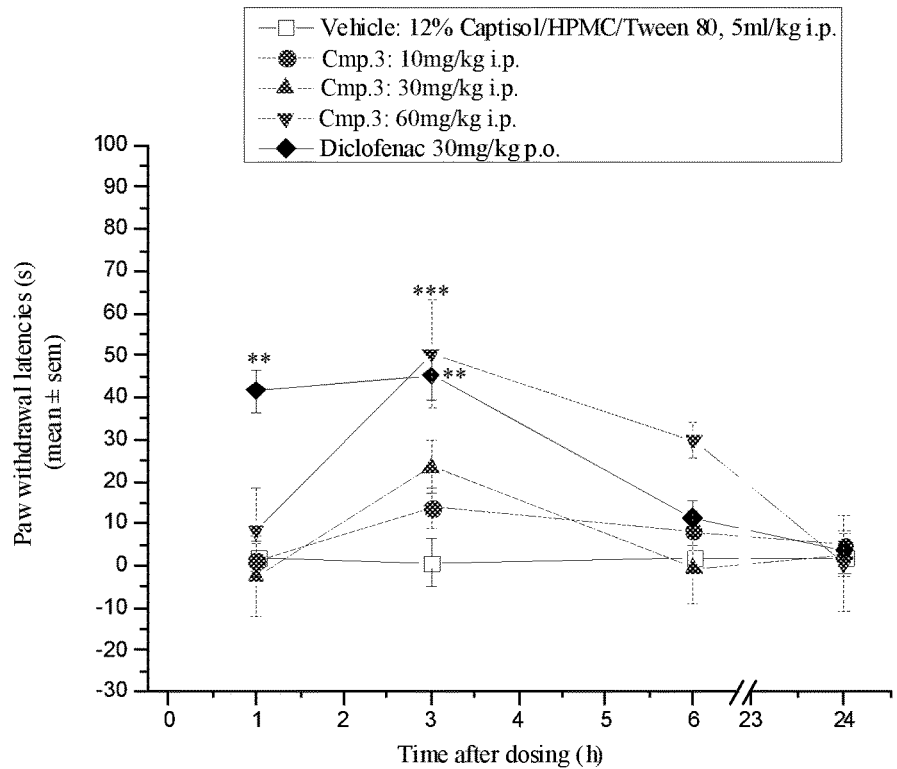

Only the top dose of example Compound 3 produced a reversal of either mechanical (FIG. 15a, FIG. 15c) or cold sensitivity (FIG. 16a, FIG. 16c). The compound had a slow onset of action, with little reversal evident at 1 hour post-dose. Peak reversal was seen at 3 h post-dose for both mechanical and cold sensitivity after which it declined but activity still evident at 6 hours post-dose (significant on mechanical thresholds).

At 3 hours post-dose, mechanical sensitivity was reversed by 67% and cold sensitivity was reversed by 51% both at 60 mg/kg. The positive control, diclofenac, gave peak reversals at 3 hours post-dose of 60% and 45% in mechanical and cold respectively.

Figure 15B:
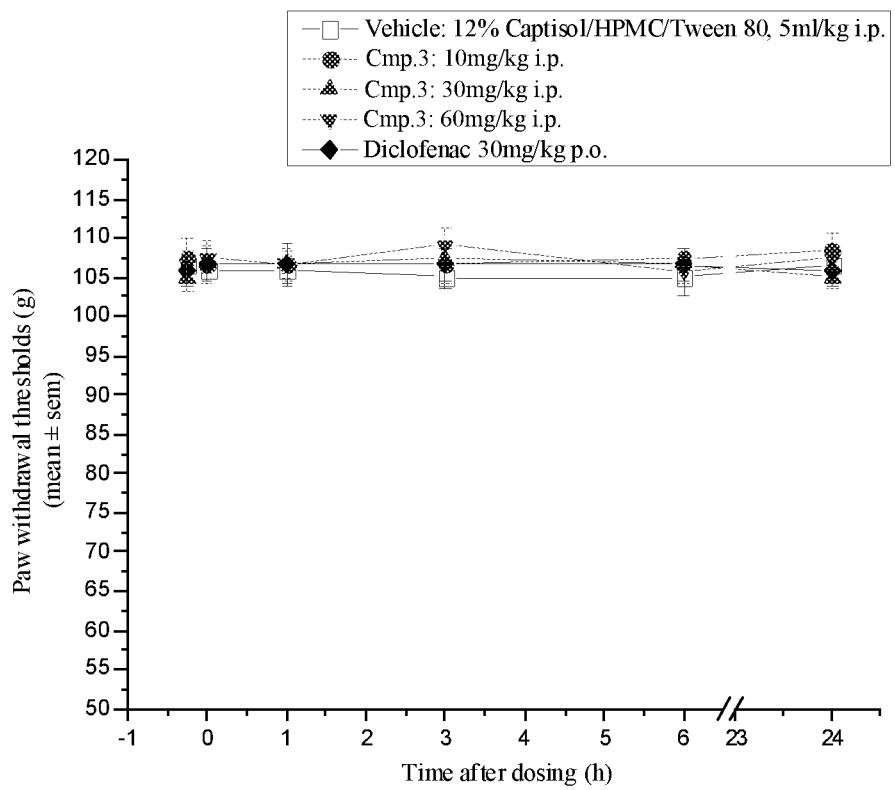

There were no significant changes in the contralateral paw withdrawals/latencies following treatment with example Compound 3 (FIG. 15b and FIG. 16b). The only behavioural observation was that 4/6 rats in the 30 mg/kg group and 1/6 rats in the 60 mg/kg group appeared to be more alert and more vocal than fellow cage-mates (1-6 h post-dose).

Compound 4

Inflammatory Pain Study

Figure 17A:
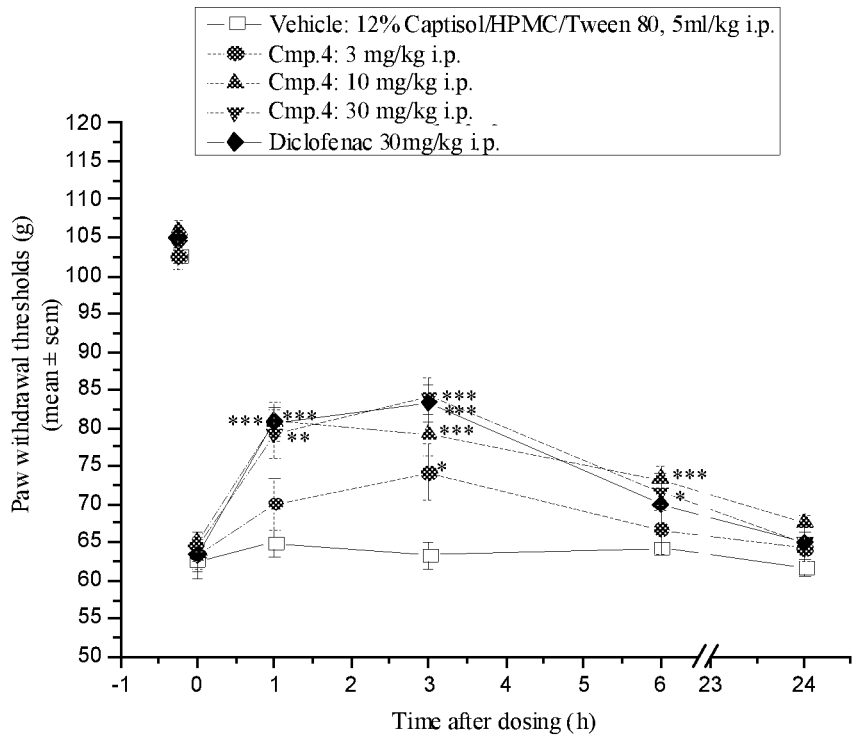
FIG. 17 shows the effect of Compound 4 on paw withdrawal thresholds under mechanical pressure in an inflammatory pain model: ipsilateral paw (FIG. 17a); contralateral paw (FIG. 17b); and percentage reversals (FIG. 17c).
Figure 17B:
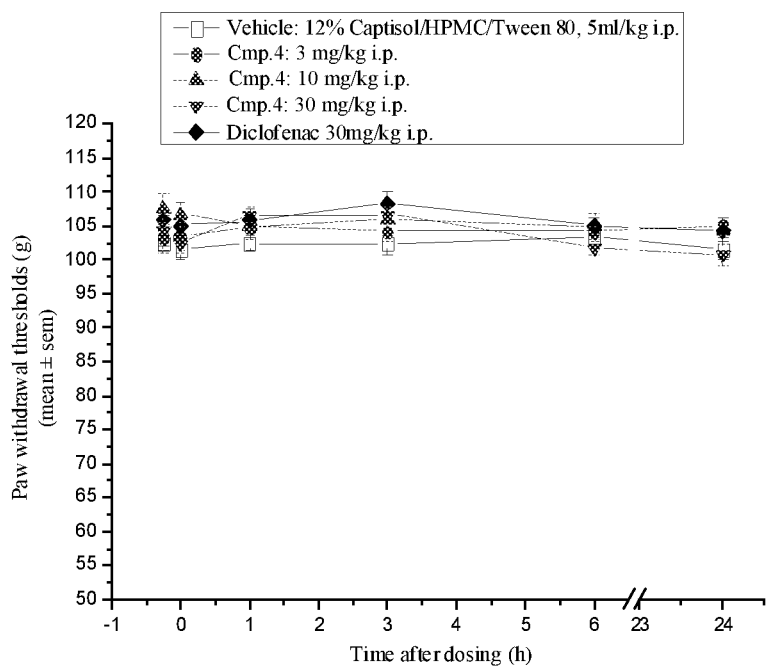
Figure 18A:
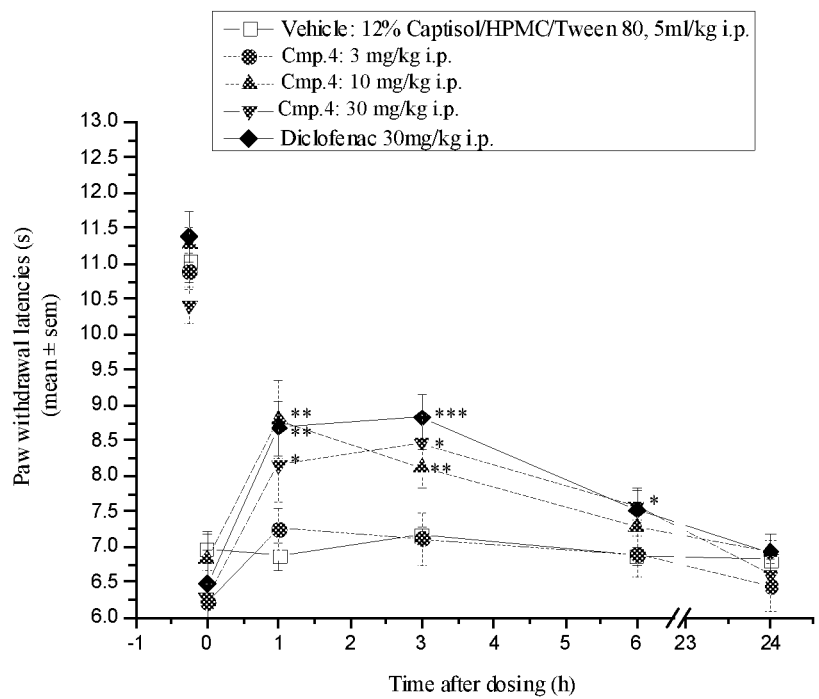
FIG. 18 shows the effect of Compound 4 on paw withdrawal thresholds to a cold stimulus (10° C.) in an inflammatory pain model: ipsilateral paw (FIG. 18a); contralateral paw (FIG. 18b); and percentage reversals (FIG. 18c).
Figure 18B:
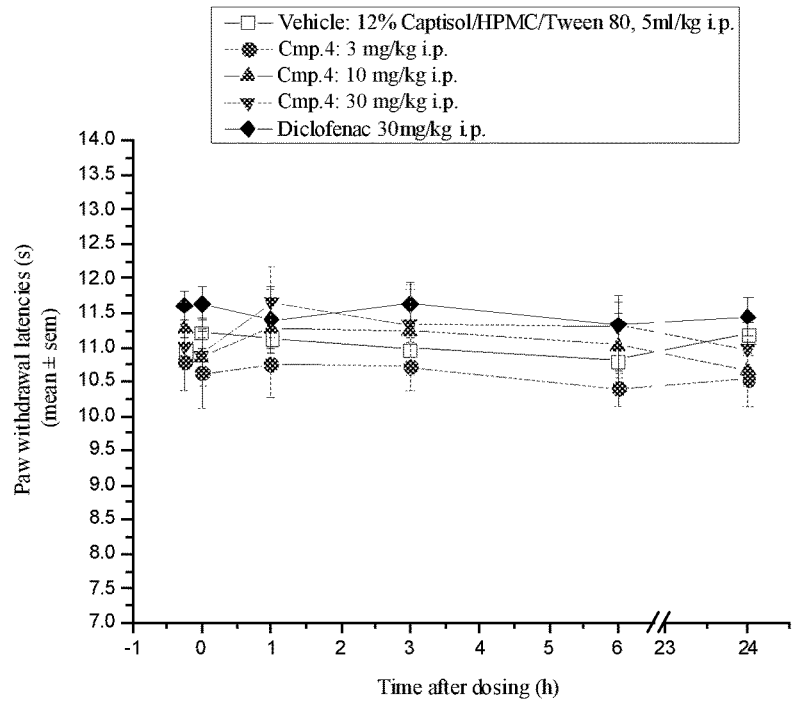

The intraplantar injection of FCA resulted in a marked decrease in withdrawal threshold to a mechanical stimulus and in withdrawal latency to a cold stimulus of the affected paw. The mean naïve threshold readings were 104±1 g. Twenty-four hours after FCA injection, predose threshold readings of 64±1.0 g were measured in the ipsilateral paws compared to 104±1.0 g in the contralateral paws (FIG. 17a, FIG. 17b). The mean naïve cold latency readings were 11.1±0.1 s. Twenty-four hours after FCA injection, predose threshold readings of 6.6±0.2 s were measured in the ipsilateral paws compared to 11.0±0.2 s in the contralateral paws (FIG. 18a, FIG. 18b).

Figure 17C:
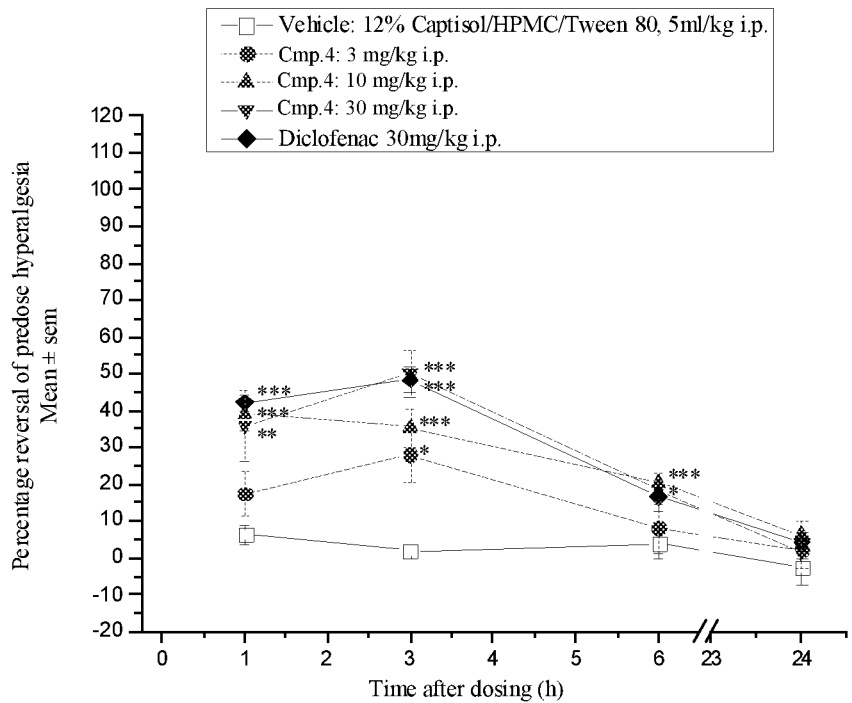
Figure 18C:
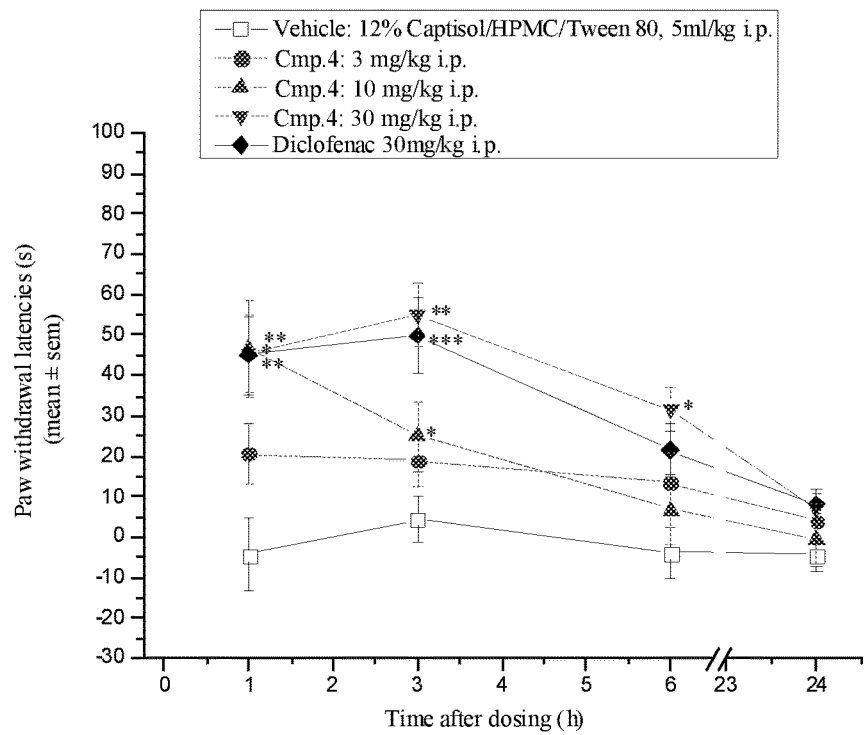

Compound 4 produced a reversal of the mechanical (FIG. 17a, FIG. 17c) and cold hyperalgesia (FIG. 18a, FIG. 18c) that was largely dose-related. The compound had peak reversal at 1-3 h post-dose after which it declined, but significant activity still evident at 6 h post-dose.

Mechanical sensitivity was reversed by 50% and cold sensitivity was reversed by 55% with the 30 mg/kg dose. The positive control, diclofenac, gave reversals of 49% and 50% in mechanical and cold respectively. At 30 mg/kg the compound had similar efficacy and potency to diclofenac.

There were no significant changes in the contralateral paw withdrawals/latencies following treatment with Compound 4 and no behavioural changes noted.

CONCLUSIONS

In a rat models of neuropathic and inflammatory pain, Compounds 1, 2, and 3, which are structurally diverse selective modulators of Kv3.1 and/or Kv3.2 and/or Kv3.3 channels, were all effective at reversing behavioural measures of pain when administered acutely, but without causing significant changes in normal behaviour. Additionally, in the rat model of inflammatory pain, Compound 4, which is a selective modulator of Kv3.1 and/or Kv3.2 and/or Kv3.3 channels, was effective at reversing behavioural measures of pain when administered acutely, but without causing significant changes in normal behaviour. These data strongly support the proposition that modulation of Kv3.1 and/or Kv3.2 and/or Kv3.3 channels has potential in the treatment of pain.

Example 3: Specificity of Compounds as Potentiators of Kv3.1 and/or 3.2 and/or 3.3

To confirm that the utility of Compounds 1, 2, 3 and 4 derives from their ability to potentiate Kv3.1 and/or 3.2 and/or 3.3 channel activity, the ability of the compounds to potentiate other pain associated targets was investigated.

Methods

Kv3.4 Assay 1

The effect of compounds on human cloned Kv3.4 channels expressed stably in a HEK293 call line was evaluated at room temperature using the QPatch HT® (Sophion Bioscience A/S, Denmark), an automatic parallel patch clamp system. Compounds were evaluated at 10 µM in three cells. The duration of exposure to each test article concentration was 5 minutes.

In preparation for a recording session, intracellular solution was loaded into the intracellular compartments of the QPlate and cell suspension was pipetted into the extracellular compartments. After establishment of a whole-cell configuration, membrane currents were recorded using up to 48 parallel patch clamp amplifiers in the QPatch HT® system. The current records were sampled at 2000 Hz and low-pass Bessel filtered at 400 Hz.

Valid whole-cell recordings met the following criteria:
1. Seal resistance (Rseal)≥200 MΩ.
2. Leak current≤25% channel current.

Kv3.4 Assay 2

Human Kv3.4 channels were stably expressed in a HEK293 cell line. Cells were used within 1-4 hours of cell preparation and internal and external physiological solutions were freshly prepared prior to the assay. Electrophysiological recordings were made using an automated patch clamp platform (QPatch, Sophion Biosciences). The extracellular solution contained 145 mM NaCl, 4 mM KCl, 2 mM $CaCl_2$, 1 mM $MgCl_2$, 10 mM HEPES and 10 mM glucose; the pH was adjusted to 7.4 with NaOH, and the osmolarity measured as 313 mOsm/L. A low potassium intracellular solution was used which contained 135.6 mM CsCl, 5.37 mM $CaCl_2$, 1.75 mM $MgCl_2$, 10 mM EGTA, 15.6 mM KOH, 4 mM $Na_2ATP$ and 10 mM HEPES; the pH was adjusted to 7.2 with CsOH, and the osmolarity measured as 303 mOsm/L.

The voltage dependence of inactivation of the homomeric hKv3.4 channels was tested using a protocol that consisted of a series of two square voltage pulses. The pulse one (P1=pre-pulse) was 1000 ms long and was immediately followed by a second pulse (P2=test pulse) which was 500 ms long. Pulse one varied between the holding potential of −60 mV to +40 mV and pulse two stepped from a holding potential of −60 to +40 mV before returning to the holding potential of −60 mV.

Steady-state voltage-activation and -inactivation curves were fitted with single Boltzmann function in which G/Gmax was obtained from normalized current amplitude and the $V_{50}$ represent the half-activation or inactivation voltage.

The time constants of the inactivation phase of the hKv3.4 currents were derived from a mono ($\tau$) or a double ($\tau_1$ and $\tau_2$) standard exponential fit to peak trace pulse from −80 mV to +60 mV.

The time-course of effect of the compounds against the hKv3.4 potassium channel was measured with repetitive voltage pulses from a holding potential of −60 mV, with pulses of 500 ms duration every 5 s to +40 mV.

One concentration (10 uM) of the test compounds was assessed during the activation, inactivation and peak pulse protocols. The protocol was applied with addition of physiological solution (control period), followed by 10 uM of the testing compound and a 10 mM of the standard blocker TEA.

Data were normalized using the baseline current control values as top of the curve (maximum current; 1.0) and the zero potassium current as the bottom of the curve (minimum current; 0.0).

Series resistance and quality of seals were monitored during the experiments. Analysis was performed using the Sophion QPatch Assay Software (version 5.2).

Stock solutions (10 mM) of the standard blockers TEA was prepared in fresh physiological solution prior to testing on the e-phys automated platform. The test compounds were prepared in 10 mM DMSO stock and then diluted 1 in 1000 in physiological solution.

Kv3.4 Assay 3 hKv3.4 channels were heterologously expressed in *Xenopus* ooctyes following microinjection of in vitro transcribed mRNA (mMessage mMachine kit, Ambion, Austin, Tex.). Whole-oocyte currents were recorded 1-4 day post-microinjection at room temperature (21-23° C.) under two-electrode voltage-clamp conditions (OC-725C, Warner, Hamden, Conn.). ND-96 and ND-96 plus the test compound were delivered using a gravity-driven perfusion system.

Whole-oocyte currents mediated by hKv3.4 channels were elicited by 400 ms depolarizing steps from −40 to 60 mV in 10 mV increments from a holding potential of −100 mV under in the absence and then presence of test compound. Voltage-conductance curves were constructed from the peak currents evoked at each voltage step, and the data were fitted to a Boltzmann equation.

Data acquisition, leak subtraction and initial analyses were performed using pClamp 9.2/10.3 (Molecular Devices, Sunnyvale, Calif.). Macroscopic currents were low-pass filtered at 0.5-1 kHz and digitized at 1-2 kHz. Leak and capacitive currents were subtracted on line using a p/4 subtraction strategy. *Xenopus laevis* frogs were handled according IACUC approved protocols and regulations.

Kv7.2/7.3

Human Kv7.2/7.3 heteromeric channels were stably expressed in a HEK293 cell line. Cells were plated onto 13 mm plastic dishes and incubated for 1-3 days in a 5% $CO_2$ incubator for conventional whole-cell patch clamp experiments. Electrophysiological recordings were made using an automated patch clamp platform (QPatch, Sophion Biosciences). Internal (pipette) solution contained (in mM): K-Aspartate (130), KCl (15), $MgCl_2$ (5.5), $Na_2ATP$ (5), $K_2PCr$ (5), EGTA (20), HEPES (10), pH 7.25 with KOH, was used to study Kv7.2/7.3 currents. Cells were superfused at room temperature with a standard physiological solution containing (mM): NaCl (140), KCl (4), $CaCl_2$ (2), $MgCl_2$ (1), glucose (10), HEPES (10), pH 7.35 with NaOH.

Patch pipettes were pulled from borosilicate glass and had tip resistances of 2-4 MW when filled with the above solution. Capacitative transients were compensated electronically from the recordings. However, the voltage drop across the series resistance and the liquid junction potential were not compensated. The series resistance was generally less than 10 MG (n=5 cells), with a mean cell capacity of 25±5 pF.

In some cases, manual patch clamp was carried out using an Axon 200B amplifier (Axon Instruments). The software program pClamp (version 10) from Axon Instruments was used to stimulate and record electrical activity. GraphPad Prism (version 5) software was used to analyse the data.

To activate Kv7.2/7.3 currents, steady-state voltage pulses (1 s) were applied every 10 s from a holding potential of −80 mV to +60 mV, in 10 mV steps. Following a control period of at least 3 min, compounds were perfused for at least 3 min. The compounds were dissolved in 100% DMSO (at 10 mM) and subsequently diluted in a physiological solution without exceeding 0.1% DMSO in a final concentration of 10 µM. Concentration of 0.1% DMSO did not lead to significant effects on the amplitude of the fully activated peak of the hKv7.2/7.3 channel, which generally remain stable for the duration of a typical whole-cell recording.

Perfusion of the test compounds was started if cells had less than 10% run-down within a two full I-V control protocols. Cells with higher run-down were excluded from further analysis. Following perfusion of test compounds, agonist retigabine (from Alomone Labs, Israel) and blocker TEA (from Sigma) were tested in the same cells. Retigabine and TEA were prepared as 10 mM and 100 mM stock solution in DMSO and water, respectively. Stock solutions were subsequently diluted in physiological solutions at the final concentrations of 10 µM and 10 mM, respectively.

In this study, due to the limited number of experiments, statistical analysis was applied only when N=3 using the two-tailed paired t-test.

Nav1.7

Human Nav1.7 channels were stably expressed in a HEK293 cell line. Electrophysiological recordings were made at room temperature using an automated patch clamp platform (QPatch, Sophion Biosciences).

The QPatch assay was carried out at room temperature using the QPatch platform (Sophion). On the day of the experiment cells were cultured according to standard cell preparation for QPatch. Internal and external physiological solutions were freshly prepared prior to the assay. The standard extracellular solution contained 145 mM NaCl, 4 mM KCl, 2 mM $CaCl_2$, 2 mM $MgCl_2$, 10 mM HEPES and 10 mM glucose; the pH was adjusted to 7.4 with NaOH, and the osmolarity measured as 314 mOsm/L. The standard intracellular solution contained 140 mM CsF, 10 mM NaCl, 5 mM CsOH, 1 mM EGTA, 10 mM HEPES; the pH was adjusted to 7.25 with CsOH, and the osmolarity measured as 293 mOsm/L.

A series of 40 voltage pulses (from −120 mV to 0 mV, 2.4 ms long at 117 Hz) were applied every 60 s in control (twice), compound (five times), standard blocker (twice) and washout (twice). The % inhibition values were calculated by normalising the data relative to the 1st pulse (P1) and by calculating the ratio between the 40th pulse versus the 1st pulse (P40/1). Series resistance and quality of seals were monitored during the experiments. Sophion QPatch Assay Software 5.0 was used to analyse and plot all the graphs. 10 µM of the test compound was applied followed by 1 µM TTX (standard blocker), followed by saline (washout).

Compounds were diluted in physiological solutions at the required concentration with a maximum of 0.1% of DMSO.

BK

The effects of compounds on cloned human BK (hKCa1.1/β1) potassium channel (encoded by the human KCNMA1 and KCNMB1 genes) were examined in a CHO cell line using a QPatch HT® (Sophion Bioscience A/S, Denmark) assay. Onset and steady-state inhibition of hBK currents were measured using a voltage pulse pattern with a depolarizing test pulse (+100 mV amplitude, 200 ms duration) at 10 s intervals from a holding potential of −80 mV. The peak amplitude of the delayed outward current was measured for each test pulse. The compounds were evaluated at 10 µM in three cells for each compound, after a 3 minute compound application. The steady state inhibition produced by each compound was calculated.

Results hNav1.7

Compounds 1, 2 and 3 were tested at 10 µM concentration (N=3) in the Nav1.7 assay. No significant effect on Nav1.7-mediated currents was observed.

hBK

Compounds 1, 2 and 3 were tested at 10 µM concentration (N=3) in the BK assay. No significant effect on channel currents was observed.

hKv7.2/7.3

Compounds 1 and 2 were tested at 10 µM concentration (N=3) in the Kv7.2/7.3 assay. Neither compound was found to have a significant effect on Kv7.2/7.3-mediated currents.

hKv3.4

Compound 2 was tested at a 10 µM concentration (N=2) in the Kv3.4 assay 1. The compound did not potentiate the observed current.

Compounds 1, 2, 3 and 4 were tested at 10 µM concentration (N≥2) in the Kv3.4 assay 2. The compounds did not potentiate the observed current, and did not produce any notable shift in the voltage-dependence of activation of the Kv3.4 currents. However, in each case the compounds were associated with a reduction in peak Kv3.4 current (compound 1: 40±5%; compound 2: 45.4±4%; compound 3: 36±3%; compound 4: 50.0±4%), although these peak currents did not recover to baseline levels on washout of the compounds.

Compound 1 was tested at 10 µM concentration (N=6) in Kv3.4 assay 3 (manual patch with transiently transfected oocytes). No significant effect on Kv3.4 mediated channel currents was observed, and Compound 1 did not significantly shift the voltage-conductance curve for hK3.4.

All publications, including but not limited to patents and patent applications, cited in this specification are herein incorporated by reference as if each individual publication were specifically and individually indicated to be incorporated by reference herein as though fully set forth.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps. The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims which follow.

REFERENCES

Amarillo, Y., Santiago-Castillo, J. A., Dougherty, K., Maffie, J., Kwon, E., Covarrubias, M., & Rudy, B. (2008) *J. Physiol* 586, 2093-2106.

Aroniadou-Anderjaska V, Qashu F, Braga M F M. Mechanisms regulating GABAergic inhibitory transmission in the basolateral amygdala: implications for epilepsy and anxiety disorders. *Amino Acids* 2007 August; 32:305-315.

Atzori M, Lau D, Phillips Tansey E, Chow A, Ozaita A, Rudy B, McBain C J. $H_2$ histamine receptor-phosphorylation of Kv3.2 modulates interneuron fast spiking. *Nat. Neurosci.* 2000 August; 3(8):791-798.

Baranauskas G, Nistri A. Sensitization of pain pathways in the spinal cord: cellular mechanisms. *Prog. Neurobiol.* 1998 February; 54(3):349-65.

Baron R, Hans G, Dickenson A H. Peripheral input and its importance for central sensitization. *Ann. Neurol.* 2013 November; 74(5):630-6.

Beck, E. J., Sorensen, R. G., Slater, S. J., & Covarrubias, M. (1998) *Journal of General Physiology* 112, 71-84.

Ben-Ari Y. Seizure Beget Seizure: The Quest for GABA as a Key Player. *Crit. Rev. Neurobiol.* 2006; 18(1-2):135-144.

Benes F M, Lim B, Matzilevich D, Subburaju S, Walsh J P. Circuitry-based gene expression profiles in GABA cells of the trisynaptic pathway in schizophrenics versus bipolars. *PNAS* 2008 December; 105(52):20935-20940.

Bennett D L, Woods C G. Painful and painless channelopathies. *Lancet Neurol.* 2014 June; 13(6):587-99.

Berge, Bighley and Monkhouse J. Pharm. Sci. (1977) 66, pp 1-19.

Brambilla P, Perez J, Schettini G, Soares J C. GABAergic dysfunction in mood disorders. *Mol. Psych.* 2003 April; 8:721-737.

Brooke R E, Pyner S, McLeish P, Buchan S, Deuchars J, Deuchars S A. Spinal cord interneurones labelled transneuronally from the adrenal gland by a GFP-herpes virus construct contain the potassium channel subunit Kv3.1b. *Auton. Neurosci.* 2002 June; 98(1-2):45-50.

Brooke R E, Atkinson L, Batten T F, Deuchars S A, Deuchars J. Association of potassium channel Kv3.4 subunits with pre- and post-synaptic structures in brainstem and spinal cord. *Neuroscience* 2004; 126(4):1001-10.

Brooke R E, Atkinson L, Edwards I, Parson S H, Deuchars J. Immunohistochemical localisation of the voltage gated potassium ion channel subunit Kv3.3 in the rat medulla oblongata and thoracic spinal cord. *Brain Res.* 2006 January; 1070(1):101-15.

Cervero F. Spinal cord hyperexcitability and its role in pain and hyperalgesia. *Exp. Brain Res.* 2009 June; 196(1):129-37.

Chang S Y, Zagha E, Kwon E S, Ozaita A, Bobik M, Martone M E, Ellisman M H, Heintz N, Rudy B. Distribution of Kv3.3 Potassium Channel Subunits in Distinct Neuronal Populations of Mouse Brain. *J. Comp. Neuro.* 2007 February; 502:953-972.

Chien L Y, Cheng J K, Chu D, Cheng C F, Tsaur M L. Reduced expression of A-type potassium channels in primary sensory neurons induces mechanical hypersensitivity. *J. Neurosci.* 2007 September; 27(37):9855-65.

Chow A, Erisir A, Farb C, Nadal M S, Ozaita A, Lau D, Welker E, Rudy B. $K^+$ Channel Expression Distinguishes Subpopulations of Parvalbumin- and Somatostatin-Containing Neocortical Interneurons. *J. Neurosci.* 1999 November; 19(21):9332-9345.

Deuchars S A, Brooke R E, Frater B, Deuchars J. Properties of interneurones in the intermediolateral cell column of the rat spinal cord: role of the potassium channel subunit Kv3.1. *Neuroscience* 2001; 106(2):433-46.

Devulder J. Flupirtine in pain management: pharmacological properties and clinical use. *CNS Drugs* 2010 October; 24(10):867-81.

Dib-Hajj S D, Yang Y, Black J A, Waxman S G. The Na(V)1.7 sodium channel: from molecule to man. *Nat. Rev. Neurosci.* 2013 January; 14(1):49-62.

Diochot S, Schweitz H, Beress L, Lazdunski M. Sea Anemone Peptides with a Specific Blocking Activity against the Fast Inactivating Potassium Channel Kv3.4. *J. Biol. Chem.* 1998 Ma r; 273(12); 6744-6749.

Dougherty, K. & Covarrubias, M. (2006) *J. Gen. Physiol* 128, 745-753.

Engel A K, Fries P, Singer W. Dynamic Predictions: Oscillations and Synchrony in Top-Down Processing. *Nat. Rev. Neurosci.* 2001 October; 2(10):704-716.

Espinosa F, McMahon A, Chan E, Wang S, Ho C S, Heintz N, Joho R H. Alcohol Hypersensitivity, Increased Locomotion, and Spontaneous Myoclonus in Mice Lacking the Potassium hannels Kv3.1 and Kv3.3. *J. Neurosci.* 2001 September; 21(17):6657-6665.

Espinosa F, Torres-Vega M A, Marks G A, Joho R H. Ablation of Kv3.1 and Kv3.3 Potassium Channels Disrupts Thalamocortical Oscillations In Vitro and In Vivo. *J. Neurosci.* 2008 May; 28(21):5570-5581.

Finnerup N B, Attal N, Haroutounian S, McNicol E, Baron R, Dworkin R H, Gilron I, Haanpai M, Hansson P, Jensen T S, Kamerman P R, Lund K, Moore A, Raja S N, Rice A S, Rowbotham M, Sena E, Siddall P, Smith B H, Wallace M. Pharmacotherapy for neuropathic pain in adults: a systematic review and meta-analysis. *Lancet Neurol.* 2015 February; 14(2):162-73.

Fisahn A. Kainate receptors and rhythmic activity in neuronal networks: hippocampal gamma oscillations as a tool. *J. Physiol.* 2005 October; 561(1):65-72.

Joho R H, Ho C S, Marks G A. Increased $\gamma$- and Decreased $\delta$-Oscillations in a Mouse Deficient for a Potassium Channel Expressed in Fast-Spiking Interneurons. *J. Neurophysiol.* 1999 June; 82:1855-1864.

Joho R H, Hurlock E C. The Role of Kv3-type Potassium Channels in Cerebellar Physiology and Behavior. *Cerebellum* 2009 February; 8:323-333.

Kasten M R, Rudy B, Anderson M P. Differential regulation of action potential firing in adult murine thalamocortical neurons by Kv3.2, Kv1, and SK potassium and N-type calcium channels. *J. Physiol.* 2007; 584(2):565-582.

Kaulin, Y. A., Santiago-Castillo, J. A., Rocha, C. A., & Covarrubias, M. (2008) *Biophys. J.* 94, 1241-1251.

Lau D, Vega-Saenz de Miera E, Contreras D, Ozaita A, Harvey M, Chow A, Noebels J L, Paylor R, Morgan J I, Leonard C S, Rudy B. Impaired Fast-Spiking, Suppressed Cortical Inhibition, and Increased Susceptibility to Seizures in Mice Lacking Kv3.2 $K^+$ Channel Proteins. *J. Neurosci.* 2000 December; 20(24):9071-9085.

Li W, Kaczmarek K, Perney T M. Localization of Two High-Threshol Potassium Channel Subunits in the Rat Central Auditory System. *J. Comp. Neuro.* 2001 May; 437:196-218.

Lu R, Bausch A E, Kallenborn-Gerhardt W, Stoetzer C, Debruin N, Ruth P, Geisslinger G, Leffler A, Lukowski R, Schmidtko A. Slack channels expressed in sensory neurons control neuropathic pain in mice. *J. Neurosci.* 2015 January; 35(3):1125-35.

Markram H, Toledo-Rodriguez M, Wang Y, Gupta A, Silberberg, Wu C. Interneurons of the neocortical inhibitory system. *Nat. Rev. Neurosci.* 2004 October; 5:793-807.

Martina M, Schultz J H, Ehmke H, Monyer H, Jonas P. Functional and Molecular Differences between Voltage-Gated $K^+$ Channels of Fast-Spiking Interneurons and Pyramidal Neurons of Rat Hippocampus. *J. Neurosci.* 1998 October; 18(20):8111-8125.

McCarberg B H, Nicholson B D, Todd K H, Palmer T, Penles L. The impact of pain on quality of life and the unmet needs of pain management: results from pain sufferers and physicians participating in an Internet survey. *Am. J. Ther.* 2008 July-August; 15(4):312-20.

McDonald A J, Mascagni F. Differential expression of Kv3.1b and Kv3.2 potassium channel subunits in interneurons of the basolateral amygdala. *Neuroscience* 2006; 138:537-547.

McMahon A, Fowler S C, Perney T M, Akemann W, Knöpfel, Joho R H. Allele-dependent changes of olivocerebellar circuit properties in the absence of the voltage-gated potassium channels Kv3.1 and Kv3.3. *Eur. J. Neurosci.* 2004 March; 19:3317-3327.

Puente N, Mendizabal-Zubiaga J, Elezgarai I, Reuero L, Buceta I, Grandes P. Precise localization of the voltage-gated potassium channel subunits Kv3.1b and Kv3.3 revealed in the molecular layer of the rat cerebellar cortex by a pre-embedding immunogold method. *Histochem. Cell. Biol.* 2010 September; 134:403-409.

Reynolds G P, Abdul-Monim Z, Neill J C, Zhang Z J. Calcium Binding Protein Markers of GABA Deficits in Schizophrenia—Post Mortem Studies and Animal Models. *Neurotox. Res.* 2004 February; 6(1):57-62.

Ritter D M, Ho C, O'Leary M E, Covarrubias M. Modulation of Kv3.4 channel N-type inactivation by protein kinase C shapes the action potential in dorsal root ganglion neurons. *J. Physiol.* 2012 January; 590(Pt 1):145-61.

Ritter D M, Zemel B M, Hala T J, O'Leary M E, Lepore A C, Covarrubias M. Dysregulation of Kv3.4 channels in dorsal root ganglia following spinal cord injury. *J. Neurosci.* 2015 January; 35(3):1260-73.

Rudy B, McBain C J. Kv3 channels: voltage-gated K+ channels designed for high-frequency repetitive firing. *TRENDS in Neurosci.* 2001 September; 24(9):517-526.

Sacco T, de Luca A, Tempia F. Properties and expression of Kv3 channels in cerebellar Purkinje cells. *Mol. Cell. Neurosci.* 2006 July; 33:170-179.

Schulz P, Steimer T. Neurobiology of Circadian Systems. *CNS Drugs* 2009; 23(Suppl. 2):3-13.

Song P, Yang Y, Barnes-Davies M, Bhattacharjee A, Hamann M, Forsythe I D, Oliver D L, Kaczmarek L K. Acoustic environment determines phosphorylation state of the Kv3.1 potassium channel in auditory neurons *Nat. Neurosci.* 2005 October; 8(10): 1335-1342.

Spencer K M, Nestor P G, Perlmutter R, Niznikiewicz M A, Klump M C, Frumin M, Shenton M E, McCarley R W. Neural synchrony indexes disordered perception and cognition in schizophrenia. *PNAS* 2004 December; 101(49): 17288-17293.

Sun S, Cohen C J, Dehnhardt C M. Inhibitors of voltage-gated sodium channel Nav1.7: patent applications since 2010. *Pharm. Pat. Anal.* 2014 September; 3(5):509-21.

U.S. Department of Health and Human Services, Food and Drug Administration. Draft Guidance for Industry Analgesic Indications: Developing Drug and Biological Products: http://www.fda.gov/downloads/drugs/guidancecomplianceregulatoryinformation/guidances/ucm384691.pdf 2014 February Weiser M, Vega-Saenz de Miera E, Kentros C, Moreno H, Franzen L, Hillman D, Baker H, Rudy B. Differential Expression of Shaw-related K+ Channels in the Rat Central Nervous System. *J. Neurosci.* 1994 March; 14(3): 949-972.

Wickenden A D, McNaughton-Smith G. Kv7 channels as targets for the treatment of pain. *Curr. Pharm. Des.* 2009; 15(15):1773-98.

Woolf C J. What is this thing called pain? *J. Clin. Invest.* 2010 November; 120(11):3742-4.

Woolf C J. Central sensitization: implications for the diagnosis and treatment of pain. *Pain* 2011 March; 152(3 Suppl):S2-15.

Yeung S Y M, Thompson D, Wang Z, Fedida D, Robertson B. Modulation of Kv3 Subfamily Potassium Currents by the Sea Anemone Toxin BDS: Significance for CNS and Biophysical Studies. *J. Neurosci.* 2005 March; 25(38): 8735-8745.

Zamponi G W, Striessnig J, Koschak A, Dolphin A C. *Pharmacol Rev.* 2015 October; 67(4):821-70.

The invention claimed is:

1. A method of treatment of pain in a subject by administering a modulator of Kv3.1 and/or Kv3.2 and/or Kv3.3 wherein the pain is inflammatory pain and wherein the modulator of Kv3.1 and/or Kv3.2 and/or Kv3.3 is capable of producing at least 20% potentiation of whole-cell currents mediated by human Kv3.1 and/or Kv3.2 and/or Kv3.3 channels recombinantly expressed in mammalian cells.

2. A method of treatment of pain in a subject by administering a modulator of Kv3.1 and/or Kv3.2 and/or Kv3.3 wherein the pain is inflammatory pain and wherein the modulator of Kv3.1 and/or Kv3.2 and/or Kv3.3 provides an increase of less than 10% in Kv3.4 current at the same concentration.

3. A method of treatment of pain in a subject by administering a modulator of Kv3.1 and/or Kv3.2 and/or Kv3.3 wherein the pain is inflammatory pain and wherein the modulator of Kv3.1 and/or Kv3.2 and/or Kv3.3 is administered in combination with a further therapeutic agent.

4. The method according to claim 1 wherein the $pEC_{50}$ of the modulator is in the range of 4-7.

5. The method according to claim 1, wherein the modulator of Kv3.1 and/or Kv3.2 and/or Kv3.3 is:

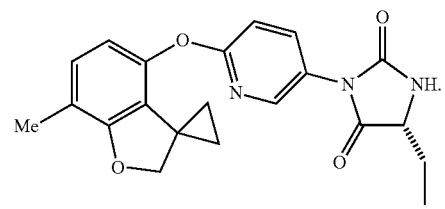 [SMILES: CC[C@H]1NC(=O)N(c2ccc(Oc3ccc(C)c4c3C3(CC3)CO4)nc2)C1=O]

6. The method according to claim 1, wherein the modulator of Kv3.1 and/or Kv3.2 and/or Kv3.3 is:

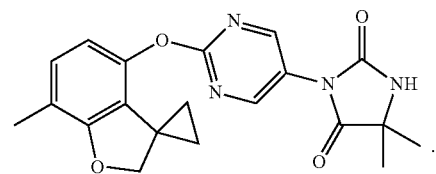

7. The method according to claim 2, wherein the concentration is 10 uM.

8. The method according to claim 2, wherein the modulator of Kv3.1 and/or Kv3.2 and/or Kv3.3 is:

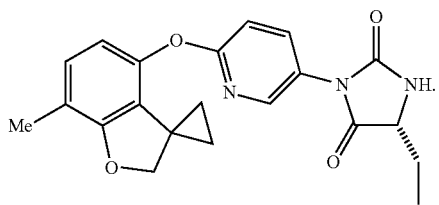 [SMILES: CC[C@H]1NC(=O)N(c2ccc(Oc3ccc(C)c4c3C3(CC3)CO4)nc2)C1=O]
9. The method according to claim 2, wherein the modulator of Kv3.1 and/or Kv3.2 and/or Kv3.3 is:
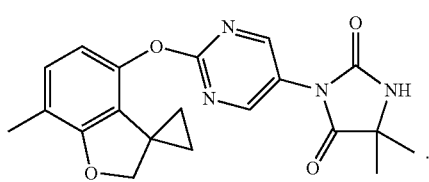
10. The method according to claim 3, wherein the modulator of Kv3.1 and/or Kv3.2 and/or Kv3.3 is:
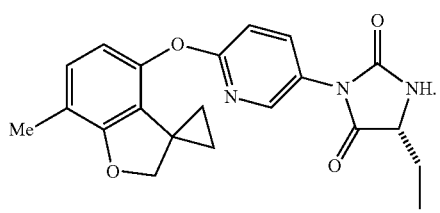 [SMILES: CC[C@H]1NC(=O)N(c2ccc(Oc3ccc(C)c4c3C3(CC3)CO4)nc2)C1=O]
11. The method according to claim 3, wherein the modulator of Kv3.1 and/or Kv3.2 and/or Kv3.3 is:
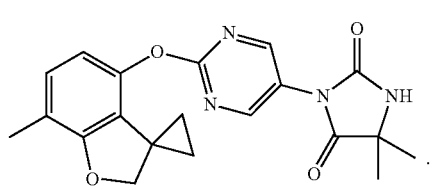
* * * * *